United States Patent
Barbut et al.

(10) Patent No.: US 11,083,735 B2
(45) Date of Patent: Aug. 10, 2021

(54) METHODS FOR TREATING SLEEP DISORDERS, SLEEP DISTURBANCES, AND RELATED SYMPTOMS USING AMINOSTEROL COMPOSITIONS

(71) Applicant: Enterin, Inc., Philadelphia, PA (US)

(72) Inventors: Denise Barbut, Philadelphia, PA (US); Michael Zasloff, Philadelphia, PA (US)

(73) Assignee: Enterin, Inc., Philadelphia, PA (US)

( * ) Notice: Subject to any disclaimer, the term of this patent is extended or adjusted under 35 U.S.C. 154(b) by 0 days.

(21) Appl. No.: 16/122,681

(22) Filed: Sep. 5, 2018

(65) Prior Publication Data

US 2019/0091241 A1    Mar. 28, 2019

Related U.S. Application Data

(60) Provisional application No. 62/556,164, filed on Sep. 8, 2017.

(51) Int. Cl.

| A61K 31/575 | (2006.01) |
| A61P 25/20 | (2006.01) |
| A61P 43/00 | (2006.01) |
| A61K 9/00 | (2006.01) |
| A61K 35/60 | (2006.01) |

(52) U.S. Cl.
CPC .......... *A61K 31/575* (2013.01); *A61K 9/0043* (2013.01); *A61K 9/0053* (2013.01); *A61K 35/60* (2013.01); *A61P 43/00* (2018.01)

(58) Field of Classification Search
CPC .............................. A61K 31/575; A61P 25/20
See application file for complete search history.

(56) References Cited

U.S. PATENT DOCUMENTS

| 5,192,756 A | 3/1993 | Zasloff et al. |
| 5,637,691 A | 6/1997 | Frye et al. |
| 5,721,226 A | 2/1998 | Frye et al. |
| 5,733,899 A | 3/1998 | Frye et al. |
| 5,763,430 A | 6/1998 | Zasloff |
| 5,792,635 A | 8/1998 | Zasloff |
| 5,795,885 A | 8/1998 | Zasloff et al. |
| 5,834,453 A | 11/1998 | Regen |
| 5,840,740 A | 11/1998 | Zasloff et al. |
| 5,840,936 A | 11/1998 | Zasloff et al. |
| 5,847,172 A | 12/1998 | Zasloff et al. |
| 5,856,535 A | 1/1999 | Zasloff et al. |
| 5,874,597 A | 2/1999 | Jones |
| 5,994,336 A | 11/1999 | Zasloff et al. |
| 6,017,906 A | 1/2000 | Mintz et al. |
| 6,143,738 A | 11/2000 | Zasloff |
| 6,147,060 A | 11/2000 | Zasloff et al. |
| 6,388,108 B1 | 5/2002 | Rao et al. |
| 6,596,712 B2 | 7/2003 | Zasloff et al. |
| 6,962,909 B2 | 11/2005 | Zasloff et al. |
| 8,729,058 B2 | 5/2014 | Zasloff |
| 2005/0261508 A1 | 11/2005 | Zasloff et al. |
| 2006/0166950 A1 | 7/2006 | Zasloff et al. |
| 2006/0183928 A1 | 8/2006 | Zasloff et al. |
| 2007/0010504 A1 | 1/2007 | Chellquist et al. |
| 2008/0058300 A1 | 3/2008 | McLane |
| 2011/0097303 A1 | 4/2011 | Zasloff |

FOREIGN PATENT DOCUMENTS

| EP | 1 420 027 A2 | 5/2004 |
| WO | WO 96/08270 A2 | 3/1996 |
| WO | WO 2007/064691 A1 | 6/2007 |
| WO | WO 2009/032321 A1 | 3/2009 |
| WO | WO 2013/158970 A2 | 10/2013 |
| WO | WO 2015/200195 | * 12/2015 |

OTHER PUBLICATIONS

Zasloff et al. Squalamine as a broad-spectrum systemic antiviral agents with therapeutic potential. PNAS, Sep. 20, 2011, vol. 108, No. 38.*
International Search Report and Written Opinion issued in related International Patent Application No. PCT/US2018/049482, dated Jan. 2, 2019.
Ahima et al., "Appetite suppression and weight reduction by a centrally active aminosterol." *Diabetes*, 51(7): 2099-104 (2002).
Akhter et al., "Squalamine, a novel cationic steroid, specifically inhibits the brush-border Na+/H+ exchanger isoform NHE3." *Am. J. Physiol.*, 276(1 Pt 1): C136-44 (1999).
Alexander et al., Membrane surface charge dictates the structure and function of the epithelial na+/h+ exchanger. EMBO J., 30:679-691. (2011).
Bhargava et al., "A phase I and pharmacokinetic study of squalamine, a novel antiangiogenic agent, in patients with advanced cancers," *Clin. Cancer Res.*, 7(12): 3912-9 (2001).
Delgado et al., "Neuroprotective effect of vasoactive intestinal peptide (VIP) in a mouse model of Parkinson's disease by blocking microglial activation." *Faseb. J.*, 17(8): 944-6 (2003).
Genaidy et al., "Effect of squalamine on iris neovascularization in monkeys." *Retina*, 22(6): 772-8 (2002)[Abstract].
Gressens et al., "Vasoactive intestinal peptide prevents excitotoxic cell death in the murine developing brain," *J. Clin. Invest.*, 100(2): 390-7 (1997).
Hao et al., "A Phase I and pharmacokinetic study of squalamine, an aminosterol angiogenesis inhibitor," *Clin. Cancer Res.*, 9(7): 2465-71 (2003).
Herbst et al., "A phase I/IIA trial of continuous five-day infusion of squalamine lactate (MSI-1256F) plus carboplatin and paclitaxel in patients with advanced non-small cell lung cancer," *Clin. Cancer Res.*, 9(11): 4108-15 (2003).

(Continued)

*Primary Examiner* — Theodore R. Howell
(74) *Attorney, Agent, or Firm* — Foley & Lardner LLP

(57) ABSTRACT

This invention relates to methods of treating or preventing a sleep disorder, sleep disturbance, or related symptom in a subject with aminosterols or pharmaceutically acceptable salts or derivatives thereof. In particular, the disclosed methods generally comprise administering an aminosterol to a subject in need, thereby stimulating an aminosterol-induced CNS response to treat and/or prevent a sleep disorder, sleep disturbance, or related symptom.

20 Claims, 29 Drawing Sheets

(56) References Cited

OTHER PUBLICATIONS

Gonzalez-Rey et al., "Therapeutic effect of vasoactive intestinal peptide on experimental autoimmune encephalomyelitis: down-regulation of inflammatory and autoimmune responses," *Am. J. Pathol.*, 168(4): 1179-88 (2006).
Higgins et al., "Squalamine improves retinal neovascularization," *Invest. Ophthalmol. Vis. Sci.*, 41(6): 1507-12 (2000).
MacDonald, D. (1995). "Squalamine for STDs." Abstract No. F7 35th ICAAC conference, 45 pages.
Moore et al., "Squalamine: an aminosterol antibiotic from the shark," *Proc. Natl. Acad. Sci. USA*, 90(4): 1354-8 (1993).
Rao et al., "Aminosterols from the dogfish shark *Squalus acanthias*," *J. Nat. Prod.*, 63(5): 631-5 (2000) [Abstract].
Li et al., "GLP-1 receptor stimulation preserves primary cortical and dopaminergic neurons in cellular and rodent models of stroke and Parkinsonism," *Proc. Natl. Acad. Sci. USA*, 106(4): 1285-90 (2009).
Li et al., "Squalamine and cisplatin block angiogenesis and growth of human ovarian cancer cells with or without HER-2 gene overexpression," *Oncogene*, 21(18): 2805-14 (2002).
Higgins et al., "Regression of retinopathy by squalamine in a mouse model," *Pediatr. Res.*, 56(1): 1449 (2004).
Salmi et al., "New stereoselective titanium reductive amination synthesis of 3-amino and polyaminosterol derivatives possessing antimicrobial activities," *Eur. J. Med. Chem.*, 43(3): 540-7 (2008) [Abstract].
Schiller, J. H. and G. Bittner, "Potentiation of platinum antitumor effects in human lung tumor xenografts by the angiogenesis inhibitor squalamine: effects on tumor neovascularization," *Clin. Cancer Res.*, 5(12): 4287-94 (1999).
Selinsky et al., "Squalamine is not a proton ionophore," *Biochim. Biophys. Acta.*, 1464(1): 135-41 (2000).
Selinsky et al., "The aminosterol antibiotic squalamine permeabilizes large unilamellar phospholipid vesicles," *Biochim. Biophys. Acta.*, 1370(2): 218-34 (1998).
Sills et al., "Squalamine inhibits angiogenesis and solid tumor growth in vivo and perturbs embryonic vasculature," *Cancer Res.*, 58(13): 2784-92 (1998).
Salmi et al., "Squalamine: an appropriate strategy against the emergence of multidrug resistant gram-negative bacteria?" PLoS ONE, 3(7): e2765 (2008).
Sokoloff et al., "Adjunctive therapy for men with high risk localized and locally advanced prostate cancer: targeting disseminated tumor cells," *J. Urol.*, 172(6 Pt 2): 2539-44 (2004) [Abstract].
Tirassa et al., "CCK-8 prevents the development of kindling and regulates the GABA and NPY expression in the hippocampus of pentylenetetrazole (PTZ)-treated adult rats," *Neuropharmacology*, 48(5): 732-42 (2005) [Abstract].
Sumioka et al., "TARP phosphorylation regulates synaptic AMPA receptors through lipid bilayers," *Neuron*, 66(5): 755-67 (2009).
Verdin et al., "Characterization of a common high-affinity receptor for reovirus serotypes 1 and 3 on endothelial cells," *J. Virol.*, 63(3): 1318-25 (1989).
White et al., "Therapeutic potential of vasoactive intestinal peptide and its receptors in neurological disorders," *CNS Neurol. Disord. Drug Targets*, 9(5): 661-6 (2010).
Williams et al., "Squalamine treatment of human tumors in nu/nu mice enhances platinum-based chemotherapies," *Clin. Cancer Res.*, 7(3): 724-33 (2001).
Yeung et al., "Membrane phosphatidylserine regulates surface charge and protein localization," *Science*, 319(5860): 210-3 (2008) [Abstract].
Zasloff, M., "Antimicrobial peptides of multicellular organisms," *Nature*, 415(6870): 389-95 (2002) [Abstract].
Yin et al., "Antiangiogenic treatment delays chondrocyte maturation and bone formation during limb skeletogenesis," *J. Bone Miner. Res.*, 17(1): 56-65 (2002).
Zasloff et al., "A spermine-coupled cholesterol metabolite from the shark with potent appetite suppressant and antidiabetic properties," *Int. J. Obes. Relat. Metab. Disord.*, 25(5): 689-97 (2001).
Zasloff et al., "Squalamine as a broad-spectrum systemic antiviral agent with therapeutic potential," *Proc. Natl. Acad. Sci. USA*, 108(38): 15978-83 (2011).
Steinberg, B. E. and S. Grinstein, "Pathogen destruction versus intracellular survival: the role of lipids as phagosomal fate determinants," *J. Clin. Invest.*, 118(6): 2002-11 (2008).
Connolly et al., "Squalamine lactate for exudative age-related macular degeneration," Ophthalmol. Clin. North Am., 19:381-91 (2006).
Sarabia et al., "Circadian rhythm of wrist temperature in normal-living subjects a candidate of new index of the circadian system," Physiol. Behav., 95:570-80 (2008).
Yun et al., "Identification of Squalamine in the Plasma Membrane of White Blood Cells in the Sea Lamprey," *Petromyzon marinus*, J. Lipid Res., 48(12): 2579-2586 (2007).

\* cited by examiner

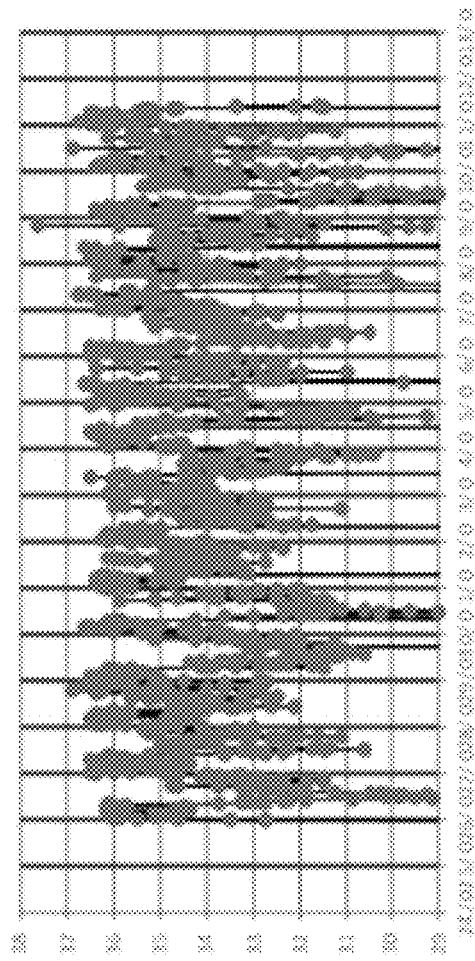
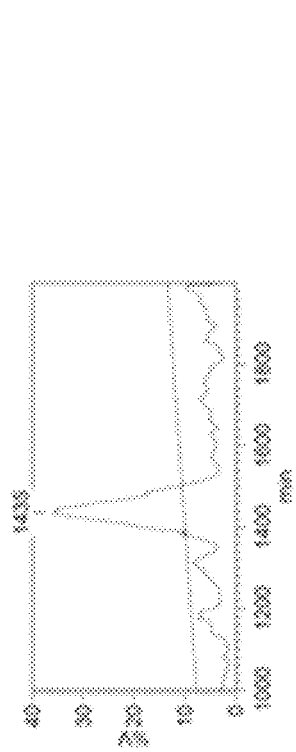
FIG. 11A
FIG. 11B

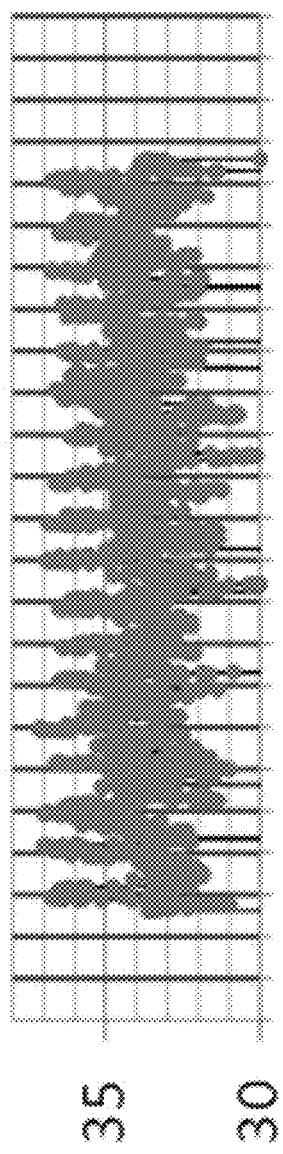
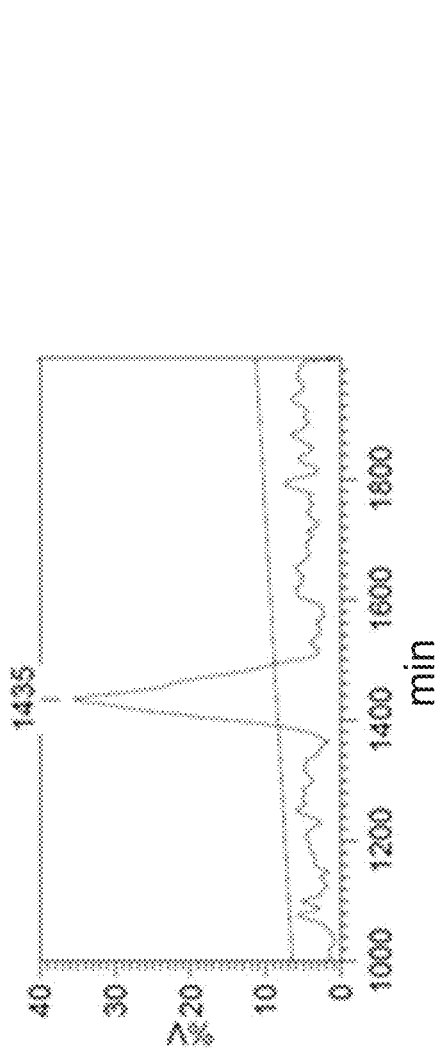
FIG. 12A
FIG. 12B

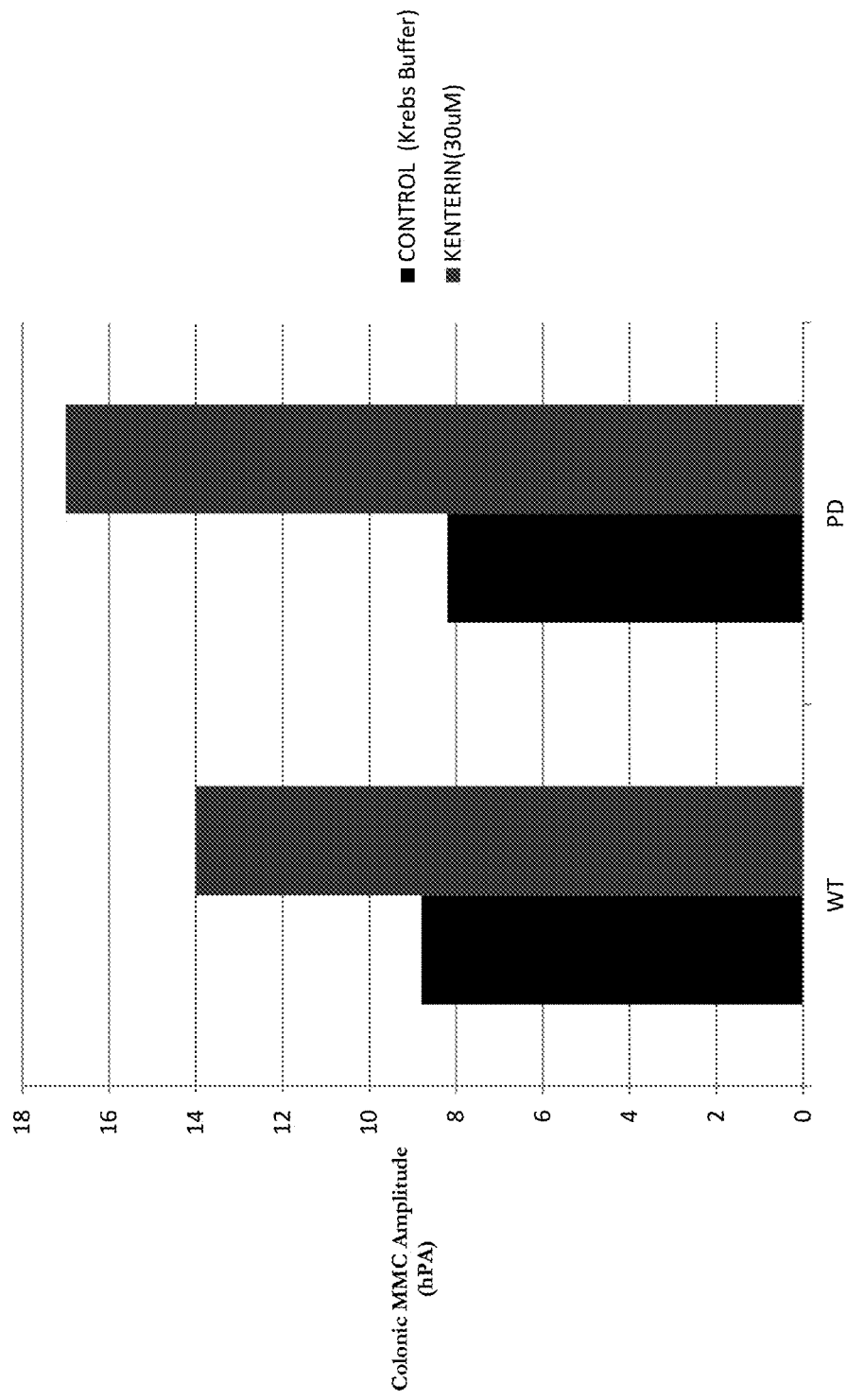

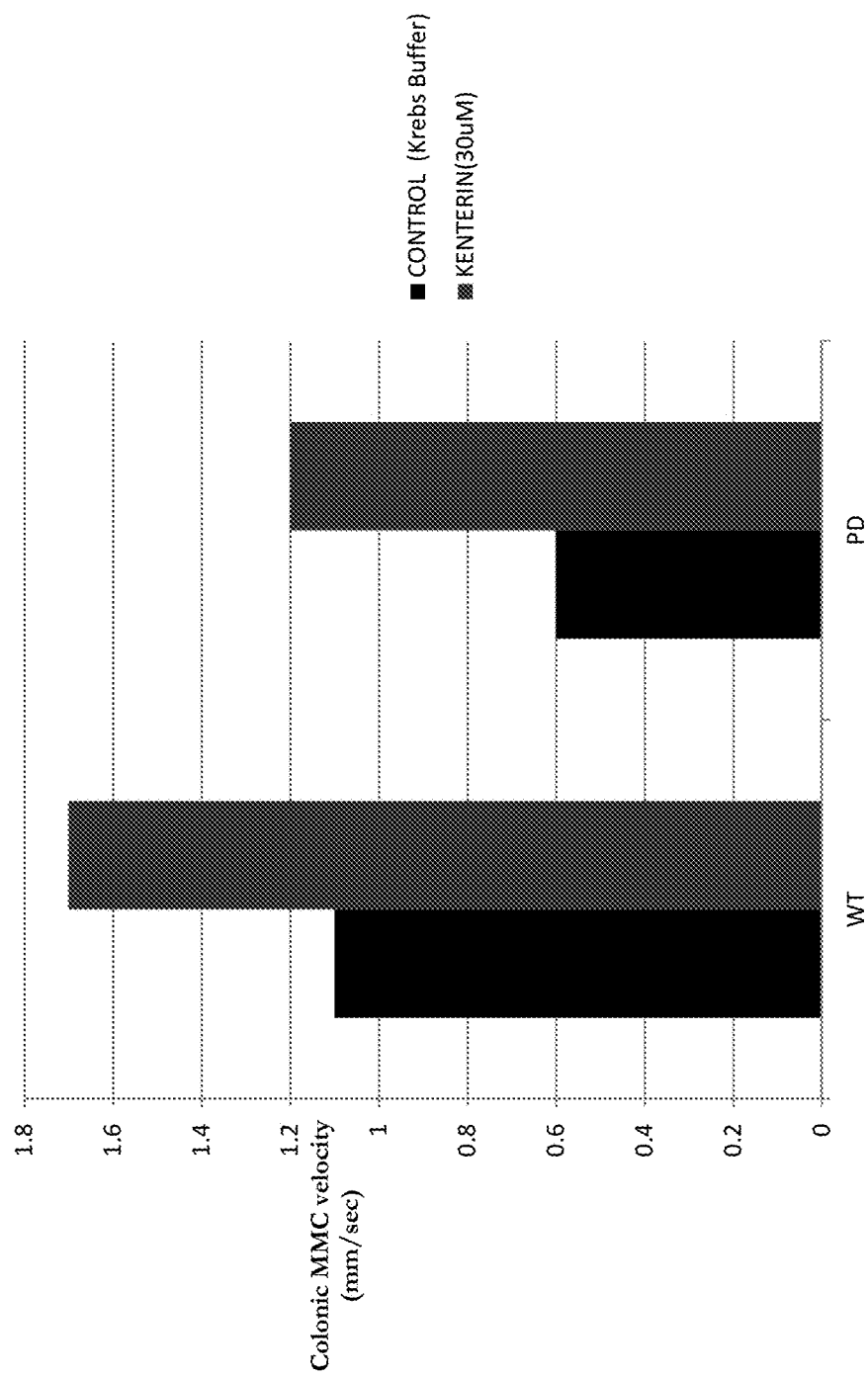

METHODS FOR TREATING SLEEP DISORDERS, SLEEP DISTURBANCES, AND RELATED SYMPTOMS USING AMINOSTEROL COMPOSITIONS

CROSS-REFERENCE TO RELATED APPLICATION

This application claims priority of U.S. Provisional Patent Application No. 62/556,164, filed on Sep. 8, 2017, the contents of which are incorporated herein by reference in their entirety.

FIELD OF THE INVENTION

This application relates to methods of treating, preventing, or improving sleep disorders and/or sleep disturbances, or related symptoms, in human subjects. The method comprises administering to a subject in need thereof an aminosterol, or a salt or derivative thereof.

BACKGROUND OF THE INVENTION

Squalamine is a unique compound with a structure that was not previously seen in nature, being a bile acid coupled to a polyamine (spermidine):

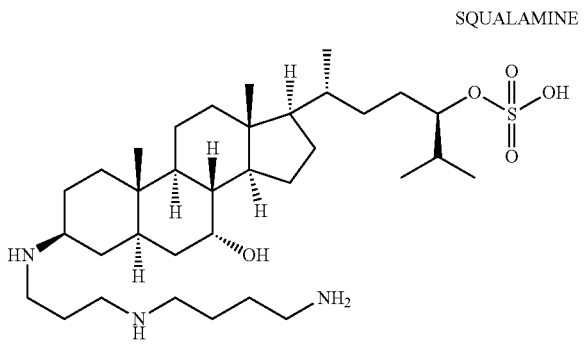

SQUALAMINE

The discovery of squalamine, the structure of which is shown above, was reported by Michael Zasloff in 1993 (U.S. Pat. No. 5,192,756). Squalamine was discovered in various tissues of the dogfish shark (*Squalus acanthias*) in a search for antibacterial agents. The most abundant source of squalamine is in the livers of *Squalus acanthias*, although it is found in other sources, such as lampreys (Yun et al., 2007).

Numerous studies later demonstrated that squalamine exhibits potent antibacterial activity in vitro (Salmi, Loncle et al. 2008). Subsequently, squalamine was discovered to exhibit antiangiogenic activity in vitro and upon administration to animals (Sills, Williams et al. 1998; Yin, Gentili et al. 2002). As a consequence, squalamine has been evaluated in disease states known to be associated with pathological neovascularization, such as cancer (Sills, Williams et al. 1998; Schiller and Bittner 1999; Bhargava, Marshall et al. 2001; Williams, Weitman et al. 2001; Hao, Hammond et al. 2003; Herbst, Hammond et al. 2003; Sokoloff, Rinker-Schaeffer et al. 2004), and vascular disorders of the eye, including macular degeneration (US2007/10504A1 2007), retinopathy of prematurity (Higgins, Sanders et al. 2000; Higgins, Yan et al. 2004; US2007/10504A1 2007), corneal neovascularization (Genaidy, Kazi et al. 2002) and diabetic retinopathy (US2007/10504A1 2007). Recent studies have highlighted the efficacy of systemically administered squalamine to prevent or treat viral infections in animals (Zasloff et al. (2011); U.S. Pat. No. 8,729,058). Squalamine and related aminosterols, such as Aminosterol 1436 (also isolated from the dogfish shark, see U.S. Pat. No. 5,840,936; Rao, Shinnar et al. 2000) have been studied to treat far ranging conditions including HIV, cancer, and even appetite suppression.

Squalamine is a cationic amphipathic substance exhibiting an affinity for membranes composed of anionic phospholipids (Selinsky, Zhou et al. 1998; Selinsky, Smith et al. 2000).

Several clinical trials have been conducted relating to the use of squalamine, including the following:

(1) ClinicalTrials.gov Identifier NCT01769183 for "Squalamine for the Treatment in Proliferative Diabetic Retinopathy," by Elman Retina Group (6 participants; study completed August 2014);

(2) ClinicalTrials.gov Identifier NCT02727881 for "Efficacy and Safety Study of Squalamine Ophthalmic Solution in Subjects With Neovascular AMD (MAKO)," by Ohr Pharmaceutical Inc. (230 participants; study completed December 2017);

(3) ClinicalTrials.gov Identifier NCT02614937 for "Study of Squalamine Lactate for the Treatment of Macular Edema Related to Retinal Vein Occlusion," by Ohr Pharmaceutical Inc. (20 participants; study completed December 2014);

(4) ClinicalTrials.gov Identifier NCT01678963 for "Efficacy and Safety of Squalamine Lactate Eye Drops in Subjects With Neovascular (Wet) Age-related Macular Degeneration (AMD)," by Ohr Pharmaceutical Inc. (142 participants; study completed March 2015);

(5) ClinicalTrials.gov Identifier NCT00333476 for "A Study of MSI-1256F (Squalamine Lactate) To Treat "Wet" Age-Related Macular Degeneration," by Genaera Corporation (140 participants; study terminated);

(6) ClinicalTrials.gov Identifier NCT00094120 for "MSI-1256F (Squalamine Lactate) in Combination With Verteporfin in Patients With 'Wet' Age-Related Macular Degeneration (AMD)," by Genaera Corporation (60 participants; study completed February 2007);

(7) ClinicalTrials.gov Identifier NCT00089830 for "A Safety and Efficacy Study of MSI-1256F (Squalamine Lactate) To Treat 'Wet' Age-Related Macular Degeneration," by Genaera Corporation (120 participants; study completed May 2007); and (8) ClinicalTrials.gov Identifier NCT03047629 for Evaluation of Safety and Tolerability of ENT-01 for the Treatment of Parkinson's Disease Related Constipation (RASMET) (50 participants; study completed Jun. 14, 2018).

Squalamine is also marketed under the brand name Squalamax™ as a dietary supplement, though it has not been approved as a drug in this form and thus cannot make therapeutic claims. Squalamax™ is an unfractionated extract of shark liver, containing innumerable uncharacterized substances in addition to squalamine, and squalamine is present in Squalamax™ at less than 0.01% of the total weight of the extract. "Cyber Warning Letter", Center for Drug Evaluation and Research (2002 May 6), http://www.fda.gov/CDER/warn/cyber/2002/CFSANnuGen.htm; Retrieved 2009 Mar. 31. Moreover, the dietary supplement form of squalamine is not pharmaceutical grade squalamine, as pharmaceutical grade squalamine requires significantly greater manufacturing efforts.

By 2006, over 300 patients had received squalamine in doses ranging from 6-700 mg/m²/day by iv administration, in three Phase I and nine Phase II studies. (Hao et al. 2003; Herbst et al. 2003; Bhargava et al. 2001; and Connolly et al.

2006). The studies showed that the compound exhibited an acceptable safety profile and evidence of efficacy in these early trials. In 2006 development of squalamine was halted for economic/strategic reasons by Genaera. In 2011 Ohr Pharmaceuticals initiated studies of the compound administered as an eye drop for the treatment of retinal eye disease, but all studies of this compound against cancer have remained in a dormant stage since.

The mechanism of action. It has been reported that squalamine exerts its effects at the cellular level by displacing proteins bound electrostatically to negatively charged membranes, causing pleiotropic changes in the functional state of the cell (Alexander et al. 2011; Yeung et al. 2008; Sumioka et al. 2009; Zasloff et al. 2011).

Aminosterol 1436 is an aminosterol isolated from the dogfish shark, which is structurally related to squalamine (U.S. Pat. No. 5,840,936; Rao, Shinnar et al. 2000). Aminosterol 1436 exhibits antiviral activity against HIV in tissue culture (U.S. Pat. No. 5,763,430) via a mechanism proposed to involve inhibition of a lymphocyte-specific NHE by 1436, resulting in suppression of cytokine responsiveness, and subsequent depression of the capacity of the lymphocyte to support HIV replication (U.S. Pat. No. 5,763,430). Aminosterol 1436, however, has an additional pharmacological property, not shared with squalamine, namely potent appetite suppression and promotion of dose-dependent weight loss (U.S. Pat. No. 6,143,738; Ahima et al. 2002).

Several clinical trials have been conducted relating to the use of Aminosterol 1436:

(1) ClinicalTrials.gov Identifier NCT00509132 for "A Phase I, Double-Blind, Randomized, Placebo-Controlled Ascending IV Single-Dose Tolerance and Pharmacokinetic Study of Trodusquemine in Healthy Volunteers," by Genaera Corp.;

(2) ClinicalTrials.gov Identifier NCT00606112 for "A Single Dose, Tolerance and Pharmacokinetic Study in Obese or Overweight Type 2 Diabetic Volunteer," by Genaera Corp.;

(3) ClinicalTrials.gov Identifier NCT00806338 for "An Ascending Multi-Dose, Tolerance and Pharmacokinetic Study in Obese or Overweight Type 2 Diabetic Volunteers," by Genaera Corp.; and (4) ClinicalTrials.gov Identifier: NCT02524951 for "Safety and Tolerability of MSI-1436C in Metastatic Breast Cancer," by DepyMed Inc.

Extensive studies in animals have shown that neither squalamine nor Aminosterol 1436 can be absorbed to any extent from the gastrointestinal tract, requiring parenteral administration for the various previously conceived applications of these compounds. Aminosterol 1436, although capable of inducing weight loss when administered parenterally to dogs, and rodents exhibited no anorectic activity when administered orally, consistent with its poor bioavailability when delivered orally. Indeed, in a published review on the applications of squalamine as a therapeutic, Genaera scientists state "Although squalamine lactate is well absorbed in rodents by the subcutaneous and intraperitoneal routes, preliminary studies indicate that it is poorly bioavailable orally." (Connolly et al. 2006).

Squalamine and related aminosterols, such as 1436, do not exit the gastrointestinal tract into either the portal or systemic blood stream. This resulted in generally accepted conclusions by those skilled in the art of drug development that aminosterols could not provide any benefit for systemic conditions when administered orally. Thus, it was entirely unknown that squalamine could be orally or nasally administered for the treatment of sleep disorders.

There is a need in the art for new methods of treating and preventing sleep disorders. The present invention satisfies this need.

SUMMARY OF THE INVENTION

The present invention is directed to methods of treating and/or preventing sleep disorders, sleep disturbance, or related symptom in a subject. The method comprises administering a composition comprising a pharmaceutically acceptable grade of at least one aminosterol, or a pharmaceutically acceptable salt or derivative thereof, in an amount sufficient to produce a beneficial effect to a subject in need. Suitable "aminosterols" are described herein, and include for example squalamine or a pharmaceutically acceptable salt or derivative thereof, Aminosterol 1436 or a pharmaceutically acceptable salt or derivative thereof, or an aminosterol isolated from *Squalus acanthias* or a pharmaceutically acceptable salt or derivative thereof. The composition can comprise one or more pharmaceutically acceptable carriers. For the purposes of this application, the subject is generally human.

In another aspect, encompassed are methods of treating and/or preventing sleep disorders, sleep disturbance, or related symptom in a subject comprising (a) determining a dose of an aminosterol or a pharmaceutically acceptable salt or derivative thereof for the subject, wherein the aminosterol dose is determined based on the effectiveness of the aminosterol dose in improving or resolving a sleep disorder, sleep disturbance, or related symptom being evaluated, (b) followed by administering the aminosterol dose to the subject for a period of time, wherein the method comprises: (i) identifying a sleep disorder, sleep disturbance, or related symptom to be evaluated; (ii) identifying a starting aminosterol dose for the subject; and (iii) administering an escalating dose of the aminosterol to the subject over a period of time until an effective dose for the sleep disorder, sleep disturbance, or related symptom being evaluated is identified, wherein the effective dose is the aminosterol dose where improvement or resolution of the sleep disorder, sleep disturbance, or related symptom is observed, and fixing the aminosterol dose at that level for that particular sleep disorder, sleep disturbance, or related symptom in that particular subject.

In the methods of the invention, the sleep disorder, sleep disturbance, or related symptom to be evaluated in optimizing a dose of an aminosterol or a pharmaceutically acceptable salt or derivative thereof, can be selected from the group consisting of (1) total sleep time; (2) total number of hours of uninterrupted sleep, per day; (3) sleep efficiency; (4) presence or frequency of a change in sleeping patterns; (5) presence or frequency of a change in Circadian rhythm; (6) developing a normal Circadian (i.e., diurnal) rhythm; (7) presence of a sleep-wake cycle that is not 24 hours; (8) sleeping at night rather than during the day, when night would is the preferred sleeping period; (9) presence and/or frequency of awakenings during sleep period; (10) presence and/or frequency of nonrestorative sleep; (11) presence and/or frequency of a difficulty maintaining sleep; (12) presence and/or frequency of sleep fragmentation; (13) presence and/or frequency of hallucinations during sleep period; (14) presence and/or frequency of thrashing or limb movement during sleep period; (15) presence and/or frequency of nightmares and/or vivid dreams; (16) presence and/or frequency of delayed sleep onset; (17) presence and/or frequency of day time sleepiness; (18) presence and/or frequency of clinical or sub-clinical "sleep attacks";

(19) cognitive impairment and/or improvement in memory as a result of better memory consolidation during sleep; (20) presence and/or frequency of disturbances in sleep architecture; (21) time of awakening following sleep period, with a later time correlated with improved sleep; (22) presence and/or frequency of sleep problems; (23) presence and/or frequency of sleep disturbances and/or sleep disruption; (24) REM disturbed sleep; (25) presence and/or frequency of apnea; (26) presence and/or frequency of narcolepsy; (27) poor psychomotor coordination; (28) presence and/or frequency of headaches; (29) presence and/or frequency of gastrointestinal distress; (30) presence and/or frequency of insomnia; (31) presence and/or frequency of parasomnias; (32) diurnal skin temperature oscillations; (33) a symptom from the Horne-Östberg Morningness-Eveningness Questionnaire (MEQ) selected from the group consisting of difficulty waking up in the morning, difficulty falling asleep at night, falling asleep earlier than normal at night, dependence on alarm to wake in morning, lack of alertness in morning, appetite upon waking in morning, feeling tired after waking in the morning, going to bed later than normal when subject has no commitments the following day, inability to fall back to sleep upon waking in the morning, lack of willingness to engage in physical activity in the morning, and lack of willingness to engage in cognitively challenging tasks in the morning; (33) a symptom from the Epworth Sleepiness Scale (ESS) selected from the group consisting of dozing or sleeping when sitting and reading, dozing or sleeping when watching television (TV), dozing or sleeping when sitting while inactive in public, dozing or sleeping when riding as a passenger in a car for greater than 1 hour, dozing or sleeping when lying down in the afternoon, dozing or sleeping when talking to another person, dozing or sleeping when sitting quietly after lunch, and dozing or sleeping when driving and stopped in traffic; (35) REM behavior disorder (RBD); 36) circadian rhythm dysfunction; (37) Restless leg syndrome; (38) jet lag; (39) hypersomnia; and/or (40) personal judgment of restful sleep.

In another embodiment, the starting dose of the aminosterol or a salt or derivative thereof is higher if the symptom being evaluated is severe.

In the methods of the invention, the aminosterol compositions can be administered via any pharmaceutically acceptable means. Oral administration, intranasal administration, or a combination thereof are preferred.

In one embodiment, in the methods of the invention each aminosterol dose is taken on an empty stomach, optionally within two hours of the subject waking. In addition, in another embodiment, in the methods of the invention no food is taken after about 60 to about 90 minutes of taking the aminosterol dose.

In another embodiment, where the composition is administered orally, (a) the starting aminosterol dose ranges from about 1 mg up to about 175 mg/day; and/or (b) the dose of the aminosterol or a salt or derivative thereof for the subject following escalation is fixed at a range of from about 1 mg up to about 500 mg/day; and/or (c) the dose of the aminosterol or a salt or derivative thereof is escalated in about 25 mg increments.

In yet another embodiment, where the composition is administered intranasally, (a) the starting dose of the aminosterol or a salt or derivative thereof ranges from about 0.001 mg to about 3 mg/day; and/or (b) the dose of the aminosterol or a salt or derivative thereof for the subject following escalation is fixed at a range of from about 0.001 mg up to about 6 mg/day; and/or (c) the dose of the aminosterol or a salt or derivative thereof for the subject following escalation is a dose which is subtherapeutic when given orally or by injection; and/or (d) the dose of the aminosterol or a salt or derivative thereof is escalated in increments of about 0.1, about 0.2, about 0.25, about 0.3, about 0.35, about 0.4, about 0.45, about 0.5, about 0.55, about 0.6, about 0.65, about 0.7, about 0.75, about 0.8, about 0.85, about 0.9, about 0.95, about 1, about 1.1, about 1.2, about 1.3, about 1.4, about 1.5, about 1.6, about 1.7, about 1.8, about 1.9, or about 2 mg.

In a further embodiment, the dose of the aminosterol or a pharmaceutically acceptable salt or derivative thereof can be escalated by various time periods. For example, the dose of the aminosterol or a pharmaceutically acceptable salt or derivative thereof can be escalated (a) every about 3 to about 5 days; (b) every about 1, about 2, about 3, about 4, about 5, about 6, about 7, about 8, about 9, about 10, about 11, about 12, about 13, or about 14 days; or (c) about 1x/week, about 2x/week, about every other week, or about 1x/month.

In one embodiment, the dose of the aminosterol or a pharmaceutically acceptable salt or derivative thereof is given once per day, every other day, once per week, twice per week, three times per week, four times per week, five times per week, six times per week, every other week, or every few days. In another embodiment, the dose of the aminosterol or a pharmaceutically acceptable salt or derivative thereof is given for a few weeks, followed by skipping a few weeks, followed by restarting aminosterol treatment. In a further embodiment, the dose of the aminosterol or a pharmaceutically acceptable salt or derivative thereof is incrementally reduced after the fixed dose of aminosterol or a salt or derivative thereof has been administered to the subject for a period of time. For example, the dose of the aminosterol or a pharmaceutically acceptable salt or derivative thereof can be varied plus or minus a defined amount to enable a modest reduction or increase in the fixed dose. As yet another example, the dose of the aminosterol or a pharmaceutically acceptable salt or derivative thereof can be varied plus or minus a defined amount to enable a modest reduction or increase in the fixed dose, and the fixed aminosterol dose is increased or decreased by about 1%, about 2%, about 3%, about 4%, about 5%, about 6%, about 7%, about 8%, about 9%, about 10%, about 11%, about 12%, about 13%, about 14%, about 15%, about 16%, about 17%, about 18%, about 19%, or about 20%.

In some embodiments, administration of the composition decreases the occurrence of at least one symptom of the sleep disorder or disturbance. In other embodiments, administration of the aminosterol composition results in slowing, halting, or reversing progression or onset of the sleep disorder, sleep disturbance or related symptom over a defined time period, as measured by a medically-recognized technique, tool or scale. For example, the progression or onset of the sleep disorder, disturbance or related symptom can be slowed, halted, or reversed by about 5%, about 10%, about 15%, about 20%, about 25%, about 30%, about 35%, about 40%, about 45%, about 50%, about 55%, about 60%, about 65%, about 70%, about 75%, about 80%, about 85%, about 90%, about 95%, or about 100%, as measured by a medically-recognized technique, tool or scale.

In a further embodiment, administration of the aminosterol composition results in positively impacting the sleep disorder, sleep disturbance or related symptom, as measured by a clinically-recognized technique, tool or scale. For example, the positive impact on the sleep disorder, disturbance, or related symptom can be at least about 10%, at least about 15%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 95%, or at least about 100%, as measured using a clinically recognized scale, tool, or technique.

The invention encompasses methods where the sleep disorder, disturbance or related symptom (a) comprises a dyssomnia, parasomnia, and/or circadian rhythm sleep disorder; and/or (b) comprises a loss of diurnal rhythm (Circadian rhythm); and/or (c) comprises a delay in sleep onset, sleep fragmentation, REM-behavior disorder (RBD), sleep-disordered breathing including snoring and apnea, day-time sleepiness, micro-sleep episodes, narcolepsy, hallucinations, hypersomnia, Restless leg syndrome (RLS), Periodic limb movement disorder (PLMD), insomnia, gastrointestinal distress, headache, narcolepsy, REM disturbed sleep, clinical or sub-clinical "sleep attacks", thrashing or limb movement during sleep period, nonrestorative sleep, awakenings during sleep period, cognitive impairment, sleep problems, poor psychomotor coordination, bruxism, catathrenia, cataplexy, sleep walking, Delayed sleep phase disorder (DSPD), advanced sleep phase disorder (ASPD), non-24-hour sleep-wake disorder (non-24) in the sighted or in the blind, irregular sleep wake rhythm, Shift work sleep disorder (SWSD), Hypopnea syndrome, Idiopathic hypersomnia, Kleine-Levin syndrome, sleep terror disorder, nocturia, sleep paralysis, somniphobia, or any combination thereof; and/or (d) comprises or is associated with a neurodegenerative disorder or disease.

Where the sleep disorder, sleep disturbance or related system encompasses a loss of diurnal rhythm, the invention encompasses aspects where (a) the loss of diurnal rhythm is caused by dysfunction of the suprachiasmatic nucleus, and administration of the composition reverses the dysfunction of the suprachiasmatic nucleus, restores the diurnal rhythm, and treats the sleep disorder, sleep disturbance, or related symptom; (b) the loss of diurnal rhythm is caused by dysfunction of the enteric nervous system, and administration of the composition reverses the dysfunction of the enteric nervous system, restores the diurnal rhythm, and treats the sleep disorder, sleep disturbance, or related symptom; (c) the loss of diurnal rhythm is caused by dysfunction of the olfactory nervous system, and administration of the composition reverses the dysfunction of the olfactory nervous system, restores the diurnal rhythm, and treats the sleep disorder, sleep disturbance, or related symptom; (d) the loss of diurnal rhythm is caused by visual loss, and administration of the composition reverses the dysfunction of the circadian rhythm caused by visual loss; (e) the loss of diurnal rhythm is caused by jet lag, and administration of the composition reverses the dysfunction of circadian rhythm caused by jet lag; and/or (f) the loss of diurnal rhythm is caused by night-shift work, and administration of the composition reverses the dysfunction of the circadian rhythm caused by night-shift work.

Where the sleep disorder, sleep disturbance or related system encompasses a neurodegenerative disorder or disease, the invention encompasses aspects where (a) treating the sleep disorder, sleep disturbance, or related symptom prevents or delays the onset or progression of the neurodegenerative disorder; and/or (b) the neurodegenerative disorder is selected from the group consisting of Parkinson's disease, Alzheimer's disease, Huntington's chorea and/or Disease, schizophrenia, multiple sclerosis, dementia, degenerative processes associated with aging, dementia of aging, multi-system atrophy (MSA), fronto-temporal dementia, autism, progressive nuclear palsy, Guadeloupian Parkinsonism, spinocerebellar ataxia, Amyotorphic Lateral Sclerosis (ALS), Friedreich's ataxia, vascular dementia, Lewy Body dementia or disease, spinal muscular atrophy, supranuclear palsy, fronto temporal dementia, neuropathy of diabetes, peripheral sensory neuropathy, cerebral palsy, epilepsy, diabetic neuropathy, and depression.

In some embodiments, the method results in a positive change in the sleeping pattern of the subject. For example, in some embodiments the positive change is defined as an increase in the total amount of sleep obtained of about 5%, about 10%, about 15%, about 20%, about 25%, about 30%, about 35%, about 40%, about 45%, about 50%, about 55%, about 60%, about 65%, about 70%, about 75%, about 80%, about 85%, about 90%, about 95%, and about 100%. In some embodiments, the positive change is defined as a percent decrease in the number of awakenings during the night selected from the group consisting of about 5%, about 10%, about 15%, about 20%, about 25%, about 30%, about 35%, about 40%, about 45%, about 50%, about 55%, about 60%, about 65%, about 70%, about 75%, about 80%, about 85%, about 90%, about 95%, or about 100%.

In some embodiments, the subject is an infant patient, a toddler patient, a school-aged child patient, a teenager patient, a young adult patent, an adult patient, or an elderly patient.

In some embodiments, the subject obtains the total number of hours of sleep recommended by a medical authority for the age group of the subject.

The aminosterol or a pharmaceutically acceptable salt or derivative thereof can be any known aminosterol. In some embodiments, the aminosterol is isolated from the liver of *Squalus acanthias*. In some embodiments, the aminosterol is squalamine or a pharmaceutically acceptable salt thereof, a squalamine isomer or derivative, aminosterol 1436 or a pharmaceutically acceptable salt thereof, or an aminosterol 1436 isomer or derivative.

In some embodiments, the aminosterol comprises a sterol nucleus and a polyamine attached at any position on the sterol, such that the molecule exhibits a net charge of at least +1. In other embodiments, the aminosterol comprises a bile acid nucleus and a polyamine, attached at any position on the bile acid, such that the molecule exhibits a net charge of at least +1. In some embodiments, the polyamine contributes to the net charge.

In some embodiments, the aminosterol is a derivative modified to include one or more of the following: (a) substitutions of the sulfate by a sulfonate, phosphate, carboxylate, or other anionic moiety chosen to circumvent metabolic removal of the sulfate moiety and oxidation of the cholesterol side chain; (b) replacement of a hydroxyl group by a non-metabolizable polar substituent, such as a fluorine atom, to prevent its metabolic oxidation or conjugation; and (c) substitution of one or more ring hydrogen atoms to prevent oxidative or reductive metabolism of the steroid ring system.

In some embodiments, the aminosterol is a derivative of squalamine, aminosterol 1436, or a natural aminosterol, modified through medicinal chemistry to improve bio-distribution, ease of administration, metabolic stability, or any combination thereof.

In some embodiments, the aminosterol is a phosphate salt.

In yet another embodiment, the composition further comprises one or more of the following: (a) an aqueous carrier; (b) a buffer; (c) a sugar; and/or (d) a polyol compound.

In another aspect of the invention, encompassed are methods where the aminosterol or a pharmaceutically acceptable salt or derivative thereof is administered in combination with at least one additional active agent to achieve either an additive or synergistic effect. The additional active agent is administered via a method selected from the group consisting of concomitantly, as an admixture, separately and simultaneously or concurrently, and separately and sequentially. In one embodiment, the additional active agent is a different aminosterol from that administered in the primary method. In another embodiment, the method comprises a first aminosterol which is aminosterol 1436 or a pharmaceutically acceptable salt or derivative thereof administered intranasally and a second aminosterol which is squalamine or a pharmaceutically acceptable salt or derivative thereof administered orally. In yet a further embodiment, the additional active agent is an active agent used to treat sleep disorders, sleep disruption, or a related symptom. Examples of additional active agents include, but are not limited to, an orexin receptor antagonist such as suvorexant (Belsomra®), supplements such as melatonin, valerian, 5-htp, magnesium or glycine; a benzodiazepine such as clonazepam (Klonopin®), diazepam (Valium®), chlorodiazepoxide (Librium®), flurazepam (Dalmine®); and/or a Z-drug such as zopiclone (Imovane®), zaleplon (Sonata®) and zolpidem (Ambien®).

Both the foregoing summary and the following description of the drawings and detailed description are exemplary and explanatory. They are intended to provide further details of the invention, but are not to be construed as limiting. Other objects, advantages, and novel features will be readily apparent to those skilled in the art from the following detailed description of the invention.

DESCRIPTION OF THE FIGURES

FIG. 2 shows that total hours of sleep increases as the dose of squalamine increases, and similarly total hours of sleep decreases as the dose of squalamine decreases.

FIGS. 11A and B show the diurnal rhythm in a normal individual over 16 days. The top panel shows an I-button tracing with a clear diurnal pattern and the bottom panel shows a periodogram with a clear peak.

FIGS. 12A and B show that a proper diurnal rhythm was established in a patient receiving treatment with squalamine. The top panel shows an I-button tracing that corresponds to the normal pattern seen in FIG. 11 and the bottom panel likewise shows a periodogram with a defined peak.

FIG. 13A shows a representative trace of a suction electrode multiunit recording. The insert in FIG. 13A shows extracellular action potential (40 µV) on a faster timebase (1 ms).

FIGS. 14A-14B show additional effects of squalamine in mice. FIG. 14A shows that intraluminal application of squalamine had no apparent effect on mouse colon migrating motor complex (MMC) peak pressure waves, although FIG. 14B shows that MMC propagation velocity from oral to anal was increased.

DETAILED DESCRIPTION OF THE INVENTION

Figure 1:
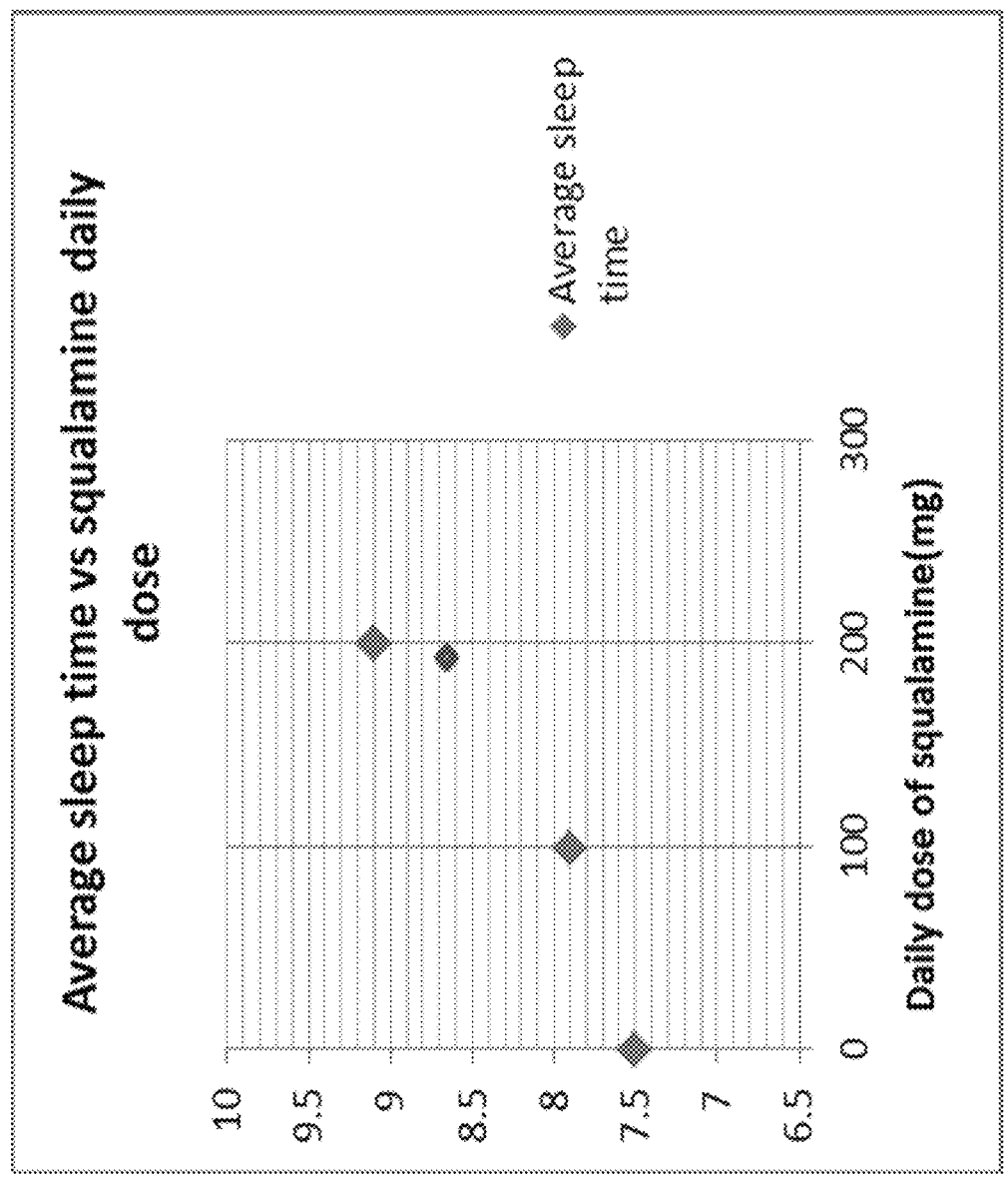
FIG. 1 shows a graph of average sleep time vs squalamine daily dose (mg). The graphical results show that average sleep time in an individual experiencing sleep disturbances is increased in a dose-dependent manner upon treatment with squalamine.

The present disclosure is directed to methods of treating and/or preventing sleep disorders, sleep disturbances and/or related symptoms in a subject in need thereof. Sleep disorders and disturbances in sleep are a common problem and can have a debilitating impact. Obtaining a good, restful sleep is necessary for optimal health, as lack of sufficient sleep can affect hormone levels, mood, weight, and various other physiological and psychological aspects. Surprisingly it was discovered that administration of at least one aminosterol or a pharmaceutically equivalent salt thereof can treat or prevent sleep disorders, sleep disturbances, and/or related symptoms. Any pharmaceutically acceptable method of administration can be used in the methods of the invention, although oral and intranasal administration, or a combination thereof, are preferred.

The methods of the invention comprise administering, e.g., orally or nasally, a therapeutically effective amount of one or more aminosterols or a pharmaceutically acceptable salt thereof to a subject in need. A "subject in need thereof" is a human or animal that is suffering from or at risk of suffering from a sleep disorder, sleep disturbance, or related symptom. By administering an aminosterol under conditions that provoke an Aminosterol-Induced central nervous system (CNS) response, sleep disorders, sleep disturbances, and related symptoms can be treated and/or prevented, resulting in prolonged, uninterrupted sleep.

Similarly, chronic administration of one or more aminosterols, or a pharmaceutically acceptable salt thereof, should prevent the development of sleep disorders, sleep disturbances, or related symptoms, particularly sleep disorders, sleep disturbances, and/or related symptoms associated with neurodegenerative conditions of the CNS. Examples of such neurodegenerative conditions and diseases are described herein and include, for example, Parkinson's disease, Alzheimer's disease, Huntington's chorea and/or Disease, schizophrenia, multiple sclerosis, dementia, degenerative processes associated with aging, dementia of aging, multi-system atrophy (MSA), fronto-temporal dementia, autism, progressive nuclear palsy, Guadeloupian Parkinsonism, spinocerebellar ataxia, Amyotorphic Lateral Sclerosis (ALS), Friedreich's ataxia, vascular dementia, Lewy Body dementia or disease, spinal muscular atrophy, supranuclear palsy, fronto temporal dementia, neuropathy of diabetes, peripheral sensory neuropathy, cerebral palsy, epilepsy, diabetic neuropathy, and depression.

The invention is also based on the discovery of unexpected and unprecedented activity of orally or nasally administered squalamine and related aminosterols (e.g., aminosterol 1436). The activity relates to stimulating a sequence of events within the human GI tract with therapeutic value. With respect to this activity, the sequence of events stimulated by an aminosterol such as squalamine or aminosterol 1436 involves the induction of an intestinal secretory response followed by a period of "small intestinal quieting," and the subsequent passage of a normally formed bowel movement. These events are best explained as a consequence of the stimulation of a heretofore unknown physiological gastrointestinal response, in this invention shown to be controlled or initiated by an effective oral dose of an aminosterol such as squalamine or the related aminosterol, 1436 (Aminosterol-Induced GI Response). The activity relates to stimulating the neural connections between the enteric nervous system and the brain with therapeutic value, which can thereby impact sleeping disorders, sleeping disturbances, or related symptoms, as described herein. With respect to this activity, the sequence of events stimulated by an aminosterol involves the entrainment of the circadian clock, the suprachiasmatic nucleus, and an improvement in the quality of sleep. These events are best explained as a consequence of the stimulation of a heretofore unknown physiological response of the hypothalamic and brain stem structures involved in setting the circadian rhythm and regulating the sleep-wake cycle.

Based on the pharmacology of the response, and the likely known components of the gastrointestinal tract that have been engaged, it is possible to predict uses or applications of the methods of the invention. These include (1) treatment of sleep disorders, such as delays in sleep onset, fragmentation of sleep, reduced REM sleep, reduced total sleep time, REM-behavior disorder, sleep breathing disorder including snoring and sleep apnea, hallucinations, narcolepsy, and day-time sleepiness.

The invention comprises orally or nasally administering a therapeutically effective amount of an aminosterol or pharmaceutically acceptable salt thereof, such as squalamine or a pharmaceutically acceptable salt or derivative thereof or aminosterol 1436 or a pharmaceutically acceptable salt or derivative thereof, to a subject, such as a mammal, in need. A "subject in need" is a human or mammal with a disorder in which the stimulation of the "Aminosterol-Induced GI Response" would provide therapeutic or medical benefit.

Preferably, the aminosterol is a pharmaceutical grade aminosterol. The composition can further comprise one or more pharmaceutically acceptable excipients. The aminosterol or pharmaceutically acceptable salt or derivative thereof is present in an amount sufficient to produce the intended benefit or response.

In another embodiment, the invention encompasses methods of treating and/or preventing conditions benefited by the stimulation of the Aminosterol-Induced GI Response comprising administering a therapeutically effective amount of an aminosterol that can inhibit the formation of actin stress fibers in endothelial cells stimulated by a ligand known to induce stress fiber formation. Compositions and aminosterols useful in the methods of the invention are described herein.

Optimized Aminosterol Dosing: In another embodiment, encompassed is a method of treating and/or preventing a sleep disorder, sleep disturbance, or related symptom comprising administering an aminosterol or a pharmaceutically acceptable salt or derivative thereof, wherein the method comprises determining a subject-specific dosage for the aminosterol or a pharmaceutically acceptable salt or derivative thereof. This aspect of the invention is directed to methods of treating sleep disorders, sleep disturbances, and related symptoms comprising the following steps: (i) identifying a starting dose of an aminosterol or a pharmaceutically acceptable salt or derivative thereof for a subject; (ii) administering an escalating dose of the aminosterol or a pharmaceutically acceptable salt or derivative thereof over a period of time until an effective aminosterol dose is identified, wherein the effective aminosterol dose is the dose where improvement or resolution of the sleep disorder or sleep disorder-related symptom is observed, and (iii) fixing the aminosterol dose at that level in that particular subject.

As described in Example 4, a study was conducted in patients with Parkinson's disease (PD). PD is a progressive neurodegenerative disorder caused by accumulation of the protein $\alpha$-synuclein ($\alpha$S) within the enteric nervous system (ENS), autonomic nerves and brain. While the study described herein assessed patients with PD, symptoms assessed and contemplated to be resolved by aminosterol treatment, such as sleep disorders and related symptoms, are not restored by the replacement of dopamine and are thus not unique to PD but rather common across a variety of disorders which involve impaired function of neural pathways, referred to herein as "brain-gut" disorders. Sleep disorders, sleep disruption, and related symptoms are encompassed by conditions not restored by the replacement of dopamine, as the sleep disorders, sleep disruption and related symptoms result from impaired function of neural pathways not restored by replacement of dopamine.

The methods and compositions disclosed herein permit exerting pharmacological control over the ENS in a manner that is without precedent in the literature. While the study described in Example 4 assessed the effectiveness of treating PD, it is contemplated that the effect of aminosterols on the ENS can broadly treat a variety of sleep disorders and sleep disorder-related symptoms.

Most surprisingly, as described in Example 4, it was discovered that aminosterol dosing is patient specific, as the dose is likely related to the extent of neuronal damage, with greater neuronal damage correlating with the need for a higher aminosterol dose to obtain a desired therapeutic result. This was not known prior to the present invention. Thus, one aspect of the present invention is directed to methods of treating sleep disorders or related symptoms in a subject, where the method comprises determining an effective therapeutic aminosterol dose for the subject. In addition, it was also surprisingly discovered that the starting aminosterol dose is dependent upon the severity of the symptom. Specifically, if the symptom is severe, then the starting aminosterol dose, prior to dose escalation, should be higher than if the symptom is moderate. A "severe" sleep disorder, sleep disturbance or symptom can be defined as one which results in a subject obtaining less than about 50% of the hours of sleep recommended by a medical authority for the age group of the subject.

One impact of the present invention is that recognizing that an aminosterol dose useful in treating sleep disorders or related symptoms is patient specific can prevent the use of incorrect aminosterol doses for patients. This is a significant discovery, as if a subject is put on an aminosterol dose that is too high, then resultant nausea, vomiting, and abdominal discomfort can result in the patient going off the drug, with the sleep disorder, sleep disturbance, or related symptom remaining untreated. Similarly, if a subject is put on an aminosterol dose that is too low, then the sleep disorder, sleep disturbance, or related symptom will not be successfully treated. Prior to the present invention, there was no recognition that aminosterol doses useful in treating various conditions had no relation to the sex, age, weight, ethnicity, or other similar patient characteristics. This is unexpected, as it is contrary to dosing strategies for almost all other medications.

Not to be bound by theory, it is believed that aminosterols target neurotoxic aggregates of αS in the gastrointestinal tract, and restore function of the enteric nerve cells. The now-functional enteric nerve cells prevent retrograde trafficking of proteins, such as alpha-synuclein, to the brain, resulting in restoring gastrointestinal function as well as treating and/or preventing sleep disorders, sleep disturbances, or related symptoms.

As a result of the normal trafficking of αS aggregates from the ENS to the central nervous system (CNS) via afferent nerves such as the vagus (Holmqvist et al. 2014; Svensson et al. 2015), neurotoxic aggregates accumulate progressively within the brainstem and more rostral structures. Inhibiting αS aggregation in the ENS may, thus, reduce the continuing neuro disease process in both the ENS and CNS (Phillips et al. 2008), thereby treating the sleep disorder, sleep disruption, or related symptom caused by the αS aggregation in the ENS. This relationship between the ENS and CNS is sometimes described herein as "brain-gut" in relation to a class of disorders or the axis of aminosterol activity.

Not to be bound by theory, based on the data described herein, it is believed that aminosterols inhibit αS aggregation in the ENS by either acting locally when administered orally or intranasally, as supported by the oral bioavailability <0.3%. An orally administered aminosterol such as squalamine, the active ion of ENT-01, stimulates gastro-intestinal motility in mice with constipation due to overexpression of human αS (West et al, manuscript in preparation). Perfusion of an aminosterol such as squalamine through the lumen of an isolated segment of the bowel from the PD mouse model results in excitation of IPANs (intrinsic primary afferent neuron), the major sensory neurons of the ENS that communicate with the myenteric plexus, increasing the frequency of propulsive peristaltic contractions and augmenting neural signals projecting to the afferent arm of the vagus.

Systemic absorption of the aminosterol following oral administration was negligible both in this study and in prior studies involving mice, rats and dogs. Prior studies demonstrated that intravenous administration of squalamine was not associated with increased gastrointestinal motility, despite reaching systemic blood levels one thousand-fold greater than that achieved by orally administered squalamine. These data suggest that the aminosterol effect is mediated by local action. The topical action would also explain why adverse events in Example 4 were largely confined to the gastrointestinal tract.

Several exploratory endpoints were incorporated into the trial described in Example 4 to evaluate the impact of an aminosterol on neurologic symptoms associated with a neurodisease such as PD. Following aminosterol treatment, the Unified Parkinson's Disease Rating Scale (UPDRS) score, a global assessment of motor and non-motor symptoms, showed significant improvement. In particular, constipation, which was used as a marker for measuring impact and effectiveness of the aminosterol on the tested patient population, showed dramatic improvement. Interestingly, most indices related to bowel function returned to baseline value by the end of the 2-week wash-out period, i.e., in the absence of study drug, while improvement in the CNS symptoms persisted. The rapid improvement in certain CNS symptoms is consistent with a mechanism whereby nerve impulses initiated from the ENS following aminosterol administration augment afferent neural signaling to the CNS. This may stimulate the clearance of αS aggregates within the afferent neurons themselves as well as the secondary and tertiary neurons projecting rostrally within the CNS, since it is known that neural stimulation is accompanied by increased neuronal autophagic activity (Shehata et al. 2012). It is believed that after cessation of aminosterol administration, the neurons of the CNS gradually re-accumulate an αS burden either locally or via trafficking from αS re-aggregation within the gut.

Low bioavailability: As described in Example 4, in preclinical studies, squalamine (ENT-01) exhibited an oral bioavailability of about 0.1% in both rats and dogs. In Stage 1 of the phase 2 study, oral dosing up to 200 mg (114 mg/m$^2$) yielded an approximate oral bioavailability of about 0.1%, based on a comparison of a pharmacokinetic data of the oral dosing and the pharmacokinetic data measured during prior phase 1 studies of IV administration of squalamine.

In one embodiment of the disclosed methods, following aminosterol administration (e.g., oral or intranasal) there is essentially no detectable levels of the administered aminosterol in the bloodstream of the subject. In another embodiment, following oral administration there is preferably less than about 10 ng/ml of the administered aminosterol in the bloodstream of the subject, measured between about 1 to about 12 hours following oral administration. In other embodiments, following oral or intranasal administration there is less than about 9, less than about 8, less than about 7, less than about 6, less than about 5, less than about 4, less than about 3, less than about 2, or less than about 1 ng/ml in the bloodstream of the subject measured from about 1 to about 12 hours following oral administration. In another embodiment, aminosterol administration (e.g., oral or intranasal) results in a bioavailability of less than about 3%, less than about 2.5%, less than about 2%, less than about 1.5%, less than about 1%, less than about 0.9%, less than about 0.8%, less than about 0.7%, less than about 0.6%, less than about 0.5%, less than about 0.4%, less than about 0.3%, less than about 0.2%, or about 0.1% or less, within about 1 to about 12 hours following administration.

I. Overview Regarding Sleep Disorders

Normal sleep is critically important for the proper functioning of many organ systems, the most important of which is the brain. Disturbances in normal sleep patterns are closely associated with the normal aging process, with the development of cognitive impairment, with impaired memory deposition and consolidation and with the occurrence of neurodevelopmental, neuroaffective and neurodegenerative disorders. The alternating pattern of sleep and wakefulness occurring every 24 hours is known as the circadian rhythm. The rhythm is set by the "zeitgeber" (time setter), an entity known as the suprachiasmatic nucleus (SCN) and located in the hypothalamus. The SCN is normally "entrained" or synchronized by the external light-dark cycle. This relationship between external light and dark and the sleep wake cycle synchronized to it by the SCN can be over ridden during periods of hunger by neural signals emanating in the gut and relayed to the hypothalamus. Under adverse circumstances such as periods of extreme hunger or starvation, this process of over-riding of the circadian clock enables the person or animal to remain awake and find food, i.e., to fulfill its energy requirements. The circadian sleep-wake cycle can also shift in response to changes in external light-dark cycles, such as the desynchronization that occurs during travel from one time zone to another (jet-lag). Under such circumstances, a progressive adjustment occurs until the SCN is resynchronized with the external light-dark cycle. A similar "phase-shift" and adjustment occurs in night-shift workers.

Under normal circumstances, the properly functioning SCN, synchronized to the external light-dark cycle and to neural signals emanating from the enteric nervous system, will regulate the sleep-wake cycle by sending neural and chemical signals to the surrounding structures and to portions of the brain stem involved in sleep and wakefulness. An individual with a properly functioning hypothalamus and brain stem will go to bed and fall asleep within minutes, remain asleep throughout the night, wake up in the morning and remain awake and alert throughout the day. During the night, the asleep individual will experience several cycles of sleep, beginning with light sleep, progressing through rapid eye movement sleep (REM-sleep) to deep sleep and back. Each complete sleep period lasts about 90 minutes. Periods of REM-sleep are closely associated with dreaming. During REM-sleep, neural signals emanating from certain parts of the brain stem ensure that skeletal muscles become "atonic" or are paralyzed, such that the individual cannot "act out" their dreams.

Certain diseases and conditions may impair the normal functioning of the "zeitgebber" or circadian clock. These conditions may be reversible, such as desynchronization resulting from jet-lag, night-shift work or hunger, conditions easily remedied by adaptation or food intake. In contrast, damage to the nerves carrying light-dark related information from the retina to the SCN (conditions which may lead to blindness), or damage to the enteric nerves and neural structures which relay messages from the intestine to the SCN (conditions which may lead to neurodegenerative disorders) can cause permanent dysfunction of the circadian rhythm and abnormal sleep behavior.

Dysfunction of the circadian rhythm manifests first and foremost by abnormal sleep patterns. Such abnormalities typically are mild at onset and worsen progressively over time. A common symptom of sleep disorder is a delay in the onset of sleep. This delay can be as long as several hours, and the individual may not be able to fall asleep until the early hours of the morning. Another common symptom is sleep fragmentation, meaning that the individual awakens several times during the course of the night. Once awakened, the individual may not be able to get back to sleep, and each awake fragment may last an hour or more, further reducing "total sleep time," which is calculated by subtracting total time of the awake fragments from total time spent in bed. Total sleep time also diminishes with age, from about 14 to about 16 hours a day in newborns, to about 12 hours by one year of age, to about 7 to about 8 hours in young adults, progressively declining to about 5 to about 6 hours in elderly individuals. Total sleep time can be used to calculate an individual's "sleep age" and to compare it to their chronologic age. Significant discrepancies between sleep age and chronologic age are a reflection of the severity of the sleep disorder. "Sleep efficiency," defined as the percentage of the time spent in bed asleep is another index that can be used to determine the severity of the sleep disorder. Sleep efficiency is said to be abnormal when the percentage is below 70%.

Individuals with severe sleep disorders also typically suffer from day-time sleepiness. This can manifest as day-time "napping" for an hour or two, to "dosing off" for a few minutes during a film or to "micro-sleep" episodes lasting seconds to minutes, and of which the individual may or may not be aware. Narcolepsy is a rare and extreme form of day-time sleepiness, with the sudden onset of sleep causing the individual to fall down. Another form of sleep disturbance involves periods of loud snoring alternating with periods of "sleep apnea" (arrested breathing), a condition known as "sleep-disordered breathing." "REM-behavior disorder" or RBD, is yet another sleep disturbance which occurs as a result of dysfunctional neural communication between the enteric nervous system, structures responsible for sleep in the brain stem and the SCN. In individuals with RBD, neural signaling which causes the paralysis (atonia) of muscles under voluntary control is impaired or altogether absent. As a consequence, "acting-out" of dreams occurs. This can range at one end of the spectrum from an increase in muscle tone detectable by electromyography (EMG) and accompanied by small movements of the hands and feet during REM sleep, to violent thrashing of arms and legs, kicking or punching a bed partner, speaking out loud or screaming, at the other end of the spectrum. In some cases, the individual suffering from RBD can leap out of bed to escape or attack the enemy in the dream, frequently knocking over objects, and sometimes hitting an object and sustaining a head injury. Alternatively, the individual might grab the head of a bed partner as if it were a ball, hurting them in the process. Episodes of RBD can occur several times a night or very infrequently, once every few months. They can also be clustered, several occurring within a week, followed by periods of normal sleep. Unless the condition can be treated with a medication that restores normal functioning of the circadian rhythm and improves sleep patterns, individuals with RBD progress to neurodegenerative disorders.

Sleep disorders, sleep disturbances and related symptoms are very commonly associated with dysfunction of the enteric nervous system (ENS). As a result of the dysfunction of the enteric nerves, motility is impaired and the individual typically suffers from constipation. Furthermore, as a consequence of the pathology in the ENS, neural signaling between the ENS, the brain stem and the SCN is impaired and normal sleep behavior is disturbed. Untreated, the pathologic process which begins in the ENS extends via the neural connections to the brain stem and hypothalamus. There is thus a need for a treatment which restores the proper function of the ENS, improving gut motility, overcoming constipation and which simultaneously improves neural signaling from ENS to brainstem and SCN, restoring the circadian rhythm and normal sleep behavior.

Sleep disorders, sleep disturbances and related symptoms are also associated with olfactory dysfunction. Many if not most individuals with sleep disorders have an impaired or absent sense of smell. As a consequence of the pathology in the olfactory system, neural signaling between the olfactory system and SCN is disturbed. As is the case for motility disorders emanating from the ENS, the pathologic process that begins in the olfactory system causing loss of smell spreads progressively to the basal forebrain, the hypothalamus and the brain stem, resulting in a sleep disorder. There is thus a need for a treatment which restores the proper function of the olfactory system, improving the sense of smell, and which simultaneously improves neural signaling from the olfactory system to the SCN, restoring the circadian rhythm and normal sleep behavior.

Sleep disorders, sleep disturbances and related symptoms are also closely associated with blunting of diurnal temperature oscillations. In a normally functioning individual, vasomotor changes regulated by the hypothalamus modify distal extremity temperature, allowing it to rise to 34-36° C. at night, to remain high during the night, then to fall to 28-30° C. in the early morning hours and to remain low throughout the day. The heat loss that ensues from the rise in extremity temperature leads to a corresponding but somewhat delayed fall in core body temperature (CBT). About one hour after hand temperature peaks, CBT is reduced by 1° C. Sleep onset is closely linked to this nadir in CBT. The reverse happens in the morning, with CBT rising by a degree about an hour after hand temperature reaches its nadir and the individual awakens. As long as hand temperature remains low, the individual stays awake. Hand temperature is thus a close indicator of the sleep-wake state and can be used as a surrogate measure to determine when sleep occurs. In individuals with sleep disorders, diurnal oscillations in skin temperature are blunted or even absent. Hand temperature doesn't rise in the evening hours and sleep onset is delayed. During the night, it may fall below 34° C. and the individual then awakens and remains awake until it rises again. Repeated falls in hand temperature are paralleled by repeated awakenings or fragmented sleep. Contrarily, during the day, hand temperature fails to remain low, rising above a threshold intermittently. The individual with a sleep disorder correspondingly experiences day-time sleepiness. Fluctuation in skin temperature is thus a reliable marker of circadian physiology and it has been validated as a surrogate to polysomnography to assess disturbances of sleep. It can be monitored non-invasively, continuously, in a home setting and at very low cost using validated temperature sensors. Examples of normal and abnormal diurnal temperature patterns are shown in FIGS. 9 and 10 (normal) and 8 (abnormal).

The neurologic structures involved in the induction and maintenance of sleep and in arousal and maintenance of wakefulness are concentrated in the hypothalamus and brain stem. While the SCN is responsible for setting the circadian rhythm, the pre-optic nuclei are responsible for sleep onset and sleep maintenance (MnPO and VLPO respectively). The pedunculopontine nucleus (PPN) in the brain stem is responsible for oscillations between REM and non-REM sleep and the raphe nuclei and the reticular activating system (RAS) regulate arousal. All these structures receive input from the SCN and the pre-optic nuclei in the hypothalamus and basal forebrain. The firing rate of each of these structures is state-specific. Structures involved in wakefulness such as the RAS fire fastest during wakefulness, slow down during non-REM sleep, and nearly stop firing during REM sleep. The suppression of motor activity during normal REM sleep (atonia) is the result of multiple interacting inhibitory pathways emanating from a region known as subcoeruleus and terminating on spinal motor neurons. Changes in neuronal firing rates in relevant centers in turn influence the secretion of hypothalamic proteins such as hypocretins that also affect sleep-wake cycles and muscle tone. Many or all of these structures are dysfunctional in individuals with sleep disorders.

Sleep disorders, sleep disturbances and related symptoms are not only a consequence of pathologic processes that begin in the ENS or in the olfactory system but they may actively contribute to the progression of such pathologic processes. The pathologic protein (a-beta) associated with plaques found in Alzheimer's disease (AD) for example, may be cleared from the brain during normal sleep, and sleep disorders may interfere with its nocturnal clearance. Even small alterations in brain a-beta levels could significantly increase plaque pathology over a long timeframe, setting in motion a cycle in which progression of a-beta pathology further impairs the sleep disorder. The same vicious cycle may be true in Parkinson's disease (PD) in which the concentration of the pathologic, pro-inflammatory protein alpha-synuclein rises in the presence of a sleep disorder. Individuals with AD or PD and a sleep disorder are much more likely to develop dementia than individuals with the same disease but without the sleep disorder. Sleep disorders tend to occur long before a diagnosis of PD or AD, so the possibility exists that treating a sleep disorder before the neurodegenerative pathology develops might actually prevent or at the very least slow the development or onset of the disease. Sleep disturbances and related symptoms are also common in individuals with schizophrenia and the worsening of the sleep disturbance can predict the occurrence of psychotic episodes.

There are currently no satisfactory treatments for sleep disorders, sleep disturbances, or related symptoms associated with circadian dysfunction. Further, there are no known "cures" for sleep disorders, sleep disturbances, and related symptoms for many of the conditions described herein. The first line of treatment, clonazepam, is useful in inducing sleep in individuals with sleep disorders and sleep disturbances, and it may also alleviate symptoms of RBD but it does nothing to restore circadian rhythmicity. Its effect tends to wear off with continued use and because of its long duration of action, it may also worsen cognitive function and motor performance in the morning. It may also worsen sleep apnea because of its tendency to suppress brain stem neuronal activity. Polysomnographic features of RBD are not usually suppressed by clonazepam. Melatonin, a hormone secreted by the pineal gland, may be preferable to clonazepam because it can help restore circadian rhythmicity and can suppress RBD without the side-effects associated with clonazepam. It is also preferable to clonazepam because it is less sedating. However, melatonin does little to induce sleep in many of patients. Recently, melatonin receptor agonists rameleton and tasimelteon were approved for the treatment of circadian disturbance in the blind. Other drugs which have been tried in RBD with variable success include benzodiazepines, pramipexole, donepezil, levodopa, carbamazepine, triazolam, sodium oxybate, quetiapine and Nuplazid. The ideal medication for sleep disorders in this patient population would aim to improve sleep quality as well as normalizing circadian rhythmicity by directly targeting the circadian clock.

The present invention is directed to the novel discovery that administration of an aminosterol can normalize circadian rhythmicity and have considerable beneficial effect on quality of sleep. Further, administration of an aminosterol or a pharmaceutically acceptable salt or derivative thereof can treat and/or prevent many sleep disorders, sleep disturbances, and related symptoms.

II. Methods of Treating and/or Preventing Sleep Disorders, Sleep Disturbances and Related Symptoms As disclosed above, the present methods are useful for treating and/or preventing a variety of sleep disorders, sleep disturbances, and related symptoms. For the purposes of this disclosure, a subject is treated if one or more beneficial or desired results, including desirable clinical results, are obtained. For example, beneficial or desired clinical results include, but are not limited to, one or more of the following: a change in the length of sleep, sleeping at night rather than during the day, a decrease in the number of awakenings during the night, falling asleep more quickly, less thrashing or limb movement, and/or developing a normal Circadian (i.e., diurnal) rhythm.

Sleep disorders, sleep disturbances, and related symptoms that can be treated and/or prevented according to the methods described herein are described throughout the application. Examples include but are not limited to: (a) sleep disorders, sleep disturbances, and related symptoms that comprise a dyssomnia, parasomnia, and/or circadian rhythm sleep disorder; (b) sleep disorders, sleep disturbances, and related symptoms that comprise a loss of diurnal rhythm (Circadian rhythm), wherein the aminosterol composition can reverse the dysfunction caused by the sleep disorder, disturbance or related symptom and treats, prevents, improves, and/or resolves the sleep disorder, disturbance or related symptom; (c) sleep disorders, sleep disturbances, and related symptoms comprising a delay in sleep onset, sleep fragmentation, REM-behavior disorder (RBD), sleep-disordered breathing including snoring and apnea, day-time sleepiness, micro-sleep episodes, narcolepsy, hallucinations, hypersomnia, Restless leg syndrome (RLS), Periodic limb movement disorder (PLMD), insomnia, gastrointestinal distress, headache, narcolepsy, REM disturbed sleep, clinical or sub-clinical "sleep attacks", thrashing or limb movement during sleep period, nonrestorative sleep, awakenings during sleep period, cognitive impairment, sleep problems, poor psychomotor coordination, bruxism, catathrenia, cataplexy, sleep walking, Delayed sleep phase disorder (DSPD), advanced sleep phase disorder (ASPD), non-24-hour sleep-wake disorder (non-24) in the sighted or in the blind, irregular sleep wake rhythm, Shift work sleep disorder (SWSD), Hypopnea syndrome, Idiopathic hypersomnia, Kleine-Levin syndrome, sleep terror disorder, nocturia, sleep paralysis, somniphobia, or any combination thereof; and/or (d) sleep disorders, sleep disturbances, and related symptoms comprising or associated with a neurodegenerative disorder or disease.

A. Summary of Example Data

Figure 22:
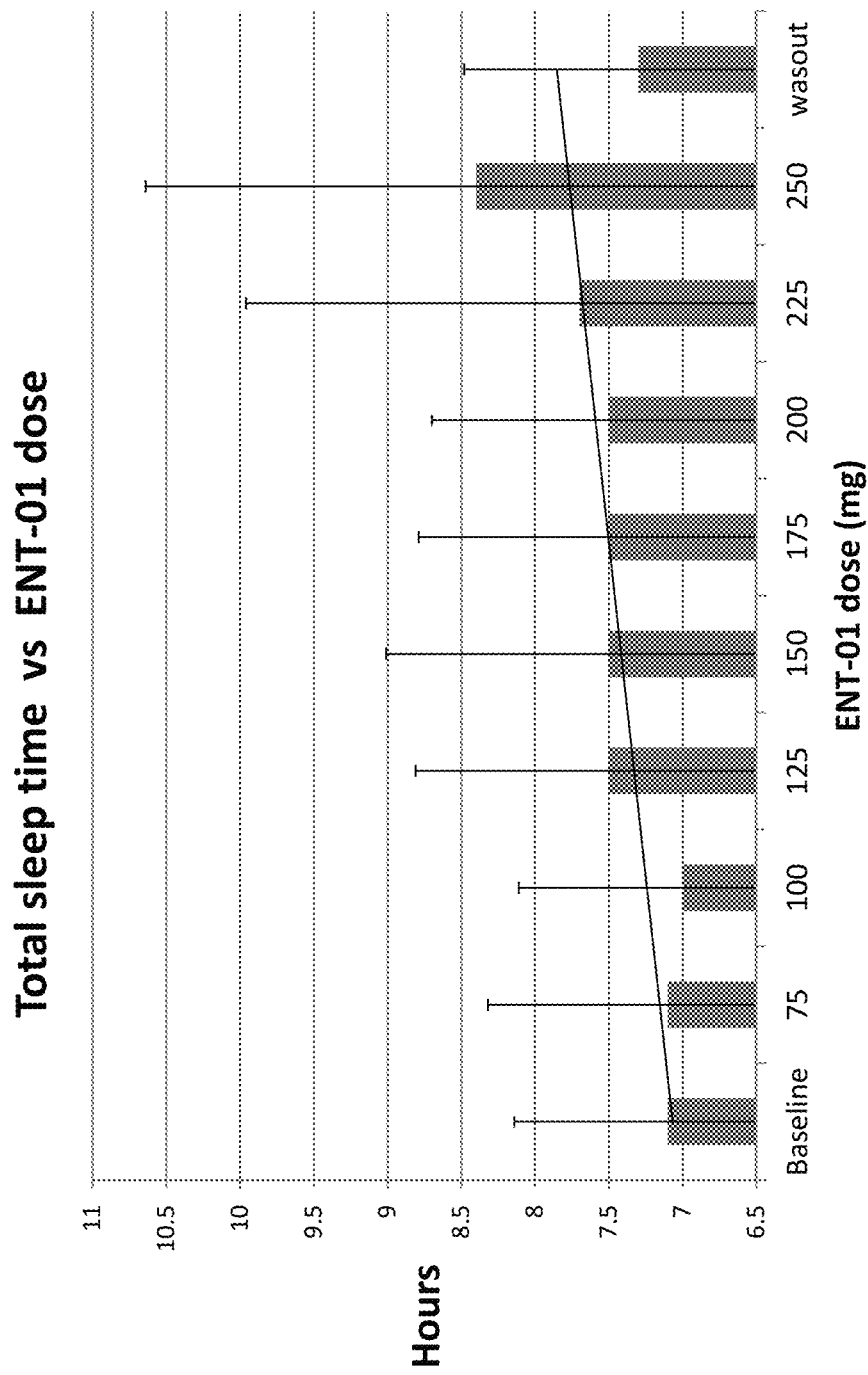
FIG. 22 shows total sleep time vs the dose of squalamine (ENT-01), with total sleep time increasing progressively from baseline to 250 mg.
Figure 23:
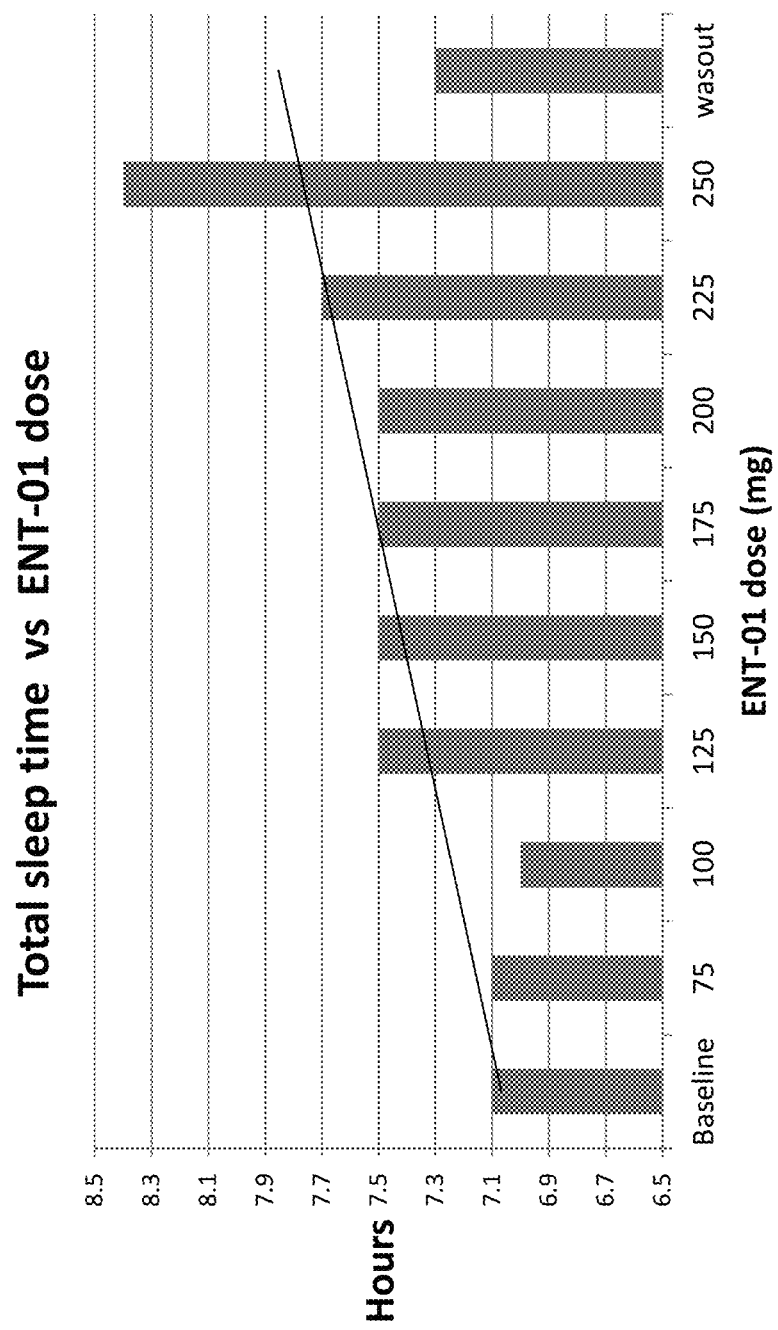
FIG. 23 shows total sleep time vs the dose of squalamine (ENT-01), with total sleep time increasing progressively from baseline to 250 mg.

Data detailed in the Examples demonstrates successful application of the methods of the invention. For example, the results of Example 4 shows improvement following aminosterol treatment of PD subjects in REM-behavior disorder (RBD) and sleep. Six of the patients enrolled had daily hallucinations or delusions and these improved or disappeared during treatment in five. In one patient the hallucinations disappeared at 100 mg, despite not having reached the colonic prokinetic dose (e.g., fixed escalated aminosterol dose) of 175 mg for this particular patient. The patient remained free of hallucinations for 1 month following cessation of dosing. RBD and total sleep time also improved progressively in a dose-dependent manner. In particular, FIGS. 22 and 23 show that total sleep time increased progressively from 7.1 hours at baseline to 8.4 hours at 250 mg and was consistently higher than baseline beyond 125 mg.

Disturbance of the circadian rhythm has been described in neurodiseases such as PD both clinically and in animal models and might play a role in the abnormal sleep architecture, dementia, mood and autonomic dysfunction associated with neurodiseases such as PD (Breen et al. 2014; Videnovic et al. 2017; Antonio-Rubio et al. 2015; Madrid-Navarro et al. 2018). In Example 4, circadian rhythm was monitored through the use of a temperature sensor that continuously captured wrist skin temperature (Sarabia et al. 2008), an objective measure of the autonomic regulation of vascular perfusion (Videnovic et al. 2017). Circadian cycles of wrist skin temperature have been shown to correlate with sleep wake cycles, reflecting the impact of nocturnal heat dissipation from the skin on the decrease in core temperature and the onset of sleep (Sarabia et al. 2008; Ortiz-Tuleda et al. 2014). Oral administration of ENT-01 detailed in Example 4 had a significant positive impact on the circadian rhythm of skin temperature in the 12 patients with evaluable data. Not to be bound by theory, it is believed that aminosterols could be affecting neuronal circuits involving the master clock (the suprachiasmatic nucleus) and its autonomic projections and opens the possibility of therapeutic correction of circadian dysfunction.

Further, as described in Example 4, aminosterol dosing is patient specific, as the dose is likely related to the extent of neuronal damage, with greater neuronal damage correlating with the need for a higher aminosterol dose to obtain a desired therapeutic result. As described in greater detail herein, aminosterol dosing can range from about 0.01 to about 500 mg/day, with dosage determination as described herein.

Example 4 describes several tools used to measure and evaluate the effect of aminosterol treatment on sleep, including for example:

(1) Sleep Diary (participants completed a sleep diary on a daily basis throughout the study. The diaries included time into bed and estimated time to sleep as well as wake time and duration during the night.);

(2) I-Button Temperature Assessment. The I-Button is a small, rugged self-sufficient system that measures temperature and records the results in a protected memory section. The Thermochron I-Button DS1921H (Maxim Integrated, Dallas, Tex.) was used for skin temperature measurement. I-Buttons were programmed to sample every 10 mins., and attached to a double-sided cotton sport wrist band using Velcro, with the sensor face of the I-Button placed over the inside of the wrist, on the radial artery of the dominant hand. Subjects removed and replaced the data logger when necessary (i.e., to have a bath or shower). The value of skin temperature assessment in sleep research is that the endogenous skin warming resulting from increased skin blood flow is functionally linked to sleep propensity. From the collected data, the mesor, amplitude, acrophase (time of peak temperature), Rayleight test (an index of interdaily stability), mean waveforms are calculated);

(3) Unified Parkinson's Disease Rating Scale (UPDRS), sections 1.7 (sleep problems), 1.8 (daytime sleepiness) and 1.13 (fatigue);

(4) Parkinson's Disease Fatigue Scale (PFS-16);

(5) REM Sleep Behavior Disorder Screening Questionnaire; and (6) Parkinson's Disease Sleep Scale.

Figure 19:
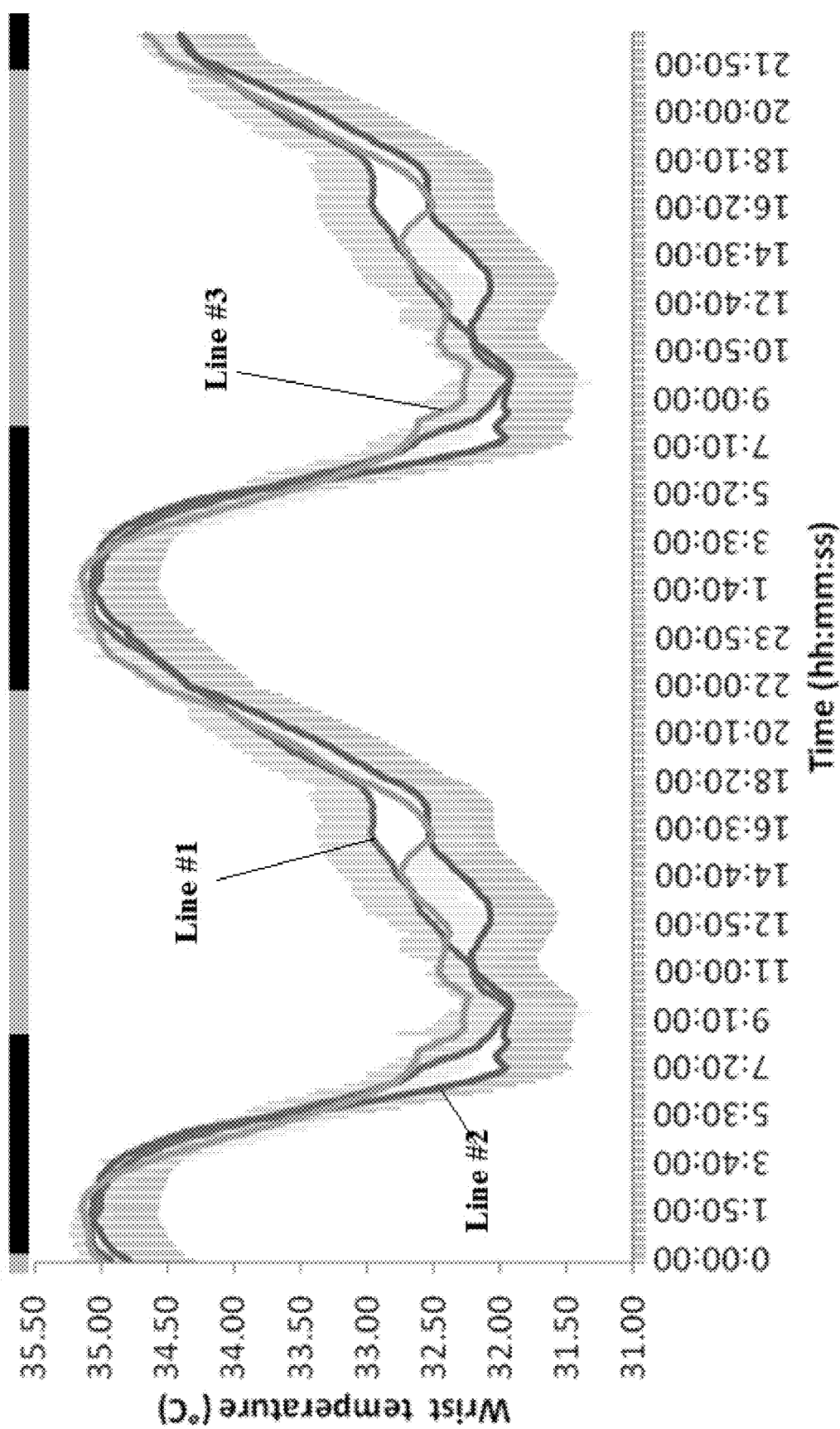
FIG. 19 shows the effect of squalamine (ENT-01) on circadian rhythm. The figure depicts the mean waveform of temperature under three conditions per patient: baseline (Line #1), treatment with highest drug dose (Line #2), and washout (Line #3). Each mean waveform is double plotted for better visualization. Low temperatures indicate higher activation, while higher values are associated with drowsiness and sleepiness. The top black bar indicates a standard rest period from 23:00 to 07:00 h.
Figure 20A:
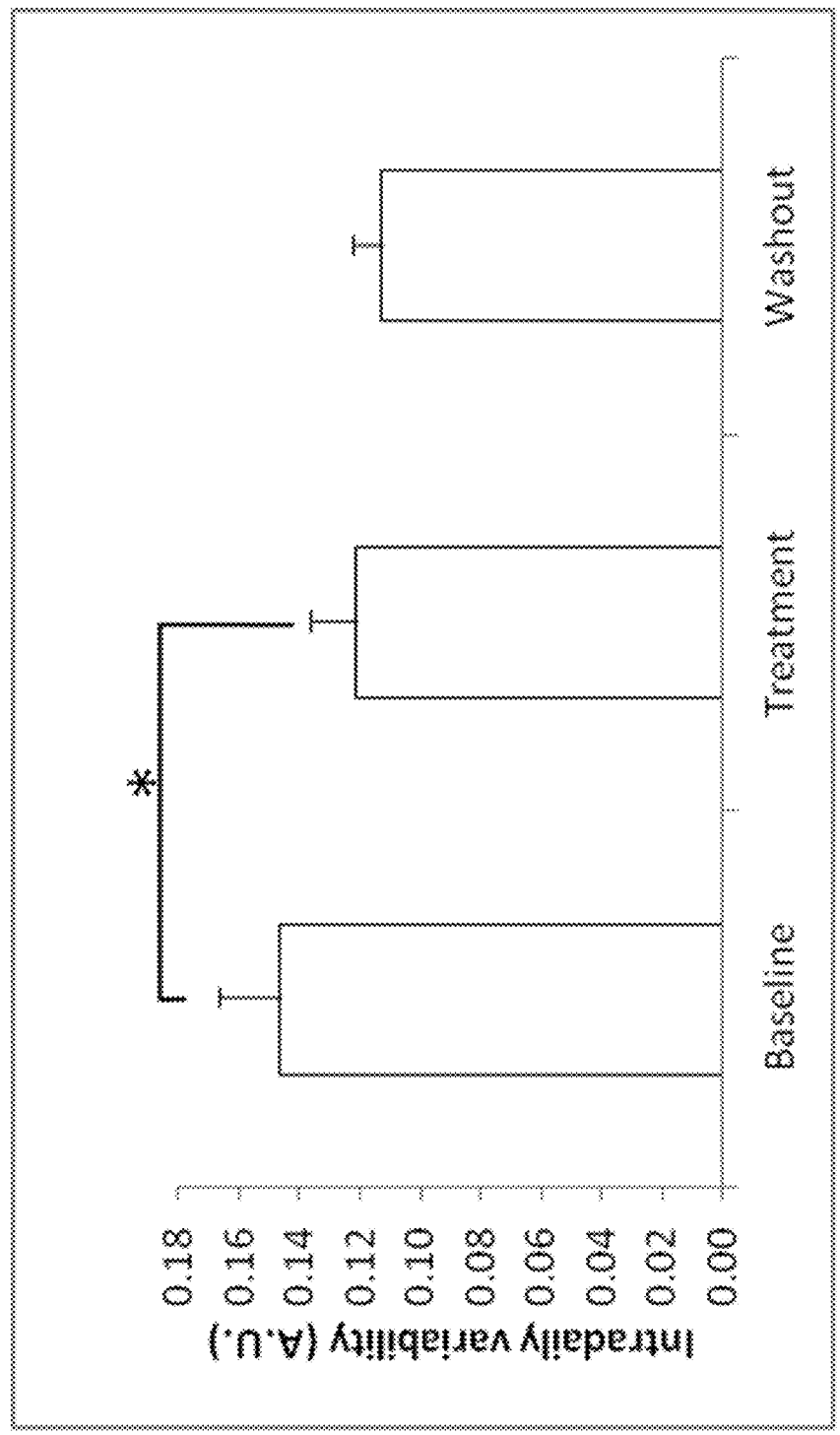
FIGS. 20A-F show the effect of squalamine (ENT-01) on circadian rhythm. The figures depict the results of circadian non-parametric analysis of wrist skin temperature rhythm throughout each condition (baseline, treatment with highest dose of squalamine (ENT-01) and washout). The following parameters were measured: Inter-daily variability (FIG. 20A), inter-daily stability (IS) (FIG. 20B), relative amplitude (RA) (FIG. 20C), circadian function index (FIG. 20D), M5V (FIG. 20E), which refers to the five consecutive hours with the highest temperature or high somnolence, and L10V (FIG. 20F), which indicates the mean of the ten consecutive hours with lowest temperature or high activation. The circadian function index (CFI) is an integrated score that that takes into account RA, IS, and IV values and ranges from 0 (absence of circadian rhythm) to 1 (robust circadian rhythm). Each parameter is representative of a complementary dimension of temperature circadian rhythm. Interdaily stability (IS) values are considered as a measure of the rhythm regularity over consecutive days. The intradaily variability (IV), indicates the degree of rhythm fragmentation, which is frequently associated with aging and metabolic and neurodegenerative diseases. Relative amplitude (RA) is an index of the rhythm's robustness. M5V refers to the five consecutive hours with the highest temperature, while L10V, indicates the mean of the ten consecutive hours with lowest temperature. Student's paired t-test, *p<0.05, p<01, *p<0.001.Values expressed as mean±SEM (n=12 in each condition).
Figure 20B:
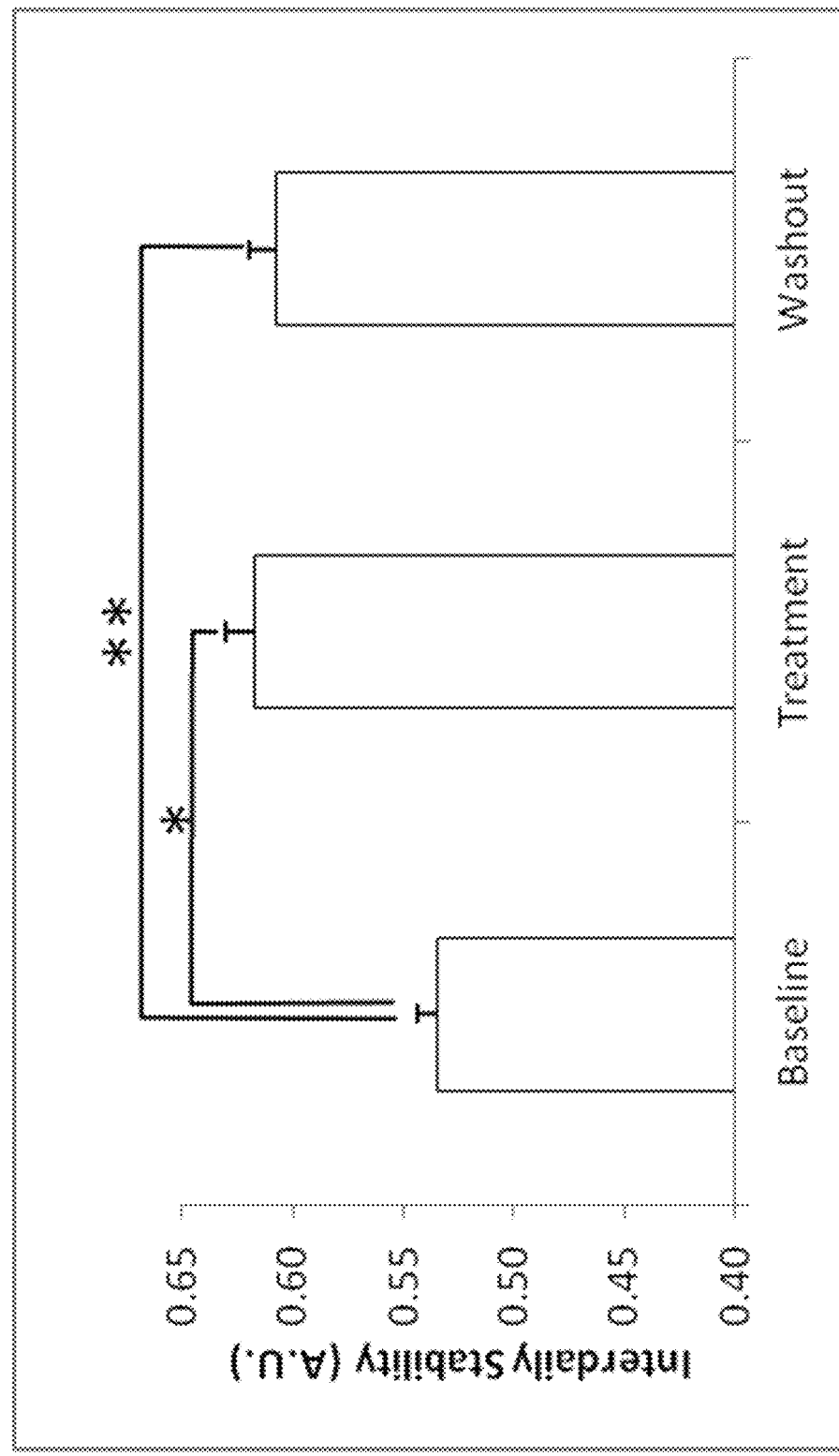
Figure 20C:
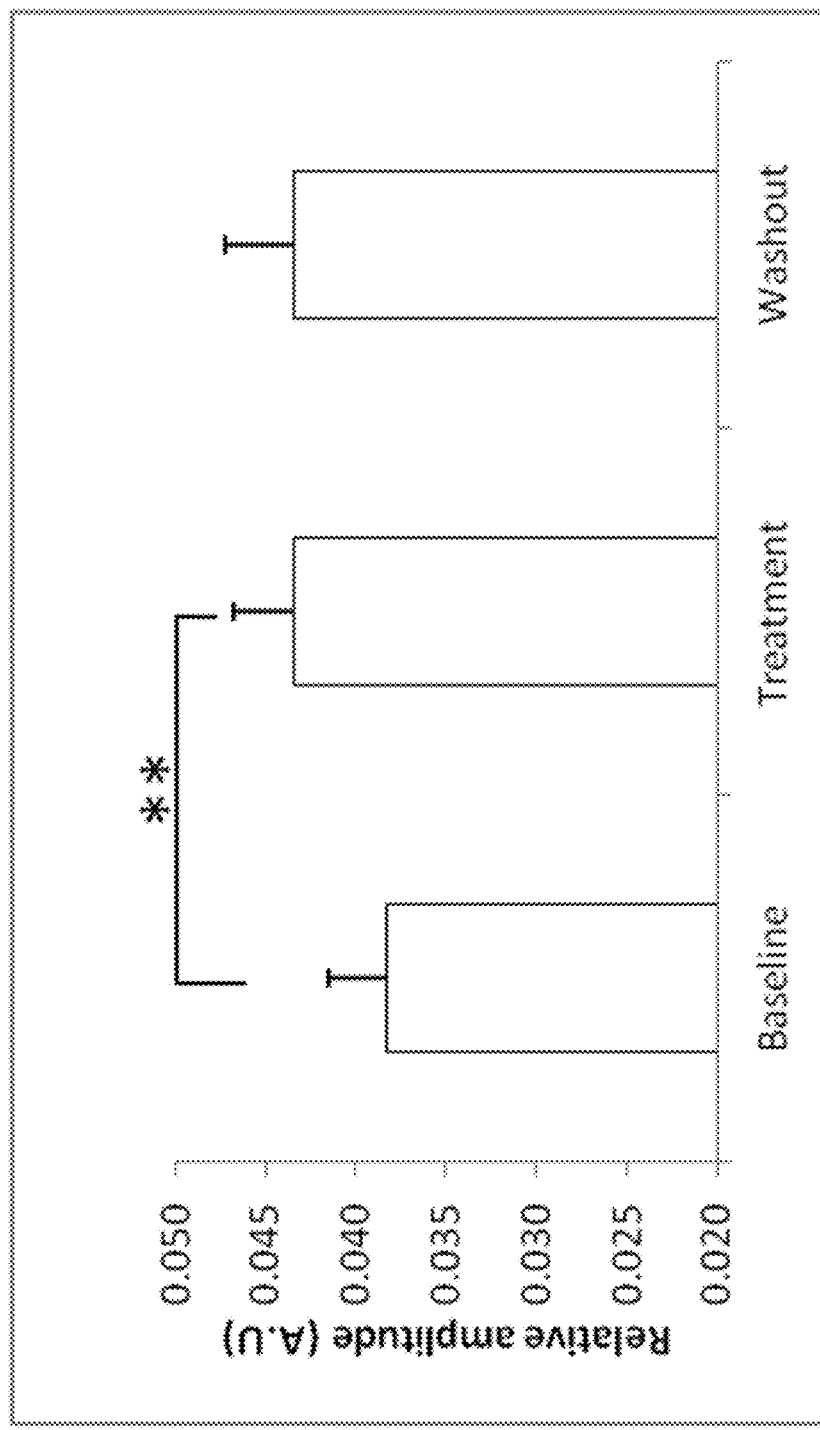
Figure 20D:
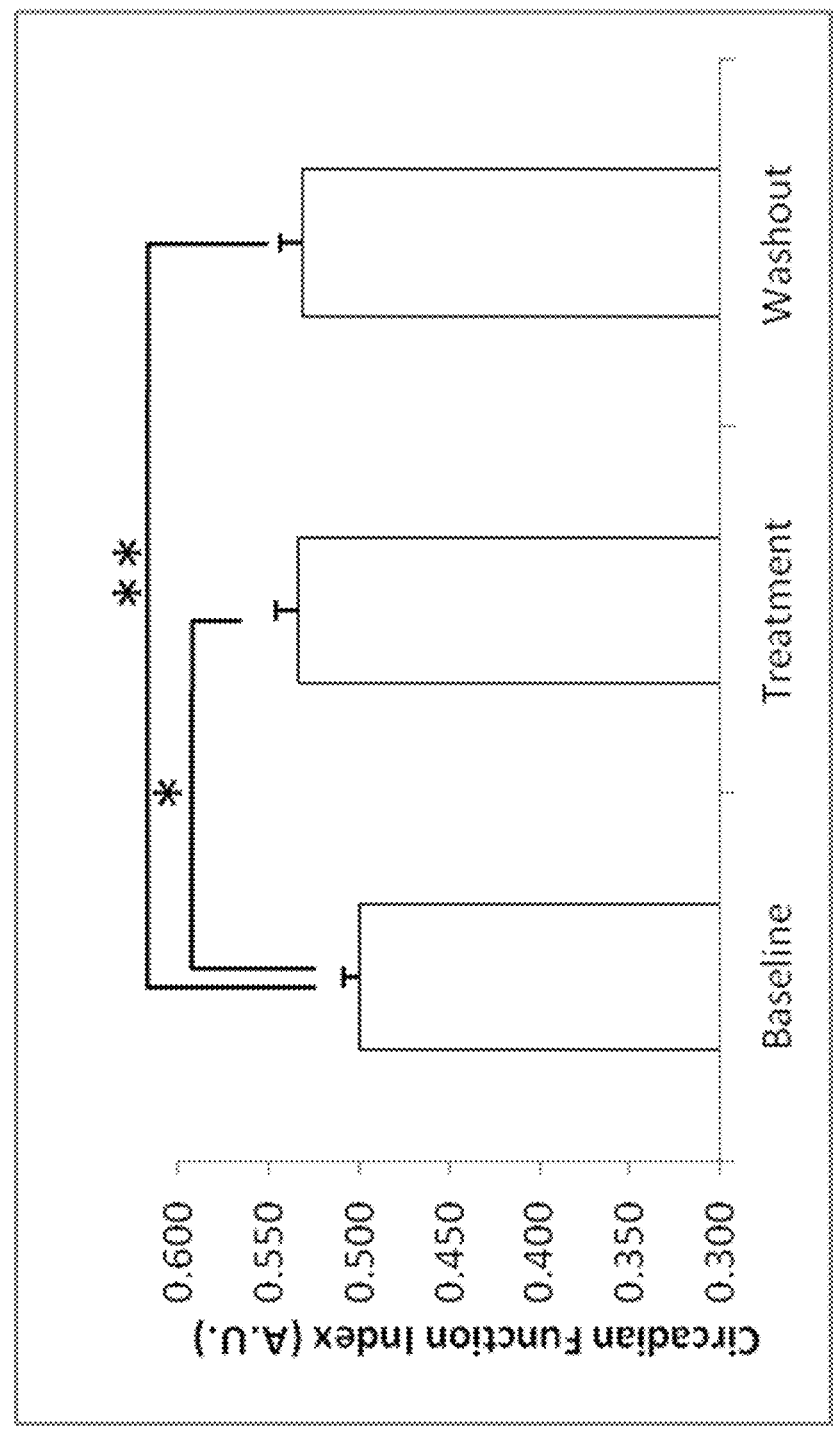
Figure 20E:
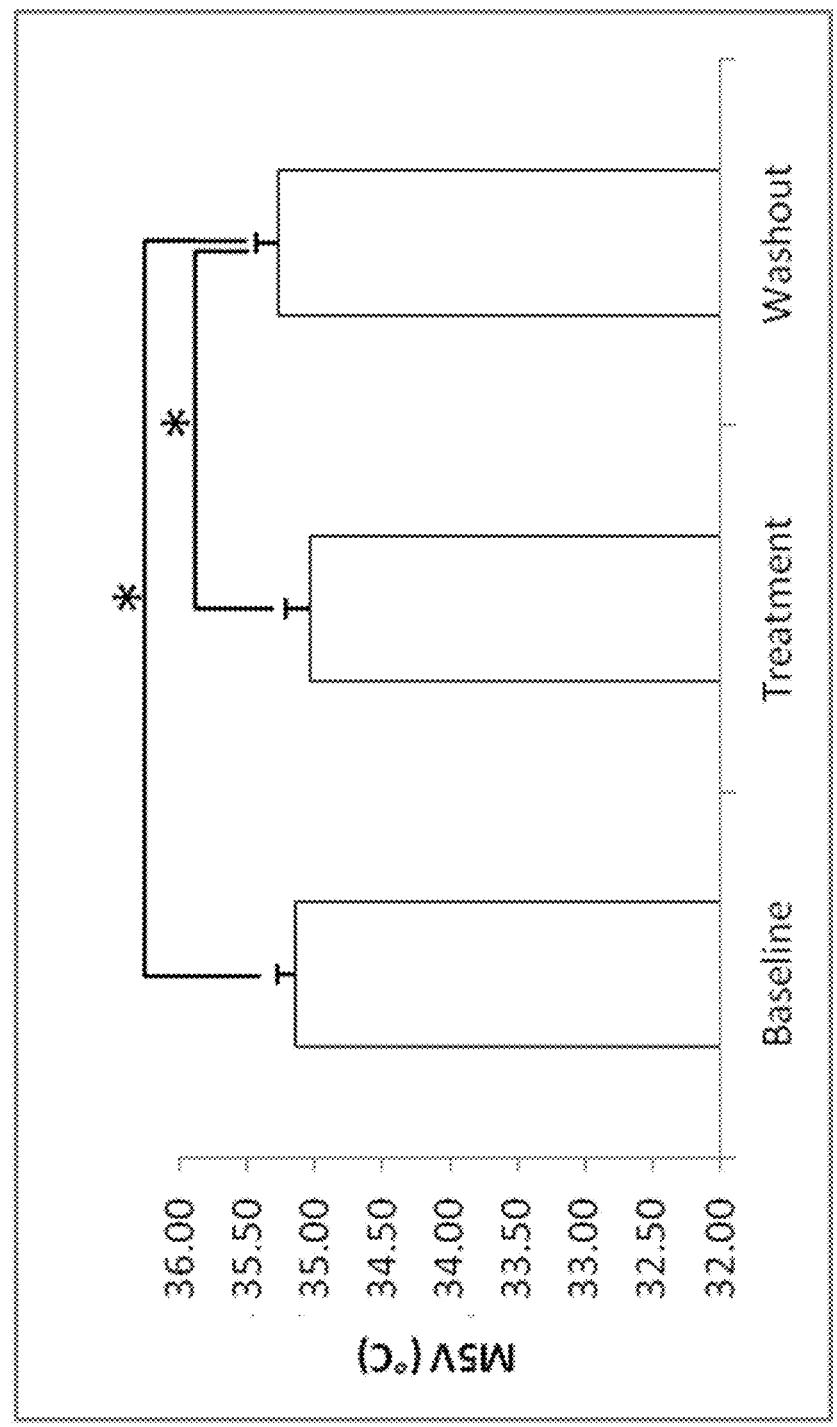
Figure 20F:
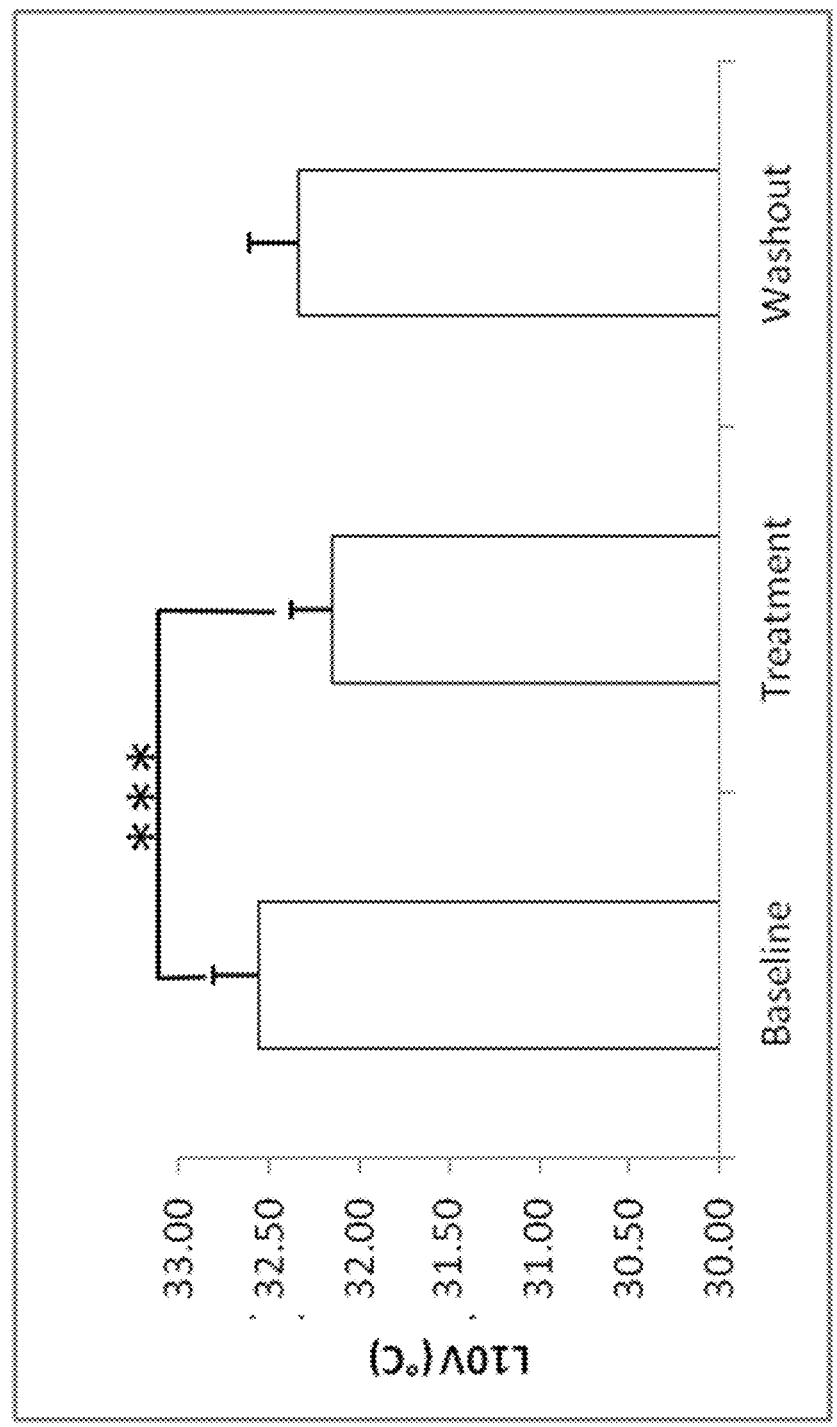
Figure 21:
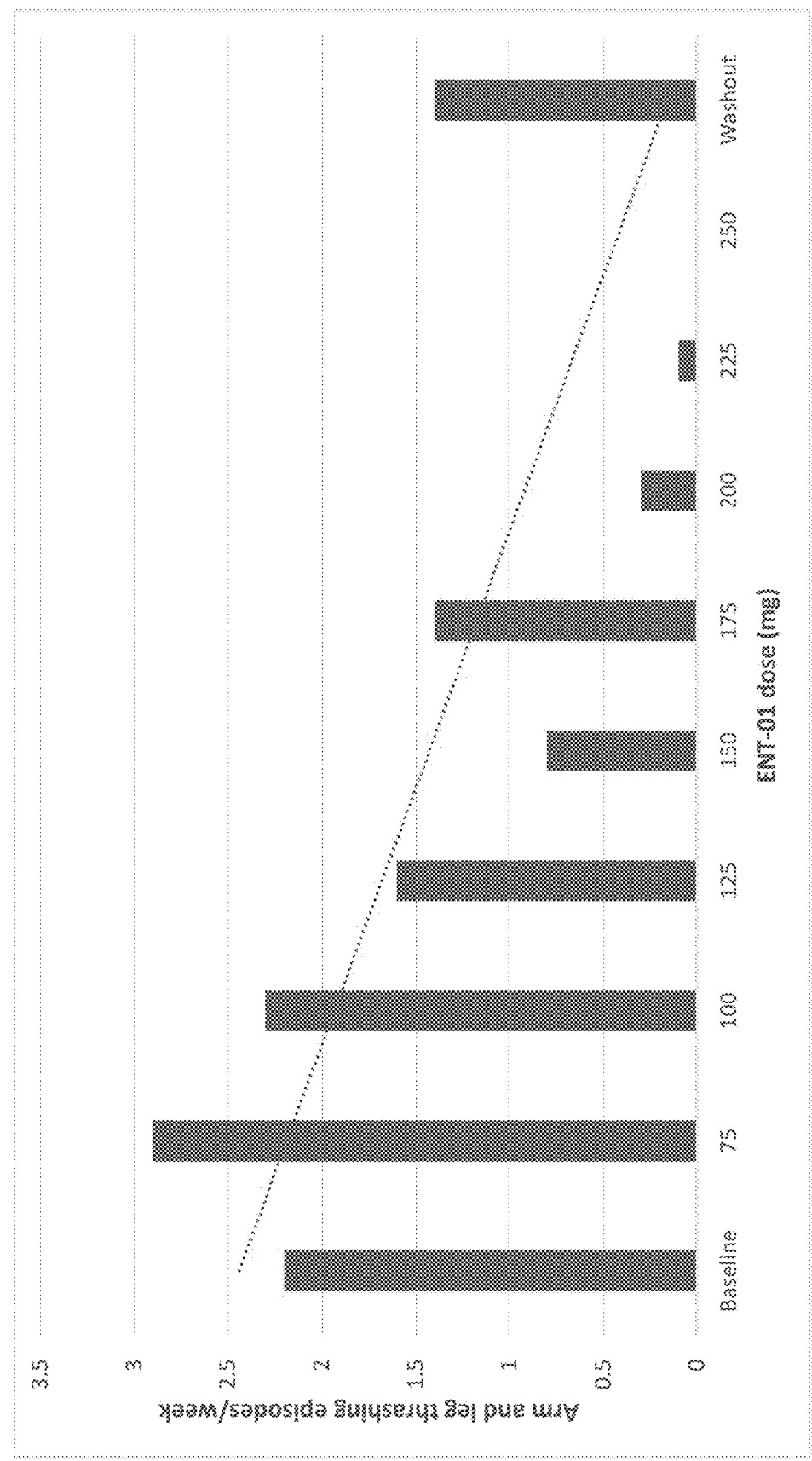
FIG. 21 shows REM-behavior disorder in relation to squalamine (ENT-01) dose, with arm and leg thrashing episodes (mean values) calculated using sleep diaries. The frequency of arm or leg thrashing reported in the sleep diary diminished progressively from 2.2 episodes/week at baseline to 0 at maximal dose.

The data detailed in Example 4 described how circadian system status was evaluated by continuously monitoring wrist skin temperature (Thermochron iButton DS1921H; Maxim, Dallas) following published procedures (Sarabia et al. 2008). Further, an analysis was done with respect to the sleep data, the body temperature data, and fatigue data. The frequency of arm or leg thrashing reported in the sleep diary diminished progressively from 2.2 episodes/week at baseline to 0 at maximal dose (100% improvement). Total sleep time increased progressively from 7.1 hours at baseline to 8.4 hours at 250 mg (an 18% increase) and was consistently higher than baseline beyond 125 mg (FIGS. 19, 22 and 23). FIG. 21 shows REM-behavior disorder in relation to squalamine (ENT-01) dose, with arm and leg thrashing episodes (mean values) calculated using sleep diaries. The frequency of arm or leg thrashing reported in the sleep diary diminished progressively from 2.2 episodes/week at baseline to 0 at maximal dose. Unlike stool-related indices, the improvement in many CNS symptoms persisted during wash-out.

Circadian rhythm of skin temperature was evaluable in 12 patients (i.e., those who had recordings that extended from baseline through washout). Circadian system functionality was evaluated by continuously monitoring wrist skin temperature using a temperature sensor (Thermochron iButton DS1921H; Maxim, Dallas, Tex.) (Sarabia et al. 2008). Briefly, this analysis includes the following parameters: (i) the inter-daily stability (the constancy of 24-hour rhythmic pattern over days, IS); (ii) intra-daily variability (rhythm fragmentation, IV); (iii) average of 10-minute intervals for the 10 hours with the minimum temperature (L10); (iv) average of 10-minute intervals for the 5 hours with the maximum temperature (M5) and the relative amplitude (RA), which was determined by the difference between M5 and L10, divided by the sum of both. Finally, the Circadian Function Index (CFI) was calculated by integrating IS, IV, and RA. Consequently, CFI is a global measure that oscillates between 0 for the absence of circadian rhythmicity and 1 for a robust circadian rhythm.

A comparison was performed of circadian rhythm parameters during the baseline, fixed dose and washout periods. Aminosterol administration improved all markers of healthy circadian function, including increasing rhythm stability, relative amplitude, and circadian function index, while reducing rhythm fragmentation. The improvement persisted for several of these circadian parameters during the washout period. (FIG. 20). Improvements were also seen in REM-behavior disorder (RBD) and sleep. RBD and total sleep time also improved progressively in a dose-dependent manner.

The disclosed methods can be used to treat or prevent a variety of sleep disorders which are discussed in more detail below.

B. Examples of Sleep Disorders

Sleep disorders and/or sleep disturbances include but are not limited to REM-behavior disorders, disturbances in the Circadian rhythm, delayed sleep onset, sleep fragmentation, and hallucinations. Other sleep disorders or disturbances that can be treated and/or prevented according to the disclosed methods include but are not limited to hypersomnia (i.e., daytime sleepiness), parasomnias (such as nightmares, night terrors, sleepwalking, and confusional arousals), periodic limb movement disorders (such as Restless Leg Syndrome), jet lag, narcolepsy, advanced sleep phase disorder, non-24 hour sleep-wake syndrome. Sleep disturbances include but are not limited to RBD, circadian rhythm dysfunction, delayed sleep onset, Restless leg syndrome, daytime sleepiness, and sleep fragmentation.

Jet lag is a traveler's sleep condition that affects the body's internal clock by causing sleep disruptions in a new time zone. The severity of jet lag depends on many factors—including age, quantity of time zones, and the direction of travel—causing the sufferer to become fatigued, nauseated, headachy, and unable to fall to sleep. Advanced sleep phase disorder (or ASPD) occurs when the biological clock sets to rise earlier than it should—for instance, the sufferer may feel the need to sleep at 7 pm and wake up at 3 am. ASPD most commonly affects seniors and is often linked to seasonal affective disorder (or SAD). Narcolepsy is one of the most dangerous sleep disorders. It's rare, affecting only roughly 100,000 Americans. The condition itself causes a dysfunction in the brain mechanisms that manage sleeping and waking—causing a person to instantly fall asleep while conversing, walking, driving, climbing stairs, working, etc. Most narcoleptics are extremely fatigued during the daytime hours, and suffer from hallucinations, muscle deterioration, sleep paralysis, and fainting. Subjects going to sleep earlier and earlier or waking up later and later, may have non-24-hour-sleep-wake syndrome, a condition that sets their biological clock to 25 hours or longer. This condition is often linked to blind individuals due to the absence of waking and sleeping light cues. Restless Leg Syndrome (or RLS) causes the lower legs to burn, ache, itch, twitch, and tingle upon falling sleep. It disrupts sleep mostly in middle-aged sufferers and is associated with a family history of RLS. Insomnia refers to a condition where subjects have a difficult time falling or staying asleep.

Approximately 70 million Americans suffer from one sleep disorder or another. Sleep disorders are characterized by any condition that prevents a person from getting restful sleep for a desirable period of time. The dangerous part isn't the actual sleep loss, but the dysfunction it causes during the waking hour when subjects are operating motor vehicles, work-associated machinery, and so forth.

Sleep is increasingly recognized as important to public health, with sleep insufficiency linked to motor vehicle crashes, industrial disasters, and medical and other occupational errors. Unintentionally falling asleep, nodding off while driving, and having difficulty performing daily tasks because of sleepiness all may contribute to these hazardous outcomes. Persons experiencing sleep insufficiency are also more likely to suffer from chronic diseases such as hypertension, diabetes, depression, and obesity, as well as from cancer, increased mortality, and reduced quality of life and productivity. Sleep insufficiency may be caused by broad scale societal factors such as round-the-clock access to technology and work schedules, but sleep disorders such as insomnia or obstructive sleep apnea also play an important role. An estimated 50-70 million US adults have a sleep or wakefulness disorder.

REM-behavior disorders. Normal sleep has two distinct states: non-rapid eye movement (NREM) and rapid eye movement (REM) sleep. NREM sleep is divided into four stages. During REM sleep, rapid eye movements occur, breathing becomes irregular, blood pressure rises, and there is a loss of muscle tone (paralysis). However, the brain is highly active, and the electrical activity recorded in the brain by EEG during REM sleep is similar to that recorded during wakefulness. REM sleep is usually associated with dreaming. REM sleep accounts for 20%-25% of the sleep period.

In a person with a REM-behavior disorder, the paralysis that normally occurs during REM sleep is incomplete or absent, allowing the person to "act out" his or her dreams. RBD is characterized by the acting out of dreams that are vivid, intense, and violent. Signs and symptoms of REM-behavior disorders include, but are not limited to, vivid dreams, nightmares, acting out the dreams by speaking or screaming, fidgeting, thrashing of arms or legs during sleep talking, yelling, punching, kicking, sitting, jumping from bed, and grabbing. REM-behavior disorders may also be associated with hallucinations.

An acute form of REM-behavior disorders may occur during withdrawal from alcohol or sedative-hypnotic drugs.

Disturbances in the Circadian rhythm ("Circadian Rhythm Dysfunction"). Circadian rhythm disorders are disruptions in a person's circadian rhythm (i.e., diurnal rhythm) that regulates the (approximately) 24-hour cycle of biological processes. The term circadian comes from Latin words that literally mean around the day. There are patterns of brain wave activity, hormone production, cell regeneration, and other biological activities linked to this 24-hour cycle.

The circadian rhythm is important in determining sleeping patterns such as when we sleep and when we wake, every 24 hours. Circadian rhythm disorders can be caused by many factors, including: shift work, pregnancy, jet lag, medications, mental health problems (e.g., schizophrenia), and degenerative or neurological conditions such as Parkinson's disease (PD), Alzheimer's disease, Huntington's Disease, multiple sclerosis, and degenerative processes associated with aging.

Delayed Sleep Onset and Sleep Fragmentation. Many individuals with a sleep disorder have a difficulty falling asleep or staying asleep. These are debilitating signs of various sleep disorders that can cause an afflicted individual to get less sleep than necessary or for their sleep to be less restful. When these features are severe enough, they may be considered insomnia.

Hypersomnia. Hypersomnia, which refers to either excessive daytime sleepiness or excessive time spent sleeping, is a condition in which a person has trouble staying awake during the day. People who have hypersomnia can fall asleep at any time—for instance, at work or while they are driving. They may also have other sleep-related problems, including a lack of energy and trouble thinking clearly.

There are several potential causes of hypersomnia, including, but not limited to, being overweight; drug or alcohol abuse; a head injury or a neurological disease, such as multiple sclerosis or Parkinson's disease; prescription drugs, such as tranquilizers or antihistamines; genetics (having a relative with hypersomnia); and depression.

Parasomnias. Parasomnias, such as nightmares, night terrors, sleepwalking, confusional arousals, and sleep paralysis, are disruptive sleep disorders that can occur during arousals from REM sleep or partial arousals from non-REM sleep. Often, the person experiencing the parasomnia is abruptly awakened from REM sleep. Parasomnias may also be associated with hallucinations.

Periodic Limb Movement Disorders. Periodic limb movement disorders (PLMD), such as restless leg syndrome, are characterized by rhythmic movements of the limbs during sleep. The movements typically involve the legs, but upper extremity movements may also occur. Movements occur periodically throughout the night and can fluctuate in severity from one night to the next. They tend to cluster in episodes that last anywhere from a few minutes to several hours. These movements are very different from the normal spasms, called hypnic myoclonia, that we often experience initially while trying to fall asleep and therefore can delay the onset of sleep.

The disclosed methods comprising orally or nasally administering a therapeutically effective amount of at least one aminosterol can be used to treat or prevent the above sleep disorders or the signs and symptoms of the disorders. For example, in one embodiment, the disclosed methods will improve, prevent, or ameliorate at least one or more of the signs or symptoms of the sleep disorder being treated. For instance, the disclosed methods may reduce delayed sleep onset and sleep fragmentation.

In some embodiments, treating the sleep disorder of a patient may also prevent or delay the onset of a neurodegenerative disorder.

In some embodiments, the sleep disorder comprises a loss of diurnal rhythm. This can be have a variety of underlying causes, including other medications, pregnancy, and various neurological conditions, and in some embodiments, the loss of diurnal rhythm is caused by dysfunction of the suprachiasmatic nucleus. In some embodiments, administration of at least one of the disclosed aminosterols reverses or reduces the dysfunction of the suprachiasmatic nucleus, thereby restoring the diurnal rhythm and/or treating the sleep disorder.

In some embodiments, the aminosterol used in the disclosed methods is a derivative or variant of squalamine modified through medical chemistry to improve bio-distribution, ease of administration, metabolic stability, or any combination thereof. In some embodiments, the aminosterol used in the disclosed methods is a derivative or variant of Aminosterol 1436 modified through medical chemistry to improve bio-distribution, ease of administration, metabolic stability, or any combination thereof. In some embodiments, the aminosterol used in the disclosed methods is a derivative or variant of a naturally occurring aminosterol modified through medical chemistry to improve bio-distribution, ease of administration, metabolic stability, or any combination thereof.

The mechanism of action. With respect to the disclosed methods, it is believed that squalamine and other aminosterols, such as Aminosterol 1436, are not necessarily absorbed in the GI tract but may nevertheless produce an aminosterol-induced CNS response. The presence of the aminosterol may induce various cellular-level responses, including effects on water and salt reabsorption. The aminosterol may also induce electrical activation of specific neurons, ultimately, by the electrostatic mechanism proposed.

Squalamine is known to gain access to nerve cells, neutralize the negative electrostatic surface potential of these cells, and alter electrical channel activity (Sumioka et al., 2009). Without being bound by a particular theory, it is assumed that aminosterols can access and influence the behavior of the neurons of the enteric nervous system in a fashion similar to what has been observed in cortical granular neurons (Sumioka et al., 2009). In addition, aminosterols such as squalamine are known to inhibit the sodium hydrogen exchanger involved in water and salt reabsorption in the human small intestine by the same mechanism (Alexander et al. 2011).

Based on the stereotyped nature of the response and known properties of certain human gastrointestinal hormones and the communication known to exist between the human GI tract and the central nervous system, aminosterols can induce a CNS response that improves the patient's sleeping pattern or improves, prevents, or ameliorates one or more of the signs or symptoms of the sleep disorder.

Without intending to be bound by theory, one proposed mechanism by which an aminosterol provokes the aminosterol-induced response involves the direct stimulation of nerves within the enteric nervous system, and stimulation of currents flowing towards the brain through afferent nerves of the vagus, which is predominantly parasympathetic and cholinergic. However, stimulation of other afferent neurons from gut to brain, including sympathetic nerves and sensory nerves, may also be involved in producing the desired affects. Stimulation of afferents of the vagus, which distribute to centers and tracts within the brain would be expected to stimulate release of a suite of neuropeptides within the brain itself. The continued imposition of the ileal brake for several days following aminosterol dosing, speaks to the length of time the aminosterol-provoked gut/CNS interaction must be operative following a single dose of aminosterol.

In addition, entry of aminosterols into the nerves could provide a direct benefit in sleeping disorders associated with degenerative conditions where accumulation of certain proteins is believed to be causally involved. For example, in Parkinson's disease, the accumulation of alpha synuclein is believed to play a role in the neuronal damage associated with the condition. Alpha synuclein is a protein with a cationic N-terminus and can interact electrostatically with the internal membranes of the nerve cell in which it is expressed. Since aminosterols (e.g., squalamine) can both enter nerve cells and neutralize the negative surface potential of these membrane surfaces, squalamine and related aminosterols have the capacity to displace alpha synuclein from membrane sites within nerves, and as a consequence, interrupt the pathophysiology of the disease. Beyond displacing alpha-synuclein, squalamine and 1436 may also increase nerve cell firing rates and duration. Accordingly, the effect on sleep may be independent of the ability of squalamine and 1436 to displace alpha-synuclein.

The sensitivity of the aminosterol-induced CNS response to oral administration of aminosterols is likely due to several variables: (1) the absorption of the aminosterol into a mucous layer, an effect that would reduce free concentration of aminosterol available for diffusion onto the epithelial surface, thereby reducing the response to a given oral dose; and (2) an increase in the permeability of the epithelial wall (leakiness), which occurs following infections, allergic enteropathies, and in states of intestinal inflammation. In such settings, the normal transport of the aminosterol across the epithelium, which is facilitated by the controlled entry and subsequent exit of the molecule from the lining epithelial cell, would be circumvented. The compound would leak across the epithelial barrier, and expose the nerve network within the bowel wall to abnormally high concentrations. Hence, an excessive response might provide a diagnostic impression of the permeability status of the epithelium.

The disclosed methods can be used to treat a range of subjects, including human and non-human animals, including mammals, as well as immature and mature animals, including human children and adults.

B. Patient Populations

In recognition of the importance of sleep to the nation's health, CDC surveillance of sleep-related behaviors has increased in recent years. Additionally, the Institute of Medicine encouraged collaboration between CDC and the National Center on Sleep Disorders Research to support development and expansion of adequate surveillance of the U.S. population's sleep patterns and associated outcomes. Two new reports on the prevalence of unhealthy sleep behaviors and self-reported sleep-related difficulties among U.S. adults provide further evidence that insufficient sleep is an important public health concern.

The Behavioral Risk Factor Surveillance System (BRFSS) survey included a core question regarding perceived insufficient rest or sleep in 2008 and an optional module of four questions on sleep behavior in 2009. Data from the 2009 BRFSS Sleep module were used to assess the prevalence of unhealthy/sleep behaviors by selected sociodemographic factors and geographic variations in 12 states. The analysis determined that, among 74,571 adult respondents in 12 states, 35.3% reported <7 hours of sleep during a typical 24-hour period, 37.9% reported unintentionally falling asleep during the day at least once in the preceding month, and 4.7% reported nodding off or falling asleep while driving at least once in the preceding month. This is the first CDC surveillance report to include estimates of drowsy driving and unintentionally falling asleep during the day. The National Department of Transportation estimates drowsy driving to be responsible for 1,550 fatalities and 40,000 nonfatal injuries annually in the United States.

The National Health and Nutrition Examination Survey (NHANES) introduced the Sleep Disorders Questionnaire in 2005 for participants 16 years of age and older. This analysis was conducted using data from the last two survey cycles (2005-2006 and 2007-2008) to include 10,896 respondents aged ≥20 years. A short sleep duration was found to be more common among adults ages 20-39 years (37.0%) or 40-59 years (40.3%) than among adults aged ≥60 years (32.0%), and among non-Hispanic blacks (53.0%) compared to non-Hispanic whites (34.5%), Mexican-Americans (35.2%), or those of other race/ethnicity (41.7%). Adults who reported sleeping less than the recommended 7-9 hours per night were more likely to have difficulty performing many daily tasks.

How much sleep is needed by a subject varies between individuals but generally changes with age. The National Institutes of Health suggests that school-age children need at least 10 hours of sleep daily, teens need 9-10 hours, and adults need 7-8 hours. According to data from the National Health Interview Survey, nearly 30% of adults reported an average of ≤6 hours of sleep per day in 2005-2007. Further, in 2009, only 31% of high school students reported getting at least 8 hours of sleep on an average school night. Similar recommendations are provided by the National Sleep Foundation (https://sleepfoundation.org/press-release/national-sleep-foundation-recommends-new-sleep-times/page/0/1):

TABLE 1

| Age | Recommended | May be appropriate | Not recommended |
|---|---|---|---|
| Newborns 0-3 months | 14 to 17 hours | 11 to 13 hours 18 to 19 hours | Less than 11 hours More than 19 hours |
| Infants 4-11 months | 12 to 15 hours | 10 to 11 hours 16 to 18 hours | Less than 10 hours More than 18 hours |
| Toddlers 1-2 years | 11 to 14 hours | 9 to 10 hours 15 to 16 hours | Less than 9 hours More than 16 hours |
| Preschoolers 3-5 years | 10 to 13 hours | 8 to 9 hours 14 hours | Less than 8 hours More than 14 hours |
| School-aged Children 6-13 years | 9 to 11 hours | 7 to 8 hours 12 hours | Less than 7 hours More than 12 hours |
| Teenagers 14-17 years | 8 to 10 hours | 7 hours 11 hours | Less than 7 hours More than 11 hours |
| Young Adults 18-25 years | 7 to 9 hours | 6 hours 10 to 11 hours | Less than 6 hours More than 11 hours |
| Adults 26-64 years | 7 to 9 hours | 6 hours 10 hours | Less than 6 hours More than 10 hours |
| Older Adults ≥65 years | 7 to 8 hours | 5 to 6 hours 9 hours | Less than 5 hours More than 9 hours |

In one aspect of the invention, encompassed is a method of treating or preventing a sleep disorder or sleep disturbance in a subject, comprising orally or nasally administering to the subject at least one aminosterol or a pharmaceutically equivalent salt thereof at a therapeutically effective dose, wherein the method results in the subject obtaining a restful sleep period. In another aspect of the invention, the method results in the subject obtaining a restful sleep period encompassed by the recommended or appropriate amount of sleep for the subject's age category, e.g., infants 0-3 months=11-19 hours; infants 4-11 months=12-18 hours; toddlers 1-2 years=9-16 hours; preschoolers 3-5 years=10-14 hours; school-aged children 6-13 years=7-12 hours; teenagers 14-17 years=7-11 hours; young adults 18-25 years=6-11 hours; adults 26-64 years=6-10 hours; and older adults ≥65 years=5-9 hours.

A "restful sleep period" is defined as a sleep period uninterrupted by wakefulness. There are several different scientifically acceptable ways to measure a sleep period uninterrupted by wakefulness. First, electrodes attached to the head of a subject can measure electrical activity in the brain by electroencephalography (EEG). This measure is used because the EEG signals associated with being awake are different from those found during sleep. Second, muscle activity can be measured using electromyography (EMG), because muscle tone also differs between wakefulness and sleep. Third, eye movements during sleep can be measured using electro-oculography (EOG). This is a very specific measurement that helps to identify Rapid Eye Movement or REM sleep. Any of these methods, or a combination thereof, can be used to determine if a subject obtains a restful sleep period following administration of at least one aminosterol to the subject.

In another aspect of the invention, encompassed is a method of treating or preventing a sleep disorder or sleep disturbance in an infant subject, comprising orally or nasally administering to the infant subject at least one aminosterol or a pharmaceutically equivalent salt thereof at a therapeutically effective dose, wherein the method results in the subject obtaining a restful sleep period of at least about 5, about 6, about 7, about 8, about 9, about 10, about 11, about 12, about 13, about 14, about 15, or about 16 hours. "Infant" subjects can be anywhere from 0 to 12 months of age.

In another aspect of the invention, encompassed is a method of treating or preventing a sleep disorder or sleep disturbance in a toddler subject, comprising orally or nasally administering to the toddler subject at least one aminosterol or a pharmaceutically equivalent salt thereof at a therapeutically effective dose, wherein the method results in the subject obtaining a restful sleep period of at least about 5, about 6, about 7, about 8, about 9, about 10, about 11, about 12, about 13, about 14, about 15, or about 16 hours. "Toddler" subjects can be from 1-2 years, up to less than 3 years.

In another aspect of the invention, encompassed is a method of treating or preventing a sleep disorder or sleep disturbance in a preschooler subject, comprising orally or nasally administering to the preschooler subject at least one aminosterol or a pharmaceutically equivalent salt thereof at a therapeutically effective dose, wherein the method results in the subject obtaining a restful sleep period of at least about 5, about 6, about 7, about 8, about 9, about 10, about 11, about 12, about 13, or about 14 hours. "Preschooler" subjects can be from 3-5 years, up to less than 6 years.

In another aspect of the invention, encompassed is a method of treating or preventing a sleep disorder or sleep disturbance in a school-aged children, comprising orally or nasally administering to the school-aged children at least one aminosterol or a pharmaceutically equivalent salt thereof at a therapeutically effective dose, wherein the method results in the subject obtaining a restful sleep period of at least about 5, about 6, about 7, about 8, about 9, about 10, about 11, or about 12. "School-aged children" subjects can be from 6-13 years, up to less than 14 years.

In another aspect of the invention, encompassed is a method of treating or preventing a sleep disorder or sleep disturbance in a teenage subject, comprising orally or nasally administering to the teenage subject at least one aminosterol or a pharmaceutically equivalent salt thereof at a therapeutically effective dose, wherein the method results in the subject obtaining a restful sleep period of at least about 5, about 6, about 7, about 8, about 9, about 10, or about 11 hours. "Teenage" subjects can be from 14-17 years, up to less than 18 years.

In another aspect of the invention, encompassed is a method of treating or preventing a sleep disorder or sleep disturbance in a young adult subject, comprising orally or nasally administering to the young adult subject at least one aminosterol or a pharmaceutically equivalent salt thereof at a therapeutically effective dose, wherein the method results in the subject obtaining a restful sleep period of at least about 5, about 6, about 7, about 8, about 9, about 10, or about 11 hours. "Young adult" subjects can be about 18-25 years, up to less than 26 years.

In another aspect of the invention, encompassed is a method of treating or preventing a sleep disorder or sleep disturbance in an adult subject, comprising orally or nasally administering to the adult subject at least one aminosterol or a pharmaceutically equivalent salt thereof at a therapeutically effective dose, wherein the method results in the subject obtaining a restful sleep period of at least about 5, about 6, about 7, about 8, about 9, or about 10 hours. "Adult" subjects can be about 26-64 years, up to less than 65 years.

In another aspect of the invention, encompassed is a method of treating or preventing a sleep disorder or sleep disturbance in an elderly or older adult subject, comprising orally or nasally administering to the elderly or older adult subject at least one aminosterol or a pharmaceutically equivalent salt thereof at a therapeutically effective dose, wherein the method results in the subject obtaining a restful sleep period of at least about 5, about 6, about 7, about 8, or about 9 hours. "Elderly" or "older adult" subjects can be 65 or more years of age.

In another embodiment of the invention, encompassed is a method of treating or preventing a sleep disorder or sleep disturbance in a subject suffering from a neurodegenerative condition of the CNS, comprising orally or nasally administering to the subject at least one aminosterol or a pharmaceutically equivalent salt thereof at a therapeutically effective dose, wherein the method results in the subject obtaining a restful sleep period of at least about 5, about 6, about 7, about 8, about 9, about 10, about 11, or about 12 hours. In other embodiments of the invention, the neurodegenerative condition of the CNS is Parkinson's disease, Alzheimer's disease, Huntington's chorea and/or Disease, schizophrenia, multiple sclerosis, dementia, degenerative processes associated with aging, dementia of aging, multisystem atrophy (MSA), fronto-temporal dementia, autism, progressive nuclear palsy, Guadeloupian Parkinsonism, spinocerebellar ataxia, Amyotorphic Lateral Sclerosis (ALS), Friedreich's ataxia, vascular dementia, Lewy Body dementia or disease, spinal muscular atrophy, supranuclear palsy, fronto temperal dementia, neuropathy of diabetes, peripheral sensory neuropathy, cerebral palsy, epilepsy, diabetic neuropathy, or depression.

In another embodiment of the invention, encompassed is a method of treating or preventing a sleep disorder or sleep disturbance in a subject suffering from degenerative processes associated with aging, comprising orally or nasally administering to the subject at least one aminosterol or a pharmaceutically equivalent salt thereof at a therapeutically effective dose, wherein the method results in the subject obtaining a restful sleep period of at least about 5, about 6, about 7, about 8, about 9, about 10, about 11, or about 12 hours. In other embodiments of the invention.

In another embodiment of the invention, essentially no aminosterol is detected in the blood stream of the subject following oral administration.

These conditions and the ways in which they can be treated and/or prevented by orally or nasally administering aminosterols (e.g., squalamine) are discussed in more detail below.

III. Methods of Treating Sleep Disorders or Related Symptoms Comprising a "Fixed Dose" of Aminosterol The present application relates to the surprising discovery of a method to determine a "fixed dose" of an aminosterol composition for treating constipation and/or constipation-related symptoms in a subject that is not age, size, or weight dependent but rather is individually calibrated. The "fixed dose" obtained through this method yields highly effective results in treating constipation.

A. "Fixed" Aminosterol Dose

A "fixed aminosterol dose," also referred to herein as a "fixed escalated aminosterol dose," which will be therapeutically effective, is determined for each subject by establishing a starting dose of an aminosterol composition and a threshold for improvement of a sleeping disorder or a related symptom. Following determining a starting aminosterol dose for a particular subject, the aminosterol dose is then progressively escalated by a consistent amount over consistent time intervals until the desired improvement in the sleeping disorder or a related symptom is achieved; this aminosterol dosage is the "fixed escalated aminosterol dosage" for that particular subject for the sleeping disorder or related symptom.

This therapeutically effective "fixed dose" is then maintained throughout treatment and/or prevention. Thus, even if the subject goes "off drug" and ceases taking the aminosterol composition, the same "fixed dose" is taken with no ramp up period following re-initiation of aminosterol treatment for a sleep disorder or related symptom.

Not to be bound by theory, it is believed that the aminosterol dose is dependent on the severity of nerve damage relating to the sleep disorder or related symptom, e.g. the dose may be related to the extent of nervous system damage resulting in the sleep disorder or related symptom.

The aminosterol can be administered via any pharmaceutically acceptable means, such as by injection (e.g., IM, IV, or IP), oral, pulmonary, intranasal, etc. Preferably, the aminosterol is administered orally, intranasally, or a combination thereof.

Oral dosage of an aminosterol can range from about 1 to about 500 mg/day, or any amount in-between these two values. Other exemplary dosages of orally administered aminosterols include, but are not limited to, about 5, about 10, about 15, about 20, about 25, about 30, about 35, about 40, about 45, about 50, about 55, about 60, about 65, about 70, about 75, about 80, about 85, about 90, about 95, about 100, about 105, about 110, about 115, about 120, about 125, about 130, about 135, about 140, about 145, about 150, about 155, about 160, about 165, about 170, about 175, about 180, about 185, about 190, about 195, about 200, about 205, about 210, about 215, about 220, about 225, about 230, about 235, about 240, about 245, about 250, about 255, about 260, about 265, about 270, about 275, about 280, about 285, about 290, about 295, about 300, about 305, about 310, about 315, about 320, about 325, about 330, about 335, about 340, about 345, about 350, about 355, about 360, about 365, about 370, about 375, about 380, about 385, about 390, about 395, about 400, about 405, about 410, about 415, about 420, about 425, about 430, about 435, about 440, about 445, about 450, about 455, about 460, about 465, about 470, about 475, about 480, about 485, about 490, about 495, or about 500 mg/day.

Intranasal dosages of an aminosterol are much lower than oral dosages of an aminosterol. Examples of such intranasal aminosterol low dosages include, but are not limited to, about 0.001 to about 6 mg, or any amount in-between these two values. For example, the low dosage of an intranasal administered aminosterol can be about 0.001, about 0.005, about 0.01, about 0.02, about 0.03, about 0.04, about 0.05, about 0.06, about 0.07, about 0.08, about 0.09, about 0.1, about 0.2, about 0.3, about 0.4, about 0.5, about 0.6, about 0.7, about 0.8, about 0.9, about 1, about 1.1, about 1.2, about 1.3, about 1.4, about 1.5, about 1.6, about 1.7, about 1.8, about 1.9, about 2, about 2.1, about 2.2, about 2.3, about 2.4, about 2.5, about 2.6, about 2.7, about 2.8, about 2.9, about 3, about 3.1, about 3.2, about 3.3, about 3.4, about 3.5, about 3.6, about 3.7, about 3.8, about 3.9, about 4, about 4.1, about 4.2, about 4.3, about 4.4, about 4.5, about 4.6, about 4.7, about 4.8, about 4.9, about 5, about 5.1, about 5.2, about 5.3, about 5.4, about 5.5, about 5.6, about 5.7, about 5.8, about 5.9, or about 6 mg/day.

For intranasal (IN) administration, it is contemplated that the aminosterol dosage may be selected such that it would not provide any pharmacological effect if administered by any other route and, in addition, does not result in negative effects. For example, Aminosterol 1436 is known to have the pharmacological effects of a reduction in food intake and weight loss. Therefore, in the IN methods of the invention, if the aminosterol is Aminosterol 1436 or a salt or derivative thereof, then if the IN Aminosterol 1436 dosage is administered via another route, such as oral, IP, or IV, then the Aminosterol 1436 dosage will not result in a noticeable reduction in food intake or noticeable weight loss. Similarly, squalamine is known to produce the pharmacological effects of nausea, vomiting and/or reduced blood pressure. Thus, in the IN methods of the invention, if the aminosterol is squalamine or a salt or derivative thereof, then if the IN squalamine dosage is administered via another route, such as oral, IP, or IV, then the squalamine dosage will not result in noticeable nausea, vomiting, and/or a reduction in blood pressure.

Dose escalation: When determining a "fixed aminosterol dosage" for a particular subject, a subject is started at a lower dose and then the dose is escalated until a positive result is observed for a sleep disorder or related symptom. For example, determination of the fixed aminosterol dosage for treating constipation is shown in Example 1. Aminosterol doses can also be de-escalated (reduced) if any given aminosterol dose induces a persistent undesirable side effect, such as diarrhea, vomiting, or nausea.

The starting aminosterol dose is dependent on the severity of the symptom—e.g. for a subject experiencing a severe sleep disorder, defined as a sleep disorder, sleep disturbance or symptom which results in a subject obtaining less than about 50% of the hours of sleep recommended by a medical authority for the age group of the subject, the starting oral aminosterol dose can be about 150 mg or greater. In contrast, for a subject having a moderate sleep disorder, e.g., defined as a sleep disorder, sleep disturbance or symptom which results in a subject obtaining at least 50% of the hours of sleep recommended by a medical authority for the age group of the subject, the starting aminosterol dose can be about 75 mg or less. Thus, as an example, a subject experiencing a moderate sleep disorder or related symptom can be started at an aminosterol dosage of about 75 mg/day, whereas a subject experiencing a severe sleep disorder or related symptom can be started at an aminosterol dosage of about 150 mg/day.

In other embodiments, a subject experiencing a moderate sleep disorder or related symptom can be started at an oral aminosterol dosage of from about 10 mg/day to about 75 mg/day, or any amount in-between these values. For example, starting oral aminosterol dosage for patients with a moderate to mild sleep disorder or related symptom can be about 1, about 5, about 10, about 15, about 20, about 25, about 30, about 35, about 40, about 45, about 50, about 55, about 60, about 65, about 70, up to less than or equal to about 75 mg/day. A fixed escalated oral aminosterol dose for a subject with a mild or moderate sleep disorder or related symptom is likely to range from about 5 mg up to about 350 mg, or any amount in-between these two values as described herein. In some embodiments, an oral fixed aminosterol dose, following dose escalation, is from about 50 to about 300 mg/daily, or from about 75 to about 275 mg/daily.

In yet further embodiments, when the subject is experiencing a severe sleep disorder or related symptom, the subject can be started at an oral aminosterol dosage ranging from about 75 to about 300 mg/day, or any amount in-between these two values. In other embodiments, the starting oral aminosterol dosage for a subject with a severe sleep disorder or related symptom can be, for example, about 75, about 80, about 85, about 90, about 95, about 100, about 105, about 110, about 115, about 120, about 125, about 130, about 135, about 140, about 145, about 150, about 155, about 160, about 165, about 170, about 175, about 180, about 185, about 190, about 195, about 200, about 205, about 210, about 215, about 220, about 225, about 230, about 235, about 240, about 245, about 250, about 255, about 260, about 265, about 270, about 275, about 280, about 285, about 290, about 295, or about 300 mg/day. A "fixed escalated" oral aminosterol dose for a subject with a severe sleep disorder or related symptom is likely to range from about 75 mg up to about 500 mg.

In some embodiments, the starting aminosterol dose may be about 125 mg or about 175 mg; again dependent on the severity of the symptom.

Starting intranasal (IN) aminosterol dosages prior to dose escalation can be, for example, about 0.001 mg to about 3 mg, or any amount in-between these two values. For example, the starting aminosterol dosage for IN administration, prior to dose escalation, can be, for example, about 0.001, about 0.005, about 0.01, about 0.02, about 0.03, about 0.05, about 0.06, about 0.07, about 0.08, about 0.09, about 0.1, about 0.15, about 0.2, about 0.25, about 0.3, about 0.35, about 0.4, about 0.45, about 0.5, about 0.55, about 0.6, about 0.65, about 0.7, about 0.75, about 0.8, about 0.85, about 0.9, about 1.0, about 1.1, about 1.25, about 1.3, about 1.4, about 1.5, about 1.6, about 1.7, about 1.75, about 1.8, about 1.9, about 2.0, about 2.1, about 2.25, about 2.3, about 2.4, about 2.5, about 2.6, about 2.7, about 2.75, about 2.8, about 2.9, or about 3 mg.

In exemplary embodiments, the fixed dose of the aminosterol is given periodically as needed. For example, the fixed aminosterol dose can be given once per day. The aminosterol dose can also be given every other day, 2, 3, 4, 5 or 6× per week, once/week, or 2×/week. In another embodiment, the aminosterol dose can be given every other week, or it can be given for a few weeks, followed by skipping a few weeks (as the effects persist following treatment), followed by restarting aminosterol treatment.

When calculating a fixed escalated aminosterol dose, the dose can be escalated following any suitable time period. In one embodiment, the aminosterol dose is escalated every about 3 to about 7 days by about a defined amount until a desired improvement is reached. In one embodiment, the aminosterol dose is escalated every about 3 to 5 days until a desired improvement is reached. For example, when the symptom being treated/measured is the number of hours of uninterrupted sleep, threshold improvement can be an increase of one hour per night, on average per week. In other embodiments, the aminosterol dose can be escalated every about 1, about 2, about 3, about 4, about 5, about 6, about 7, about 8, about 9, about 10, about 11, about 12, about 13, or about 14 days. In other embodiments, the aminosterol dose can be escalated about 1×/week, about 2×/week, about every other week, or about 1×/month.

During dose escalation, the aminosterol dosage can be increased by a defined amount. For example, when the aminosterol is administered orally, the dose can be escalated in increments of about 5, about 10, about 15, about 20, about 25, about 30, about 35, about 40, about 45, or by about 50 mg. When the aminosterol is administered intranasally, then the dosage can be increased in increments of about, for example, about 0.1, about 0.2, about 0.25, about 0.3, about 0.35, about 0.4, about 0.45, about 0.5, about 0.55, about 0.6, about 0.65, about 0.7, about 0.75, about 0.8, about 0.85, about 0.9, about 0.95, about 1, about 1.1, about 1.2, about 1.3, about 1.4, about 1.5, about 1.6, about 1.7, about 1.8, about 1.9, or about 2 mg.

In exemplary embodiments, an orally administered aminosterol dose is escalated every about 3 to about 5 days by about 25 mg until the desired improvement or resolution of the sleep disorder or related symptom is reached.

In another embodiment, a fixed dose of an aminosterol can be varied plus or minus a defined amount to enable a modest reduction in a dose to eliminate adverse events, or a modest increase in a dose if clinical results suggest this is desirable—e.g., no or minimal adverse events and potential increased efficacy with a modest increase in dose. For example, in one embodiment a fixed aminosterol dose can be increased or decreased by about 1%, about 2%, about 3%, about 4%, about 5%, about 6%, about 7%, about 8%, about 9%, about 10%, about 11%, about 12%, about 13%, about 14%, about 15%, about 16%, about 17%, about 18%, about 19%, or about 20%.

B. Sleep Disorder and Related Symptoms to be Evaluated

The "fixed" dose of an aminosterol or a salt or derivative thereof is determined based upon the effect an escalated aminosterol dose has, over a period of time, on a sleep disorder or a related symptom. Measurable sleep disorders or related symptoms that can be evaluated include, for example: (1) total sleep time; (2) total number of hours of uninterrupted sleep, per day; (3) sleep efficiency; (4) presence or frequency of a change in sleeping patterns; (5) presence or frequency of a change in Circadian rhythm; (6) developing a normal Circadian (i.e., diurnal) rhythm; (7) presence of a sleep-wake cycle that is not 24 hours; (8) sleeping at night rather than during the day, when night would is the preferred sleeping period; (9) presence and/or frequency of awakenings during sleep period; (10) presence and/or frequency of nonrestorative sleep; (11) presence and/or frequency of a difficulty maintaining sleep; (12) presence and/or frequency of sleep fragmentation; (13) presence and/or frequency of hallucinations during sleep period; (14) presence and/or frequency of thrashing or limb movement during sleep period, which can for example be associated with REM behavior disorder (RBD); (15) presence and/or frequency of nightmares and/or vivid dreams, which can for example be associated with associated with RBD; (16) presence and/or frequency of delayed sleep onset; (17) presence and/or frequency of day time sleepiness; (18) presence and/or frequency of clinical or subclinical "sleep attacks"(i.e. an irresistible urge to sleep or experiencing narcolepsy with cataplexy); (19) cognitive impairment and/or improvement in memory as a result of better memory consolidation during sleep; (20) presence and/or frequency of disturbances in sleep architecture; (21) time of awakening following sleep period, with a later time correlated with improved sleep; (22) presence and/or frequency of sleep problems; (23) presence and/or frequency of sleep disturbances and/or sleep disruption; (24) REM disturbed sleep; (25) presence and/or frequency of apnea; (26) presence and/or frequency of narcolepsy; (27) poor psychomotor coordination; (28) presence and/or frequency of headaches; (29) presence and/or frequency of gastrointestinal distress; (30) presence and/or frequency of insomnia; (31) presence and/or frequency of parasomnias; (32) diurnal skin temperature oscillations; (33) a symptom from the Horne-Östberg Morningness-Eveningness Questionnaire (MEQ) selected from the group consisting of difficulty waking up in the morning, difficulty falling asleep at night, falling asleep earlier than normal at night, dependence on alarm to wake in morning, lack of alertness in morning, appetite upon waking in morning, feeling tired after waking in the morning, going to bed later than normal when subject has no commitments the following day, inability to fall back to sleep upon waking in the morning, lack of willingness to engage in physical activity in the morning, and lack of willingness to engage in cognitively challenging tasks in the morning; (33) a symptom from the Epworth Sleepiness Scale (ESS) selected from the group consisting of dozing or sleeping when sitting and reading, dozing or sleeping when watching television (TV), dozing or sleeping when sitting while inactive in public, dozing or sleeping when riding as a passenger in a car for greater than 1 hour, dozing or sleeping when lying down in the afternoon, dozing or sleeping when talking to another person, dozing or sleeping when sitting quietly after lunch, and dozing or sleeping when driving and stopped in traffic; (35) REM behavior disorder (RBD); (36) circadian rhythm dysfunction; (37) Restless leg syndrome; (38) jet lag; (39) hypersomnia; and/or (40) personal judgment of restful sleep.

The symptoms can be measured using a clinically recognized scale or tool, as detailed herein. Examples of such clinical scales or tools include, but are not limited to: (1) Sleep Diary; (2) I-Button Temperature Assessment; (3) Unified Parkinson's Disease Rating Scale (UPDRS), sections 1.7 (sleep problems), 1.8 (daytime sleepiness) and 1.13 (fatigue); (4) Parkinson's Disease Fatigue Scale (PFS-16); (5) REM Sleep Behavior Disorder Screening Questionnaire; (6) Parkinson's Disease Sleep Scale; (7) Epworth Sleepiness Scale (ESS); and (8) Horne-Östberg Morningness-Eveningness Questionnaire (MEQ).

IV. Compositions Useful in the Methods of the Invention
   A. Aminosterols

U.S. Pat. No. 6,962,909, entitled "Treatment of neovascularization disorders with squalamine," discloses various aminosterols, and this disclosure is specifically incorporated by reference with respect to its teaching of aminosterol compounds. Any aminosterol known in the art, including those described in U.S. Pat. No. 6,962,909, can be used in the disclosed methods. In some embodiments, the aminosterol present in the compositions of the invention is Aminosterol 1436 or a salt or derivative thereof, squalamine or a salt or derivative thereof, or a combination thereof.

For instance, useful aminosterol compounds comprise a bile acid nucleus and a polyamine, attached at any position on the bile acid, such that the molecule exhibits a net positive charge contributed by the polyamine.

Thus, in some embodiments, the disclosed methods comprise orally or nasally administering a therapeutically effective amount of one or more aminosterols having the chemical structure of Formula I:

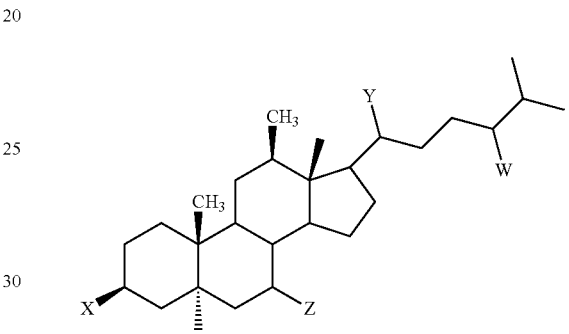

wherein,
W is 24S—OSO$_3$ or 24R—OSO$_3$;
X is 3β-H$_2$N—(CH$_2$)$_4$—NH—(CH$_2$)$_3$—NH— or 3α-H$_2$N—(CH$_2$)$_4$—NH—(CH$_2$)$_3$—NH—;
Y is 20R—CH$_3$; and
Z is 7α or 7β —OH.

In another embodiment of the invention, the aminosterol is one of the naturally occurring aminosterols (1-8) isolated from *Squalus acanthias*:

Compound 1

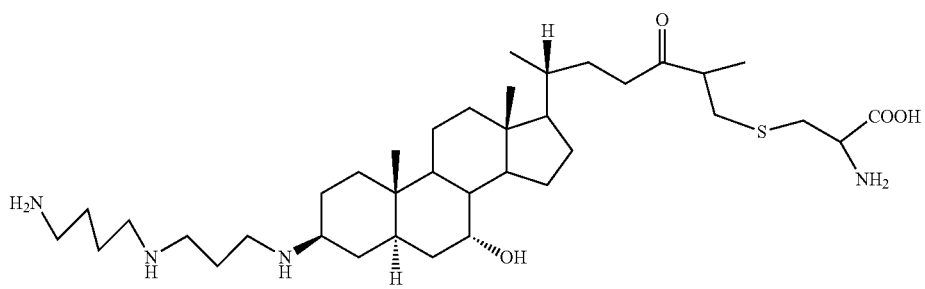

Compound 2

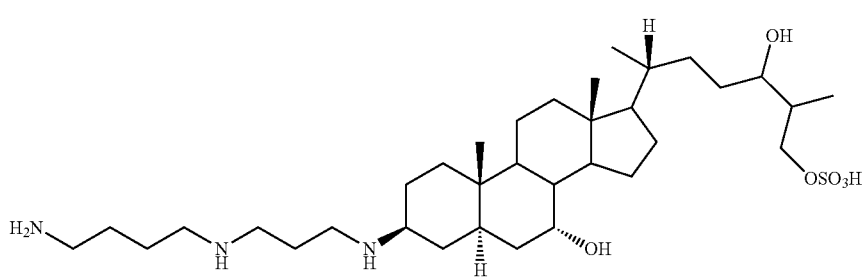

-continued
Compound 3
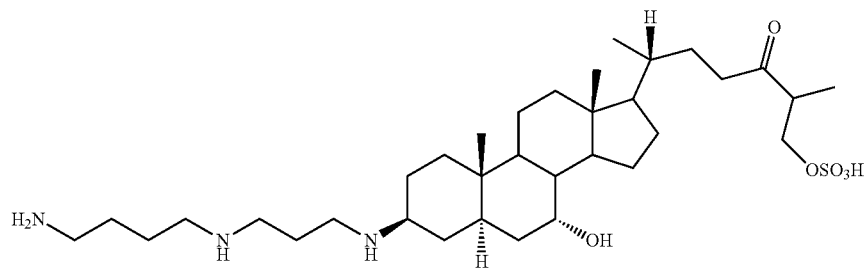
Compound 4
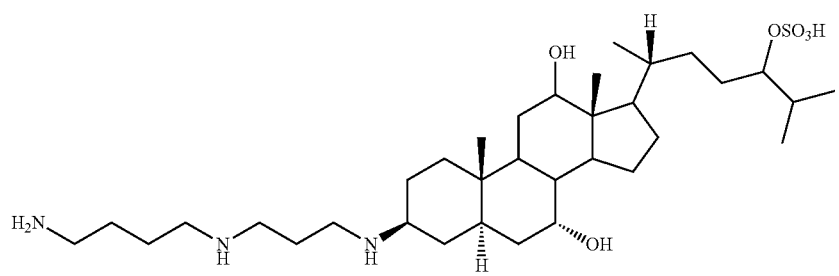
Compound 5
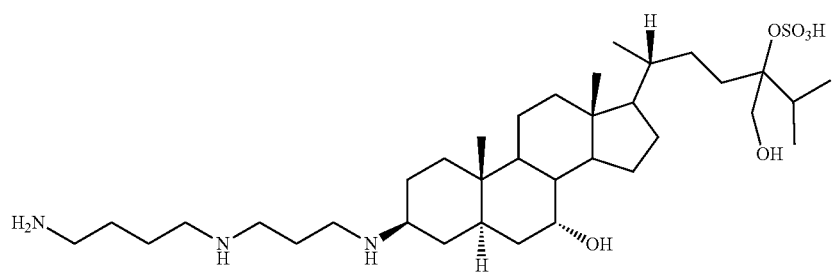
Compound 6
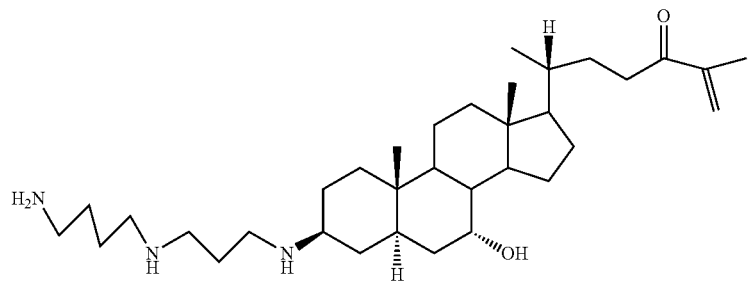
Compound 7
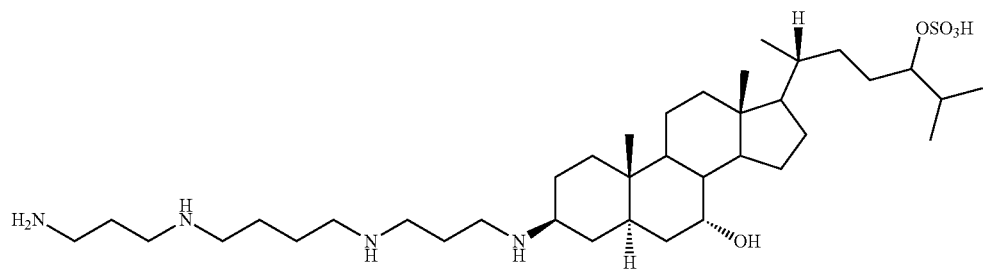

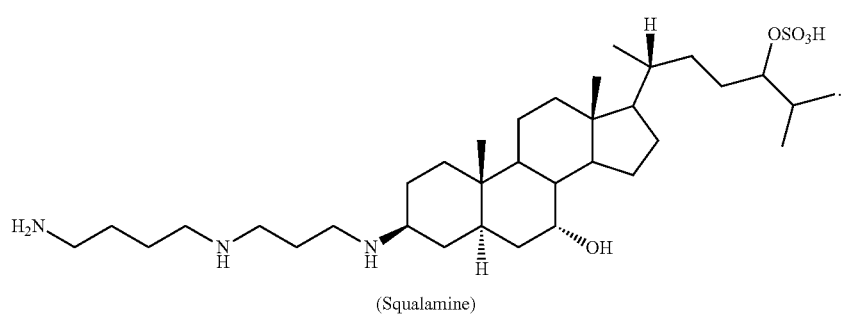

Compound 8

(Squalamine)

Variants or derivatives of known aminosterols, such as squalamine, Aminosterol 1436, or an aminosterol isolated from *Squalus acanthias*, may be used in the disclosed methods.

In one embodiment, the aminosterol is Aminosterol 1436 or a squalamine isomer. In yet another embodiment of the invention, the aminosterol is a derivative of squalamine or another naturally occurring aminosterol modified through medical chemistry to improve biodistribution, ease of administration, metabolic stability, or any combination thereof. In another embodiment, the aminosterol (e.g., squalamine or aminosterol 1436) is modified to include one or more of the following: (1) substitutions of the sulfate by a sulfonate, phosphate, carboxylate, or other anionic moiety chosen to circumvent metabolic removal of the sulfate moiety and oxidation of the cholesterol side chain; (2) replacement of a hydroxyl group by a non-metabolizable polar substituent, such as a fluorine atom, to prevent its metabolic oxidation or conjugation; and (3) substitution of various ring hydrogen atoms to prevent oxidative or reductive metabolism of the steroid ring system.

In yet another embodiment, the aminosterol comprises a sterol nucleus and a polyamine, attached at any position on the sterol, such that the molecule exhibits a net charge of at least +1, the charge being contributed by the polyamine.

In yet another embodiment, the aminosterol comprises a bile acid nucleus and a polyamine, attached at any position on the bile acid, such that the molecule exhibits a net positive charge being contributed by the polyamine.

In some embodiments, the compositions used in the methods of the invention comprise: (a) at least one pharmaceutical grade aminosterol; and optionally (b) at least one phosphate selected from the group consisting of an inorganic phosphate, an inorganic pyrophosphate, and an organic phosphate. In some embodiments, the aminosterol is formulated as a weakly water soluble salt of the phosphate. In some embodiments, the phosphate is an inorganic polyphosphate, and the number of phosphates can range from about 3 (tripolyphosphate) to about 400, or any number in-between these two values. In other embodiments, the phosphate is an organic phosphate which comprises glycerol 2 phosphates.

In some embodiments, the aminosterol is selected from the group consisting of: (a) squalamine or a pharmaceutically acceptable salt or derivative thereof; (b) a squalamine isomer; (c) Aminosterol 1436; (d) an aminosterol comprising a sterol or bile acid nucleus and a polyamine, attached at any position on the sterol or bile acid, such that the molecule exhibits a net charge of at least +1, the charge being contributed by the polyamine; (e) an aminosterol which is a derivative of squalamine modified through medical chemistry to improve biodistribution, ease of administration, metabolic stability, or any combination thereof; (f) an aminosterol modified to include one or more of the following: (i) substitutions of the sulfate by a sulfonate, phosphate, carboxylate, or other anionic moiety chosen to circumvent metabolic removal of the sulfate moiety and oxidation of the cholesterol side chain; (ii) replacement of a hydroxyl group by a non-metabolizable polar substituent, such as a fluorine atom, to prevent its metabolic oxidation or conjugation; and (iii) substitution of various ring hydrogen atoms to prevent oxidative or reductive metabolism of the steroid ring system; (g) an aminosterol that can inhibit the formation of actin stress fibers in endothelial cells stimulated by a ligand known to induce stress fiber formation, having the chemical structure of Formula I (above); or (h) any combination thereof.

In some embodiments, the aminosterol can be composed of a sterol or bile acid nucleus to which a polyamine is chemically linked, displaying a net positive charge of at least +1. The methods can be embodied in a formulation comprising a phosphate suspension or as a tablet for oral administration. As an oral formulation, squalamine phosphate (or another aminosterol phosphate) slowly dissolves in the gastrointestinal tract, and does not subject the lining of the intestine to high local concentrations that would otherwise irritate or damage the organ.

In some embodiment, the methods of the invention can employ a formulation of an aminosterol such as squalamine or Aminosterol 1436 as an insoluble salt of phosphate, polyphosphate, or an organic phosphate ester.

Any pharmaceutically acceptable salt of an aminosterol can be used in the compositions and methods of the invention. For example, a phosphate salt or buffer, free base, succinate, phosphate, mesylate or other salt form associated with low mucosal irritation can be utilized in the methods and compositions of the invention.

B. Routes of Administration

It is appreciated that the "fixed dose" disclosed herein can be administered via any suitable route of administration, including but not limited to oral or intranasal delivery, injection (IP, IV, or IM), or a combination thereof.

Further, co-administration of the "fixed dose" with injectable (e.g., 1P, IV, IM) aminosterol formulations is also contemplated herein. For injectable dosage forms, the dosage form can comprise an aminosterol at a dosage of, for example, about 0.1 to about 20 mg/kg body weight. In other embodiments, the effective daily dosing amount is about 0.1, about 0.5, about 1, about 2, about 3, about 4, about 5, about 6, about 7, about 8, about 9, about 10, about 11, about 12, about 13, about 14, about 15, about 16, about 17, about 18, about 19, or about 20 mg/kg body weight.

The invention also encompasses methods of treatment using a combination of an aminosterol composition administered via one route, e.g., oral, with a second aminosterol composition, comprising the same or a different aminosterol, administered via a different route, e.g., intranasal. For example, in a method of the invention, squalamine can be administered orally and aminosterol 1436 can be administered IN.

C. Composition Components

In some embodiments, a pharmaceutical composition disclosed herein comprises one or more pharmaceutically acceptable carriers, such as an aqueous carrier, buffer, and/or diluent.

The aminosterol may be combined or coordinately administered with a suitable carrier or vehicle depending on the route of administration. As used herein, the term "carrier" means a pharmaceutically acceptable solid or liquid filler, diluent or encapsulating material. A water-containing liquid carrier can comprise pharmaceutically acceptable additives such as acidifying agents, alkalizing agents, antimicrobial preservatives, antioxidants, buffering agents, chelating agents, complexing agents, solubilizing agents, humectants, solvents, suspending and/or viscosity-increasing agents, tonicity agents, wetting agents or other biocompatible materials. A tabulation of ingredients listed by the above categories can be found in the U.S. Pharmacopeia National Formulary, 1857-1859, and (1990). Some examples of the materials which can serve as pharmaceutically acceptable carriers are sugars, such as lactose, glucose and sucrose; starches such as corn starch and potato starch; cellulose and its derivatives such as sodium carboxymethyl cellulose, ethyl cellulose and cellulose acetate; powdered tragacanth; malt; gelatin; talc; excipients such as cocoa butter and suppository waxes; oils such as peanut oil, cottonseed oil, safflower oil, sesame oil, olive oil, corn oil and soybean oil; glycols, such as propylene glycol; polyols such as glycerin, sorbitol, mannitol and polyethylene glycol; esters such as ethyl oleate and ethyl laurate; agar; buffering agents such as magnesium hydroxide and aluminum hydroxide; alginic acid; pyrogen free water; isotonic saline; Ringer's solution, ethyl alcohol and phosphate buffer solutions, as well as other nontoxic compatible substances used in pharmaceutical formulations. Wetting agents, emulsifiers and lubricants such as sodium lauryl sulfate and magnesium stearate, as well as coloring agents, release agents, coating agents, sweetening, flavoring and perfuming agents, preservatives and antioxidants can also be present in the compositions, according to the desires of the formulator. Examples of pharmaceutically acceptable antioxidants include water soluble antioxidants such as ascorbic acid, cysteine hydrochloride, sodium bisulfite, sodium metabisulfite, sodium sulfite and the like; oil-soluble antioxidants such as ascorbyl palmitate, butylated hydroxyanisole (BHA), butylated hydroxytoluene (BHT), lecithin, propyl gallate, alpha-tocopherol and the like; and metal-chelating agents such as citric acid, ethylenediamine tetraacetic acid (EDTA), sorbitol, tartaric acid, phosphoric acid and the like.

In some embodiments, a pharmaceutical composition disclosed herein further comprises a simple polyol compound, such as glycerin. Other examples of polyol compounds include sugar alcohols. In some embodiments, a pharmaceutical composition disclosed herein comprises an aqueous carrier and glycerin at about a 2:1 ratio.

Pharmaceutical compositions according to the invention may also comprise one or more binding agents, filling agents, lubricating agents, suspending agents, sweeteners, flavoring agents, preservatives, buffers, wetting agents, disintegrants, effervescent agents, and other excipients. Such excipients are known in the art. Examples of filling agents include lactose monohydrate, lactose anhydrous, and various starches; examples of binding agents include various celluloses and cross-linked polyvinylpyrrolidone, microcrystalline cellulose, such as Avicel® PH101 and Avicel® PH102, microcrystalline cellulose, and silicified microcrystalline cellulose (ProSolv SMCC™). Suitable lubricants, including agents that act on the flowability of the powder to be compressed, may include colloidal silicon dioxide, such as Aerosil® 200, talc, stearic acid, magnesium stearate, calcium stearate, and silica gel. Examples of sweeteners may include any natural or artificial sweetener, such as sucrose, xylitol, sodium saccharin, cyclamate, aspartame, and acesulfame. Examples of flavoring agents are Magnasweet® (trademark of MAFCO), bubble gum flavor, and fruit flavors, and the like. Examples of preservatives include potassium sorbate, methylparaben, propylparaben, benzoic acid and its salts, other esters of parahydroxybenzoic acid such as butylparaben, alcohols such as ethyl or benzyl alcohol, phenolic compounds such as phenol, or quaternary compounds such as benzalkonium chloride.

Suitable diluents include pharmaceutically acceptable inert fillers, such as microcrystalline cellulose, lactose, dibasic calcium phosphate, saccharides, and/or mixtures of any of the foregoing. Examples of diluents include microcrystalline cellulose, such as Avicel® PH101 and Avicel® PH102; lactose such as lactose monohydrate, lactose anhydrous, and Pharmatose® DCL21; dibasic calcium phosphate such as Emcompress®; mannitol; starch; sorbitol; sucrose; and glucose.

Suitable disintegrants include lightly crosslinked polyvinyl pyrrolidone, corn starch, potato starch, maize starch, and modified starches, croscarmellose sodium, cross-povidone, sodium starch glycolate, and mixtures thereof. Examples of effervescent agents include effervescent couples such as an organic acid and a carbonate or bicarbonate. Suitable organic acids include, for example, citric, tartaric, malic, fumaric, adipic, succinic, and alginic acids and anhydrides and acid salts. Suitable carbonates and bicarbonates include, for example, sodium carbonate, sodium bicarbonate, potassium carbonate, potassium bicarbonate, magnesium carbonate, sodium glycine carbonate, L-lysine carbonate, and arginine carbonate. Alternatively, only the sodium bicarbonate component of the effervescent couple may be present.

The pharmaceutical composition comprising an aminosterol derivatives or salts thereof will be formulated and dosed in a fashion consistent with good medical practice, taking into account the clinical condition of the individual patient, the method of administration, the scheduling of administration, and other factors known to practitioners.

D. Dosage Forms

The formulations may conveniently be presented in unit dosage form and may be prepared by any of the methods well known in the art of pharmacy. Any pharmaceutically acceptable dosage form may be employed in the methods of the invention. An exemplary oral dosage form is a tablet or capsule. An exemplary intranasal dosage form is a liquid or powder nasal spray. A nasal spray is designed to deliver drug to the upper nasal cavity, and can be a liquid or powder formulation, and in a dosage form such as an aerosol, liquid spray, or powder.

For example, the composition can be formulated into a dosage form selected from the group consisting of liquid dispersions, gels, aerosols, lyophilized formulations, tablets, or capsules. In some embodiments, the aminosterol may be incorporated into a dosage form selected from the group consisting of controlled release formulations, fast melt formulations, delayed release formulations, extended release formulations, pulsatile release formulations, and mixed immediate release and controlled release formulations. In some embodiments, the dosage form may comprise a combination of the forgoing formulation options (e.g., a controlled release tablet).

In one embodiment of the invention, the oral dosage form is a liquid, capsule, or tablet designed to disintegrate in either the stomach, upper small intestine, or more distal portions of the intestine with a dissolution rate appropriate to achieve the intended therapeutic benefit.

The aminosterol composition can also be included in nutraceuticals. For instance, the aminosterol composition may be administered in natural products, including milk or milk product obtained from a transgenic mammal which expresses alpha-fetoprotein fusion protein. Such compositions can also include plant or plant products obtained from a transgenic plant which expresses the aminosterol. The aminosterol can also be provided in powder or tablet form, with or without other known additives, carriers, fillers and diluents. Exemplary nutraceuticals are described in Scott Hegenhart, *Food Product Design*, December 1993.

Any pharmaceutical used for therapeutic administration can be sterile. Sterility is readily accomplished by for example filtration through sterile filtration membranes (e.g., 0.2 micron membranes). Any pharmaceutically acceptable sterility method can be used in the compositions of the invention The aminosterol composition will be formulated and dosed in a fashion consistent with good medical practice, taking into account the clinical condition of the individual patient (especially the side effects of treatment with the aminosterol alone), the method of administration, the scheduling of administration, and other factors known to practitioners. The "effective amount" for purposes herein is thus determined by such considerations.

Aminosterol formulations or compositions of the invention may be packaged together with, or included in a kit along with instructions or a package insert. Such instructions or package inserts may address recommended storage conditions, such as time, temperature and light, taking into account the shelf-life of the aminosterol. Such instructions or package inserts may also address the particular advantages of the aminosterol, such as the ease of storage for formulations that may require use in the field, outside of controlled hospital, clinic or office conditions.

The invention also provides a pharmaceutical pack or kit comprising one or more containers filled with one or more aminosterol pharmaceutical compositions disclosed herein. The kits may include, for instance, containers filled with an appropriate amount of an aminosterol pharmaceutical composition, either as a powder, a tablet, to be dissolved, or as a sterile solution. Associated with such container(s) can be a notice in the form prescribed by a governmental agency regulating the manufacture, use or sale of pharmaceuticals or biological products, which notice reflects approval by the agency of manufacture, use or sale for human administration. In addition, the aminosterol or a derivative or salt thereof may be employed in conjunction with other therapeutic compounds.

In other aspects, a kit comprising a nasal spray device as described herein is disclosed. In one aspect, the kit may comprise one or more devices as disclosed herein, comprising a disclosed low dose aminosterol composition, wherein the device is sealed within a container sufficient to protect the device from atmospheric influences. The container may be, for example, a foil, or plastic pouch, particularly a foil pouch, or heat sealed foil pouch. Suitable containers sufficient to adequately protect the device will be readily appreciated by one of skill in the art.

In one aspect, the kit may comprise one or more devices as disclosed herein, wherein the device may be sealed within a first protective packaging, or a second protective packaging, or a third protective packaging, that protects the physical integrity of the product. One or more of the first, second, or third protective packaging may comprise a foil pouch. The kit may further comprise instructions for use of the device. In one aspect, the kit contains two or more devices.

E. Dosing Period

The pharmaceutical composition comprising an aminosterol or a derivative or salt thereof can be administered for any suitable period of time, including as a maintenance dose for a prolonged period of time. Dosing can be done on an as needed basis using any pharmaceutically acceptable dosing regimen. Aminosterol dosing can be no more than 1× per day, once every other day, once every three days, once every four days, once every five days, once every six days, once a week, or divided over multiple time periods during a given day (e.g., twice daily).

In other embodiments, the aminosterol composition can be administered: (1) as a single dose, or as multiple doses over a period of time; (2) at a maintenance dose for an indefinite period of time; (3) once, twice or multiple times; (4) daily, every other day, every 3 days, weekly, or monthly; (5) for a period of time such as about 1, about 2, about 3, or about 4 weeks, about 1, about 2, about 3, about 4, about 5, about 6, about 7, about 8, about 9, about 10, about 11, or about 12 months, about 1 year, about 1.5 years, about 2, about 2.5, about 3, about 3.5, about 4, about 4.5, about 5, about 5.5, about 6, about 6.5, about 7, about 7.5, about 8, about 8.5, about 9, about 9.5, about 10, about 10.5, about 11, about 11.5, about 12, about 12.5, about 13, about 13.5, about 14, about 14.5, about 15, about 15.5, about 16, about 16.5, about 17, about 17.5, about 18, about 18.5, about 19, about 19.5, about 20, about 20.5, about 21, about 21.5, about 22, about 22.5, about 23, about 23.5, about 24, about 24.5, or about 25 years, or (6) any combination of these parameters, such as daily administration for 6 months, weekly administration for 1 or more years, etc.

Yet another exemplary dosing regimen includes periodic dosing, where an effective dose can be delivered once every about 1, about 2, about 3, about 4, about 5, about 6 days, or once weekly.

In a preferred embodiment, the aminosterol dose is taken in the morning, i.e. on an empty stomach preferably within about two hours of waking up and may be followed by a period without food, such as for example about 60 to about 90 minutes. In other embodiments, the aminosterol dose is taken within about 15 min, about 30 min, about 45 min, about 1 hr, about 1.25 hrs, about 1.5 hrs, about 1.75 hrs, about 2 hrs, about 2.25 hrs, about 2.5 hrs, about 2.75 hrs, about 3 hrs, about 3.25 hrs, about 3.5 hrs, about 3.75 hrs, or about 4 hrs within waking up. In yet further embodiments, the aminosterol dose is followed by about period without food, wherein the period is at least about 30 min, about 45 mins, about 60 mins, about 1.25 hrs, about 1.5 hrs, about 1.75 hrs, or about 2 hrs.

Not to be bound by theory, it is believed that since aminosterols have an impact on circadian rhythms, likely due to ENS signaling thereof, taking the aminosterol dose in the morning enables the synchronization of all the autonomic physiological functions occurring during the day. In other embodiments of the invention, the aminosterol dosage is taken within about 15 mins, about 30 mins, about 45 mins, about 1 hour, about 1.25 hrs, about 1.5 hrs, about 1.75 hrs, about 2 hrs, about 2.25 hrs, about 2.5 hrs, about 2.75 hrs, about 3 hrs, about 3.25 hrs, about 3.5 hrs, about 3.75 hrs, or about 4 hrs of waking up. In addition, in other embodiments of the invention, following the aminosterol dosage the subject has a period of about 15 mins, about 30 mins, about 45 mins, about 1 hours, about 1.25 hrs, about 1.5 hrs, about 1.75 hrs, about 2 hrs, about 2.25 hrs, about 2.5 hrs, about 2.75 hrs, or about 3 hours without food.

F. Aminosterol Dosing Regimen

Effective dosing regimens can be based on the dose required to observe a change in sleeping patterns or Circadian rhythm within about 1 day, about 2 days, about 3 days, about 4 days, about 5 days, about 6 days, about 7 day, about 8 days, about 9 days, about 10 days, about 11 days, about 12 days, about 13 days, or about 14 days of the initial administration of the aminosterol. A positive change in sleeping pattern includes a change in the total number of hours of sleep, sleeping at night rather than during the day, a decrease in the number of awakenings during the night, falling asleep more quickly, less thrashing or limb movement, and/or developing a normal Circadian (i.e., diurnal) rhythm.

Repeat dosing regimens may be timed by the rate of clearance of the aminosterol from the intestine. It is assumed that at a certain time after the initial "loading" dose, surface concentrations of the aminosterol will decrease as the substance spreads across the surface of the intestinal walls and progresses distally. For example, the aminosterol-induced response appears to last about 4 days following a single 200 mg oral dose of squalamine or Aminosterol 1436. A second dose on day 4 of about 100 mg, followed by successive doses of about 100 mg every 4 days, would represent one reasonable regimen designed to maintain a steady state surface concentration in the intestine. For the purposes of the current methods, daily dosing may also represent a preferable regimen.

Effective dosing regimens can also be clinically established based on the dose required to observe a change in sleeping pattern or the clinical signs or symptoms of the disclosed sleep disorders.

Failure to elicit an aminosterol-induced CNS response would generally suggest that the dose being administered was inadequate, and would suggest continued titration until the desired CNS response is observed. An effective dose can be considered a dose which induces the desired CNS response or that improves the patient's sleeping pattern or improves, prevents, or ameliorates one or more of the signs or symptoms of the sleep disorder.

In an exemplary embodiment of the invention, a "positive change" in sleeping pattern is defined as a percentage of an increase in the total number of hours of sleep, per day, of about 5%, about 10%, about 15%, about 20%, about 25%, about 30%, about 35%, about 40%, about 45%, about 50%, about 55%, about 60%, about 65%, about 70%, about 75%, about 80%, about 85%, about 90%, about 95%, about 100%, about 125%, about 150%, about 175%, about 200%, about 225%, about 250%, about 275%, about 300%, about 325%, about 350%, about 375%, about 400%, about 425%, about 455%, about 475%, or about 500%.

In another exemplary embodiment of the invention, a "positive change" in sleeping pattern is defined as a decrease in the number of awakenings during the night, such as a decrease of about 5%, about 10%, about 15%, about 20%, about 25%, about 30%, about 35%, about 40%, about 45%, about 50%, about 55%, about 60%, about 65%, about 70%, about 75%, about 80%, about 85%, about 90%, about 95%, or about 100%.

In some embodiments, the subject may experience a reduction in hallucinations, a reduction in arm and leg thrashing and speaking out loud associated with REM behavior disorder (RBD), a reduction of nightmares and vivid dreams associated with RBD, a reduction in delay in sleep onset, later awakening in the morning, a reduction in day time sleepiness, a reduction in clinical or sub-clinical "sleep attacks"(i.e. an irresistible urge to sleep or experiencing narcolepsy with cataplexy), and/or an improvement in memory as a result of better memory consolidation during sleep.

An effective oral dose generally falls between about 1 mg to about 500 mg/day, or any amount in between these two values, as detailed above. Other exemplary oral dosages include, for example, about 25 mg to about 300 mg, about 50 mg to about 350 mg, or about 100 mg to about 300 mg. For instance, an effective dose may be about 1, about 5, about 10, about 15, about 20, about 25, about 30, about 35, about 40, about 45, about 50, about 55, about 60, about 65, about 70, about 75, about 80, about 85, about 90, about 95, about 100, about 105, about 110, about 115, about 120, about 125, about 130, about 135, about 140, about 145, about 150, about 155, about 160, about 165, about 170, about 175, about 180, about 185, about 190, about 195, about 200, about 205, about 210, about 215, about 220, about 225, about 230, about 235, about 240, about 245, about 250, about 255, about 260, about 265, about 270, about 275, about 280, about 285, about 290, about 295, about 300, about 305, about 310, about 315, about 320, about 325, about 330, about 335, about 340, about 345, about 350, about 355, about 360, about 365, about 370, about 375, about 380, about 385, about 390, about 395, about 400, about 425, about 450, about 475, or about 500 mg/day.

Dosing can be done on an as needed basis using any pharmaceutically acceptable dosing regimen. For example, dosing can be once or twice daily, once every other day, once every three days, once every four days, once every five days, once every six days, once a week, or divided over multiple time periods during a given day (e.g., twice daily). Preferred dosing is once per day. The dosing schedule may include administration during the morning, midday, or during the evening, or a combination thereof. Preferred dosing is in the morning after the subject is awake, and before any food has been consumed.

Effective dosing regimens can in part be established by measuring the rate of excretion of the orally or nasally administered aminosterol and correlating this with clinical symptoms and signs (i.e., the changes in the patient's sleep pattern). Exemplary dosing regimens include, but are not limited to: Initiating with a "low" initial daily dose, and gradually increasing the daily dose until a dose is reached that elicits evidence of a CNS response that improves the patient's sleeping pattern or improves, prevents or ameliorates one or more of the signs or symptoms of the sleep disorder. In some embodiments, a "low" dose is from about 10 to about 100 mg per person, and the final effective daily dose may be between about 25 to about 500 mg/day.

Another exemplary dosing regimen includes: Initiating with a "high" initial dose, which necessarily stimulates the enteric nervous system, and reducing the subsequent daily dosing to that required to elicit a clinically acceptable change in sleep pattern or improvement in the sleep disorder, with the "high" daily dose being between about 50 to about 1000 mg/person, and the subsequent lower daily oral dose being between about 25 to about 500 mg/person.

Yet another exemplary dosing regimen includes: Periodic dosing, where an effective dose can be delivered once every about 1, about 2, about 3, about 4, about 5, about 6 days, or once weekly, with the initial dose determined to be capable of eliciting an aminosterol-induced CNS response that improves the patient's sleeping pattern or improves, prevents or ameliorates one or more of the signs or symptoms of the sleep disorder.

Aminosterol dosing (e.g., oral or intranasal) should continue at least until the clinical condition has resolved. To establish the need for continued dosing, treatment can be discontinued and the condition reevaluated. If necessary, aminosterol administration should be resumed. The period of dosing can be, for example, about 1, about 2, about 3, or about 4 weeks; about 1, about 2, about 3, about 4, about 5, about 6, about 7, about 8, about 9, about 10, about 11, or about 12 months; or about 1, about 2, about 3, about 4, or 5 years, or longer.

In some embodiments, treatment of sleep disorders according to the disclosed methods may prevent or to slow the progression or onset of central nervous system (CNS) or neurodegenerative disorders including, but not limited to, Parkinson's disease, Alzheimer's disease, Huntington's chorea and/or Disease, schizophrenia, multiple sclerosis, dementia, degenerative processes associated with aging, dementia of aging, multi-system atrophy (MSA), frontotemporal dementia, autism, progressive nuclear palsy, Guadeloupian Parkinsonism, spinocerebellar ataxia, Amyotorphic Lateral Sclerosis (ALS), Friedreich's ataxia, vascular dementia, Lewy Body dementia or disease, spinal muscular atrophy, supranuclear palsy, fronto temperal dementia, neuropathy of diabetes, peripheral sensory neuropathy, cerebral palsy, epilepsy, diabetic neuropathy, and depression.

In some embodiments, the first or initial "large" dose of aminosterol can be selected from the group consisting of about 25, about 50, about 75, about 100, about 125, about 150, about 175, about 200, about 225, about 250, about 275, about 300, about 325, about 350, about 375, about 400, about 425, about 450, about 475, about 500, about 525, about 550, about 575, about 600, about 625, about 650, about 675, about 700, about 725, about 750, about 775, about 800, about 825, about 850, about 875, about 900, about 925, about 950, about 975, about 1000, about 1025, about 1050, about 1075, about 1100, about 1125, about 1150, about 1175, about 1200, about 1225, about 1250, about 1275, about 1300, about 1325, about 1350, about 1375, about 1400, about 1425, about 1450, about 1475, about 1500, about 1525, about 1550, about 1575, about 1600, about 1625, about 1650, about 1675, about 1700, about 1725, about 1750, about 1775, about 1800, about 1825, about 1850, about 1875, about 1900, about 1925, about 1950, about 1975, or about 2000 mg/day.

In other embodiments of the invention, the second smaller dose of aminosterol is less than the first or initial dose and can be selected from the group consisting of about, 10, about 25, about 50, about 75, about 100, about 125, about 150, about 175, about 200, about 225, about 250, about 275, about 300, about 325, about 350, about 375, about 400, about 425, about 450, about 475, about 500, about 525, about 550, about 575, about 600, about 625, about 650, about 675, about 700, about 725, about 750, about 775, about 800, about 825, about 850, about 875, about 900, about 925, about 950, about 975, or about 1000 mg. Finally, in other embodiments of the invention, the periodic squalamine dosage (per person) can be selected from the group consisting of about 10, about 25, about 50, about 75, about 100, about 125, about 150, about 175, about 200, about 225, about 250, about 275, about 300, about 325, about 350, about 375, about 400, about 425, about 450, about 475, about 500, about 525, about 550, about 575, about 600, about 625, about 650, about 675, about 700, about 725, about 750, about 775, about 800, about 825, about 850, about 875, about 900, about 925, about 950, about 975, and about 1000 mg/day.

Optimal dosing appears to be on an empty stomach. Squalamine, for example, is expected to bind tightly to foodstuff, and be unavailable to interact with the intestinal epithelium. Only as the food material is digested is squalamine freed. Such would be occurring in the more distal intestine.

V. Combination Therapy

The methods of the invention can further comprise administering the aminosterol or pharmaceutically acceptable salt or derivative thereof in combination with at least one additional active agent to achieve either an additive or synergistic effect. Such an additional agent can be administered via a method selected from the group consisting of concomitantly, as an admixture, separately and simultaneously or concurrently, and separately and sequentially.

Thus, the aminosterol compositions may be administered alone or in combination with other therapeutic agents. As noted above, the methods are useful in treating and/or preventing the conditions described herein, including but not limited to sleep disorders with delay in sleep onset, sleep fragmentation, REM-behavior disorder, or hallucinations, and sleep disorders associated with Parkinson's disease, Alzheimer's disease, Huntington's Disease, schizophrenia, multiple sclerosis, and degenerative processes associated with aging. Thus, any active agent known to be useful in treating these conditions can be used in the disclosed, and either combined with the aminosterol compositions used in the methods, or administered separately or sequentially.

For example, in disclosed methods of sleep disorders, the aminosterol composition can be co-administered or combined with drugs commonly prescribed to treat sleep disorders or related symptoms, such as sleeping pills, melatonin supplements, allergy or cold medication, or medications that are prescribed to treat the underlying health issue associated with the sleep disorder (e.g., Parkinson's Disease). Additionally, a patient may use a breathing device or dental guard while undergoing the disclosed aminosterol therapy, or the patient may benefit from cognitive behavioral therapy (CBT) in combination with the disclosed aminosterol therapy.

When combining more than one therapeutic compound for administering according to the disclosed methods, combinations may be administered either concomitantly, e.g., as an admixture; separately but simultaneously or concurrently; or sequentially. This includes presentations in which the combined agents are administered together as a therapeutic mixture, and also procedures in which the combined agents are administered separately but simultaneously, e.g., as through separate intravenous lines or in separate pills/tablets into the same individual. Administration "in combination" further includes the separate administration of one of the compounds or agents given first, followed by the second.

VI. Definitions

The following definitions are provided to facilitate understanding of certain terms used throughout this specification.

Technical and scientific terms used herein have the meanings commonly understood by one of ordinary skill in the art, unless otherwise defined. Any suitable materials and/or methodologies known to those of ordinary skill in the art can be utilized in carrying out the methods described herein.

As used in the description of the invention and the appended claims, the singular forms "a", "an" and "the" are used interchangeably and intended to include the plural forms as well and fall within each meaning, unless the context clearly indicates otherwise. Also, as used herein, "and/or" refers to and encompasses any and all possible combinations of one or more of the listed items, as well as the lack of combinations when interpreted in the alternative ("or").

As used herein, "about" will be understood by persons of ordinary skill in the art and will vary to some extent on the context in which it is used. If there are uses of the term which are not clear to persons of ordinary skill in the art given the context in which it is used, "about" will mean up to plus or minus 10% of the particular term.

As used herein the term "aminosterol" encompasses squalamine or a pharmaceutically acceptable salt or derivative thereof, an isomer or prodrug of squalamine, Aminosterol 1436 or a pharmaceutically acceptable salt or derivative thereof, an isomer or prodrug of Aminosterol 1436, or a naturally occurring aminosterol isolated from *Squalus acanthias* or a derivative thereof, as described herein. "Aminosterols" useful in the invention also encompass a pharmaceutically equivalent salt of any aminosterol compound described herein. These compounds, and pharmaceutically acceptable salts thereof, are collectively referred to herein as "squalamine" and "aminosterols." Thus, the term "aminosterol" as used herein is intended to encompass the broader class that includes both squalamine and the known naturally occurring aminosterols.

As used herein, the phrase "therapeutically effective amount" means a dose that provides the specific pharmacological effect for which the compound or compounds are being administered. It is emphasized that a therapeutically effective amount will not always be effective in achieving the intended effect in a given subject, even though such dose is deemed to be a therapeutically effective amount by those of skill in the art. For convenience only, exemplary dosages are provided herein. Those skilled in the art can adjust such amounts in accordance with standard practices as needed to treat a specific subject. The therapeutically effective amount may vary based on the route of administration and dosage form, the age and weight of the subject, and/or the severity of the subject's condition. For example one of skill in the art would understand that the therapeutically effective amount for treating a small individual may be different from the therapeutically effective amount for treating a large individual. In the context of treating sleep disorders, the type of sleep disorder and any underlying pathophysiology that contributes to the sleep disorder may have a bearing on the dose needed to therapeutically effective.

The terms "treatment" or "treating" as used herein includes preventing, reducing, ameliorating, or eliminating one or more symptoms or effects of the sleep disorder being treating.

The term "administering" as used herein includes prescribing for administration as well as actually administering, and includes physically administering by the subject being treated or by another.

As used herein "subject" or "patient" or "individual" refers to any subject, patient, or individual, such as a subject suffering from a sleep disorder or a subject that is at risk of developing a sleep disorder, and the terms are used interchangeably herein. In this regard, the terms "subject," "patient," and "individual" includes mammals, and, in particular humans.

The following examples are provided to illustrate the present invention. It should be understood, however, that the invention is not to be limited to the specific conditions or details described in these examples. Throughout the specification, any and all references to a publicly available document, including a U.S. patent, are specifically incorporated by reference.

EXAMPLES

Example 1

An elderly patient with a sleep disorder was treated with squalamine to determine the efficacy of the drug for treating sleep disturbances. The patient was a 78 year old woman with a 10 year history of sleep disturbance and a history of constipation, anxiety, and anosmia for as long as she could remember. Her sleep was profoundly disturbed: she had difficulty falling asleep, awoke 3-4 times during the night, had vivid dreams and nightmares, spoke and screamed out loud during her sleep (REM-behavior disorder, RBD), often saw "apparitions" or people in the room (e.g., a cook in a top hat, priests and angels dressed in white). She slept with a night light on in an attempt to minimize these occurrences.

The patient was treated with oral squalamine (Kenterin™) starting at 100 mg qd and increasing to 200 mg qd. Sleep was monitored indirectly with the use of a temperature sensor (I-button) mounted on a wristband. The sensor was programed to record skin temperature at the wrist every 15 minutes 24 hrs a day. Data were downloaded every few weeks.

As the dose was increased, the patient slept better and longer. "Total hours of sleep" increased from 7.5 hours a night at pre-treatment baseline to 9.1 hours at 200 mg of squalamine daily, e.g., a 21.3% increase in the total amount of sleep. See FIG. 1. The patient's total hours of sleep returned to 7.0 hours following discontinuation of squalamine dosing. Similar responses were seen with alternate day dosing, as shown in the Tables 2 and 3 below and in FIGS. 1 and 2.

TABLE 2

| Regimen (mg) | Total hrs sleep | % Change in Hours (from base) |
| --- | --- | --- |
| pre (0) | 7.5 | — |
| 100 qd | 7.9 | +5.3% |
| 150 qd | 8.8 | +17.3% |
| 200 qd | 9.1 | +21.3% |
| Post (0) | 7.0 | −6.7% |
| 125 qod | 8.7 | +16% from initial pre(0); +24.3% from post (0) |

Figure 2:
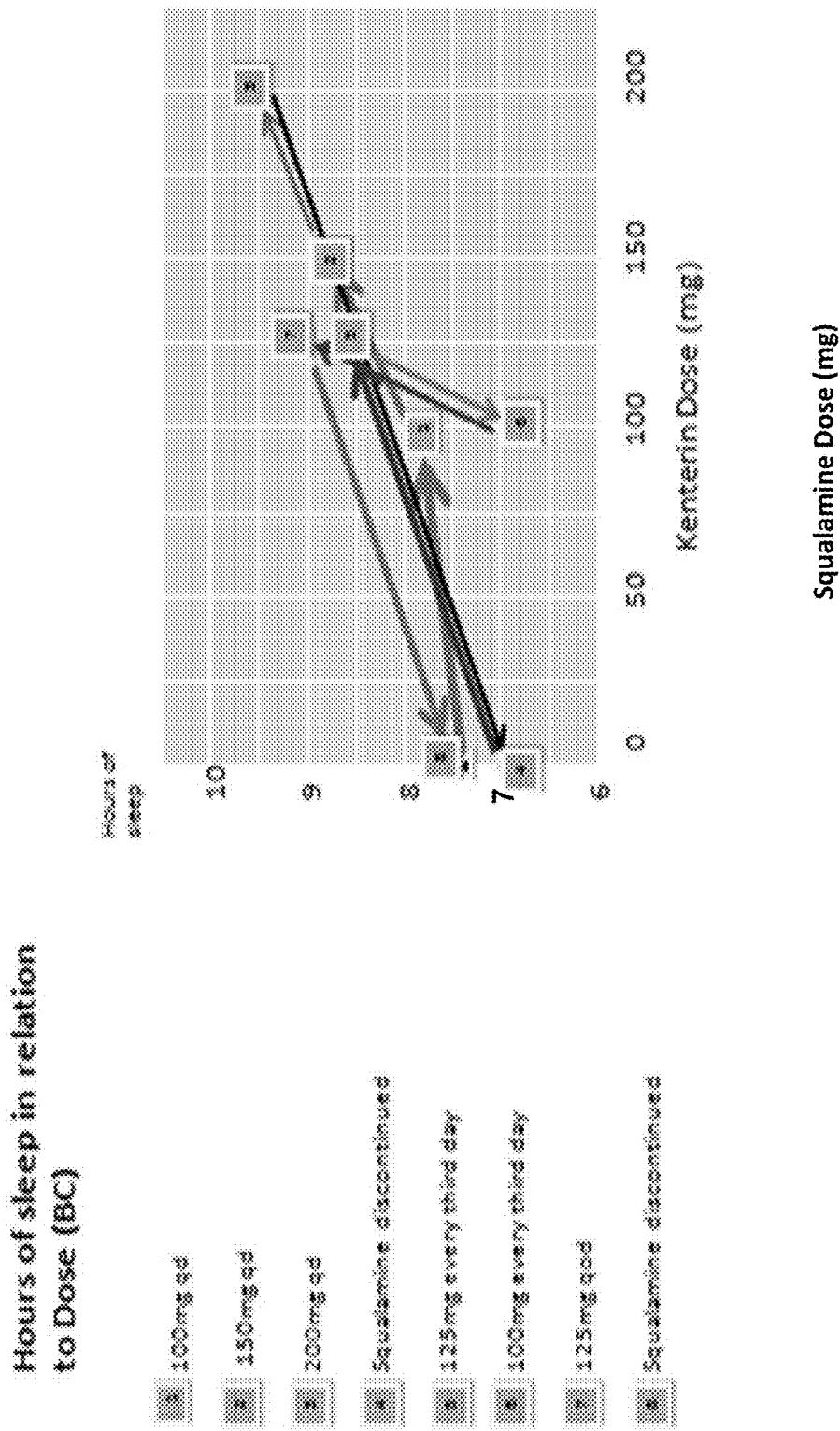
FIG. 2 shows a graph of hours of sleep vs squalamine dose (mg), with the following squalamine doses tested: (1) 100 mg q.d., (2) 150 mg q.d., (3) 200 mg q.d., (4) 125 mg every third day, (5) 100 mg every third day, and (6) 125 mg q.o.d. Measurements #4 and #8 show the number of hours of sleep obtained following discontinuation of squalamine administration; e.g., the results show a dramatic decline in the number of hours of sleep.

Table 2 and FIGS. 1 and 2 show that "total hours of sleep" increases in a dose dependent manner in both directions. In other words, as the dose is increased, the hours of sleep increase, and as the dose was decreased, the hours of sleep decreased. The effect was immediate. Shown in FIG. 2 is the hours of sleep resulting following the following dosing schedule for squalamine: (1) 100 mg q.d., (2) 150 mg q.d., (3) 200 mg q.d., (4) 125 mg every third day, (5) 100 mg every third day, and (6) 125 mg q.o.d. Measurements #4 and #8 show the number of hours of sleep obtained following discontinuation of squalamine administration; e.g., the results show a dramatic decline in the number of hours of sleep. FIG. 2 shows that "total hours of sleep" increased in a dose-dependent manner in both directions and that medicating every 3 days was effective.

Table 3 below shows how the delay in sleep onset was progressively reduced as the squalamine dose was increased. In other words, the patient was falling asleep more easily. The notes also indicate that RBD, as defined by vivid dreams and nightmares and frank visual hallucinations disappeared on treatment, reappeared when medication was discontinued and disappeared again when it was reinstated. Thus, not only does squalamine decrease delay in sleep onset and increase total sleep time, but it also has an effect on RBD and hallucinations, both of which occur as a result of Circadian rhythm dysfunction. Table 3, which is a daily sleep diary, shows normalization of the circadian rhythm in this individual as a result of squalamine treatment.

TABLE 3

| Day # | Time to bed/to sleep | Delay (min) | Fragments awake (min) | Wake up time/ Alarm (A) | Total hrs sleep | Notes |
|---|---|---|---|---|---|---|
| 1 | 10/10.15 | 15 | 15 | 7.0 | 8.75 | baseline |
| 2 | 10/10.20 | 20 | 20 | 6.30 | 7.75 | |
| 3 | 11/11.15 | 15 | | 6.0 | 4.75 | I-button |
| 4 | 10/10.30 | 30 | 30 | 6.0 | 7.0 | |
| 5 | 11/11.15 | 15 | 15 | 7.0 | 7.5 | |
| 6 | 10/10.15 | 15 | 15 | 7.0 | 8.50 | |
| 7 | 10/10.30 | 30 | 15 | 7.0 | 7.25 | |
| 8 | 10.15/10.35 | 20 | 15 | 7.15 | 8.25 | |
| 9 | 10/10.30 | 30 | 20 | 7.25 | 8.25 | |
| 10 | 10/10.15 | 15 | 20 | 6.45 | 7.25 | |
| 11 | 9.30/9.50 | 20 | 30 | 6.15 | 7.25 | |
| 12 | 10/10.30 | 30 | 20 | 7.0 | 8.50 | |
| 13 | 10/10.30 | 30 | 20 | 7.0 | 7.0 | |
| Mean pre | | 22 | 20 | | 7.5 | |
| 14 | 10/10.20 | 20 | 20 | 7.0 | 8.75 | Nausea diarrhea at 3.25 hrs |
| 15 | 10.30/10.45 | 15 | 20 | 7.15 | 8.50 | N+ Dx2 at 3 and 5 hrs |
| 16 | 10/10.20 | 20 | 15 | 7.0 | 8.50 | – |
| 17 | 10/10.15 | 15 | 20 | 7 | 8.50 | – |
| 18 | 10/10.30 | 30 | 30 | 5.30 | 6.50 | massive |
| 19 | 10/10.30 | 30 | 30 | 5.30 | 6.50 | |
| 20 | 10.30/11 | 30 | 20 | 6.15 | 7 | |
| 22 | 10/10.20 | 20 | 20 | 6 | 7.75 | Travel without ibutton |
| 23 | 10/10.20 | 20 | 30 | 6.30 | 6.5 | Energy ++ |
| 24 | 10.30/11 | 30 | 20 | 7 | 7.5 | Energy ++ |
| 25 | 10/10.20 | 20 | 20 | 6 | 7.5 | Energy ++ |
| 26 | 11/11.20 | 20 | 20 | 6.30 | 6.5 | Energy ++ |
| 27 | | | | | | Energy ++ |
| 28 | 10/10.20 | 20 | 20 | 6.30 | 7.75 | Energy ++ |
| 29 | 10.30/10.50 | 20 | 20 | 6.30 | 7.50 | Energy ++ |
| 30 | 10.30/10.45 | 15 | 20 | 6 | 7.50 | Energy ++ |
| 31 | 10/10.15 | 15 | 20 | 7 | 8.50 | Energy ++ |
| 32 | 10/10.15 | 15 | | 7 | 8.5 | |
| 33 | 10/10.10 | 10 | 10 | 7 | 8.5 | |
| 34 | 10/10.10 | 10 | 10 | 7 | 8.75 | |
| 35 | 10/10.10 | 10 | 10 | 6.30 | 8.25 | |
| 36 | 10/10.10 | 10 | 10 | 7 | 8.75 | |
| 37 | 10/10.10 | 10 | 10 | 7 | 8.75 | |
| 38 | 10.30/10.40 | 10 | 10 | | 7 | |
| 39 | 10/10.10 | 10 | 10 | 6.30 | 8.25 | |
| 40 | 10/10.10 | 10 | 10 | 7 | 8.5 | |
| 41 | 10/10.10 | 10 | 10 | | 7 | |
| 42 | 11/11.20 | 20 | 20 | 7 | 7.50 | |
| 43 | 10/10.10 | 10 | 10 | 7 | 8.75 | |
| 44 | 10/10.10 | 10 | 10 | 7 | 8.75 | |
| 45 | 8/8.30 | 30 | 120 | 5.30 | 6.50 | Back from Europe |
| 46 | 9/9.30 | 30 | 20 | 6 | 8.25 | |
| 47 | 9/9.10 | 10 | 10 | 7 | 9.75 | |
| Mean 100* | | 17 | 20 | | 7.9 | 100 mg |
| 48 | | | | | | 125 mg |
| 49 | | | | | | 125 mg |
| Mean 125* | | | | | | |
| 50 | | | | | | 150 mg |
| 51 | | | | | | 175 mg |
| 52 | | | | | | 175 i-button restarted |
| 53 | 11/11.20 | 20 | 15 | 7 | 9.0 | 175 |
| 54 | 9.30/9.50 | 20 | 15 | 7 | 9.0 | 200 |
| 55 | 9/9.20 | 20 | 30 | 7 | 9.25 | 200 |
| Mean 200 | | 20 | 20 | | 9.1 | |
| 56 | | | | | | 150 |
| 57 | | | | | | 150 |
| 58 | | | | | | 150 |

TABLE 3-continued

| Day # | Time to bed/to sleep | Delay (min) | Fragments awake (min) | Wake up time/ Alarm (A) | Total hrs sleep | Notes |
|---|---|---|---|---|---|---|
| 59 | | | | | | 150 |
| 60 | | | | | | 150 |
| 61 | | | | | | 150 |
| 62 | 10.30/11 | 30 | 30 | 6 | 5.0 | STOP |
| 63 | 10/10.30 | 30 | 30 | 6 | 5.0 | |
| 64 | 9/9.20 | 20 | 30 | 8.30 | 10.25 | |
| 65 | 10/10.30 | 30 | 20 | 7 | 6.25 | Apparitions |
| 66 | 10/10.30 | 30 | 20 | 7 | 8.0 | Apparitions |
| 67 | 9.30/10.15 | 45 | 30 | 7 | 8.0 | Apparitions, severely disturbed sleep |
| 68 | | | | | | Halluc ++ |
| Mean | | 30 | 30 | | 7.0 | |
| 69 | 10.30/10.50 | 20 | 30 | 7 | 8.0 | START 125 mg q3/7 Less dizzy (changed PD meds) great sleep. Energy great |
| 70 | 9/9.20 | 20 | 20 | 7 | 9.50 | Energy great |
| 71 | 10/10.30 | 30 | 20 | 7 | 8.25 | suppos |
| 72 | 9/9.30 | 30 | 20 | 7 | 9.25 | Kenterin125 |
| 73 | 8.30/9 | 30 | 20 | 7 | 10.25 | Energy great |
| 74 | 11/11.30 | 30 | 20 | 6.30 | 7.75 | suppos |
| 75 | 10/10.30 | 30 | 20 | 6.30 | 7.75 | Kenterin 125 Energy great |
| 76 | 10/10.20 | 20 | 15 | 7 | 8.5 | – |
| 77 | 9.30/9.50 | 20 | 20 | 7 | 9.25 | – |
| 78 | 9/9.20 | 20 | 20 | 7 | 9.5 | Kenterin 125 |
| 79 | 9/9.20 | 20 | 20 | 7 | 9.5 | – |
| 80 | 9.30/10 | 30 | 60 | 6 | 7.5 | – |
| Mean 125 q3d | | 25 | 24 | | 8.75 | |
| 81 | 10/10.30 | 30 | 40 | 6 | 6.75 | Kenterin 100 |
| 82 | 10/10.30 | 30 | 40 | 6 | 6.75 | – |
| 83 | 10/10.30 | 30 | 30 | 6 | 7 | – |
| Mean 100q3 | | 30 | 36 | | 6.8 | |
| 84 | | | | | | Kenterin 125 alternate days + |
| 85 | 10/10.20 | 20 | 20 | 7 | 8.50 | – |
| 86 | 9/9.20 | 20 | 20 | 8 | 10.50 | + |
| 87 | 9/9.20 | 20 | 20 | 7.30 | 9 | – |
| 88 | 9.30/9.50 | 20 | 20 | 7 | 9 | + |
| 89 | 9.30/9.40 | 10 | 20 | 7 | 9 | – |
| 90 | 10/10.20 | 20 | 20 | 6.45 | 8.5 | + |
| 91 | 9.30/9.40 | 10 | 20 | 7 | 9.25 | – |
| 92 | 10/10.20 | 20 | 20 | 7.30 | 8.75 | + |
| 93 | 9.30/9.50 | 20 | 20 | 7 | 8.75 | – |
| 94 | 10/10.20 | 20 | 30 | 7 | 8.25 | + |
| 95 | 9/9.20 | 20 | 60 | 8 | 9.75 | – |
| 96 | 9.30/10 | 30 | 30 | 8.30 | 10 | + |
| 97 | 9.30/9.40 | 10 | 20 | | | – |
| 98 | 9/9.20 | 20 | 30 | 6.30 | 8.5 | + |
| 99 | 9/9.20 | 20 | 20 | 7 | 9.5 | – |
| Mean 125 qod | | 19 | 25 | | 9.1 | |
| 100 | 9.30/9.45 | 15 | 45 | 7 | 9 | + |
| 101 | 9.30/9.5 | 20 | 20 | 6.30 | 8.5 | – |
| 102 | 10/10.20 | 20 | 120 | 7 | 7.75 | + |
| 103 | 9/9.15 | 15 | 60 | 8.30 | 10 | – |
| 104 | 10/10.15 | 15 | 20 | 7.30 | 9.5 | + |
| Mean 150 qod | | 17 | 53 | | 8.95 | |
| 105 | | | | | | – |
| 106 | 8.30/8.40 | 10 | 20 | 7 | 10 | – |
| 107 | 9/9.10 | 10 | 20 | 7 | 9.50 | + |
| 108 | 9/9.10 | 10 | 20 | 7 | 10 | – |
| 109 | 9.30/9.45 | 15 | 20 | 8.55 | 8.75 | – |
| 110 | 8.30/8.50 | 20 | 20 | 7 | 9.75 | + |
| 111 | 10/10.20 | 20 | 45 | 7 | 8 | – |
| Mean 150 q3d | | 14 | 24 | | 9.3 | |
| 112 | 9/9.30 | 30 | 45 | 7.30 | 9.25 | – |
| 113 | 9/9.20 | 20 | 20 | 8.30 | 10.75 | – |
| 114 | 10/10.30 | 30 | 20 | 7 | 8 | – Didn't take |
| 115 | 9.30/9.40 | 10 | 10 | 7 | 9 | – |
| 116 | 9.30/9.50 | 20 | 30 | 7 | 9 | – |

TABLE 3-continued

| Day # | Time to bed/to sleep | Delay (min) | Fragments awake (min) | Wake up time/Alarm (A) | Total hrs sleep | Notes |
|---|---|---|---|---|---|---|
| 117 | 10/10.10 | 10 | 20 | 7 | 8.5 | – |
| 118 | 9.30/9.45 | 15 | 20 | 7 | 9 | |
| 119 | 9.15/9.30 | 15 | 20 | 7 | 9.25 | |
| 120 | 9/9.20 | 20 | 20 | 7 | 9.25 | |
| 121 | 9/9.20 | 20 | 20 | 7 | 9 | |
| 122 | 9/9.20 | 20 | 20 | 7 | 9 | |
| 123 | 9/9.20 | 20 | 20 | 7 | 9 | |
| 124 | 9/9.50 | 20 | 60 | 4.30 | 5.5 | |
| 125 | 9/9.40 | 40 | 90 | 4 | 4.5 | |
| 126 | 9/9.20 | 20 | 90 | 4.30 | 5.5 | |
| 127 | 9/9.20 | 20 | 120 | 4.30 | 5 | |
| 128 | 9.3/9.5 | 20 | 90 | 4 | 5.5 | Since stopping Kenterin, sleep poor, awakes 4 am can't get back to sleep, talks in the night, less sharp, less pep, sleeping more during the day |
| 129 | 10.3/10.4 | 10 | 30 | 4.30 | 5.25 | nightmare |
| 130 | 8.30/8.50 | 20 | 60 | 4.30 | 6.30 | |
| 131 | 9/9.30 | 20 | 20 | 7.30 | 9 | |
| 132 | 9/9.2 | 20 | 20 | 7 | 9.75 | nightmare |
| 133 | 9/9.2 | 20 | 20 | 7 | 9.5 | |
| 134 | 10/10.20 | 20 | 60 | 4 | 4.5 | |
| 135 | 10/10.30 | 30 | 20 | 7.15 | 8.5 | Walking worse |
| Mean off K | | 20 | 39 | | 7.8 | |

The daily sleep diary in Table 3 shows that as the dose is increased, the "delay in sleep onset" is progressively reduced and the total hours of sleep are increased. The comments also indicate that RBD, as defined by vivid dreams, nightmares and visual hallucinations, disappear on treatment, reappear when medication is discontinued, and disappear again when it is reinstated.

Figure 3:
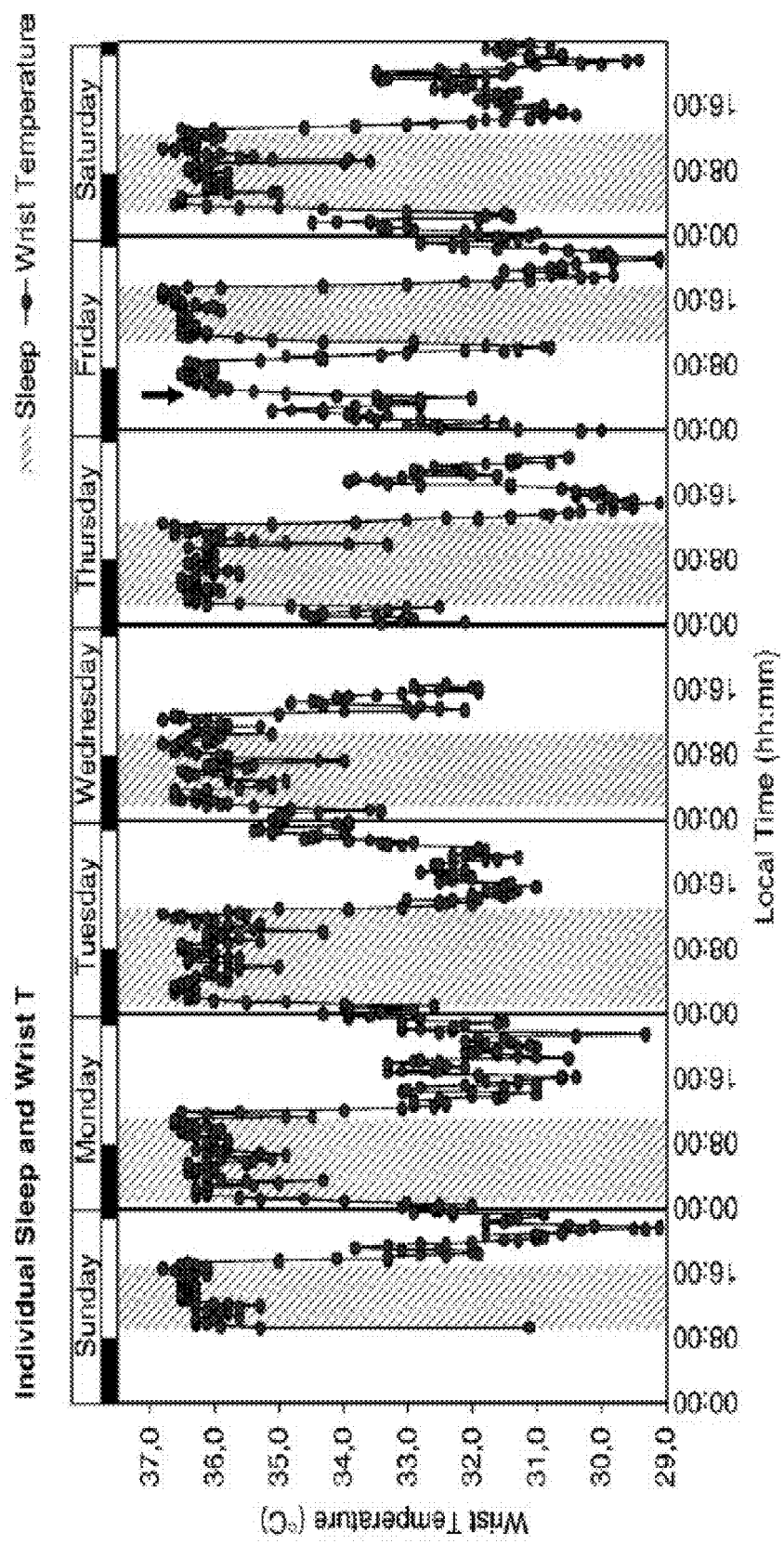
FIG. 3 shows that the results of a measurement of wrist temperature (° C.) vs time. The recording shows normal Circadian rhythm. In a normal individual, skin temperature increases to 36° C. at night and remains there throughout the night, falling precipitously in the morning, remaining at 32° C. or below throughout the day. Skin temperature is measured using a temperature sensor such as an I-button. The diurnal variation in skin temperature correlates closely with the sleep wake cycle and can be used as a surrogate measure of sleep.

The temperature recording shown in FIG. 3 is from an individual with a normal Circadian rhythm. The patient's skin temperature increased to 36° C. at night and remained there while sleeping. In the morning, the patient's skin temperature fell, remaining at 32° C. or below during the day, which is consistent with a normal Circadian rhythm. Skin temperature was measured using an I-button and the diurnal variation in temperature correlates with sleep wake cycles.

Figure 4A:
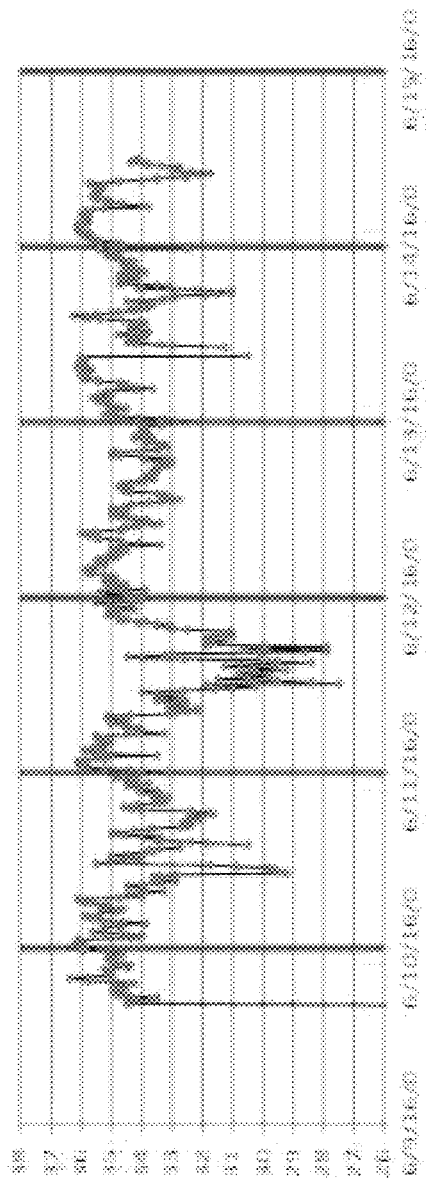
FIGS. 4A and 4B show a patient with a complete absence of diurnal rhythm. Prior to beginning treatment, this patient had a complete absence of diurnal rhythm, as shown in the top panel I-button recording (FIG. 4A). The bottom panel (FIG. 4B) shows a corresponding lack of a peak, indicating a lack of diurnal rhythm.
Figure 4B:
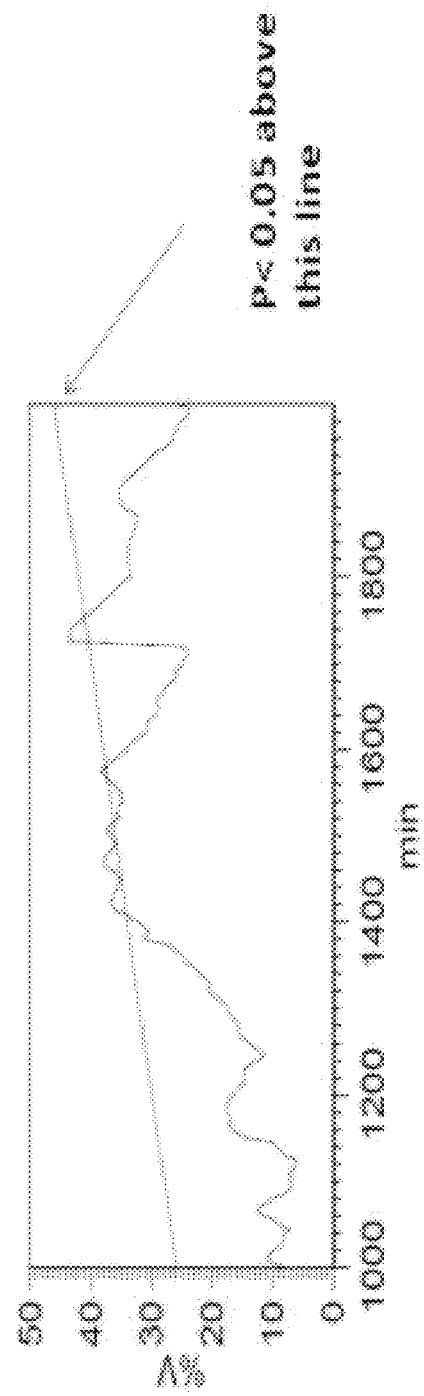

The data shown in FIG. 4 were obtained at baseline. The recording (FIG. 4A) shows a profound disturbance of the diurnal rhythm (FIG. 4A recording is skin temperature obtained using the I-button). The periodogram (FIG. 4B) shows a corresponding lack of a "peak" above the line of significance, confirming the lack of circadian rhythmicity. Thus, the data obtained from this patient shows a total absence of diurnal rhythm prior to treatment.

Figure 5A:
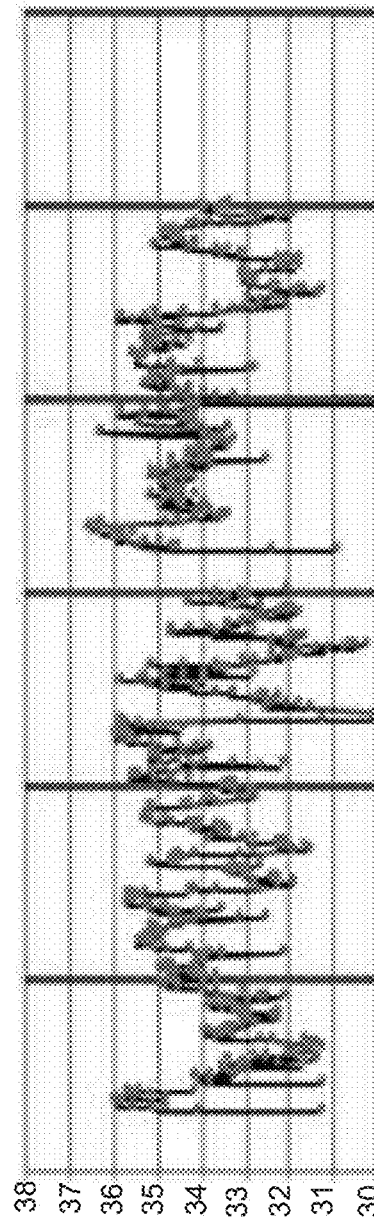
FIGS. 5A, 5B, and 5C show the first week of treatment with squalamine in a patient with sleep disturbance. The I-button recording in the top panel (FIG. 5A) shows that diurnal rhythm was not achieved after one week. Indeed, the bottom, left panel (FIG. 5B) shows that the patient did not have a peak on her periodogram, which is considered normal. A normal periodogram peak is shown in the bottom, right panel (FIG. 5C).
Figure 5C:
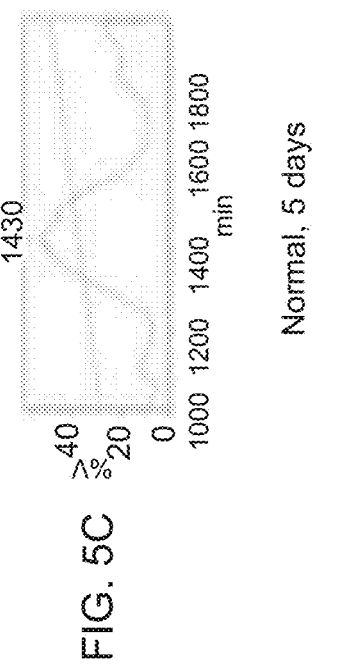
Figure 5B:
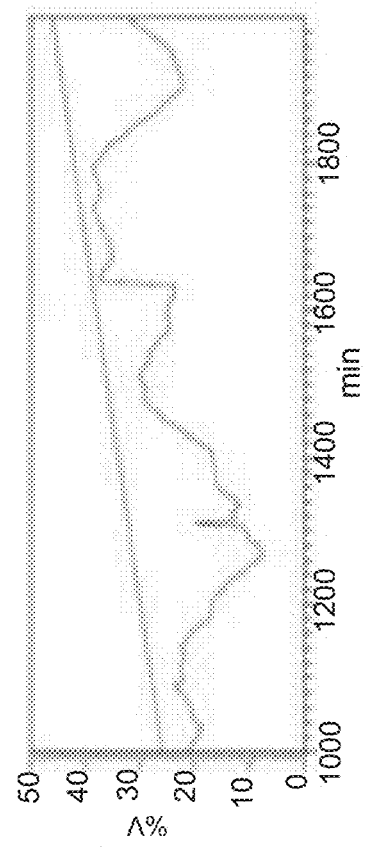

After the first week of treatment, the circadian rhythm is still absent in this patient (FIG. 5a) and there is no "peak" on the periodogram (FIG. 5B). In contrast, a normal periodogram, which is shown in FIG. 5C, shows a "peak."

Figure 6A:
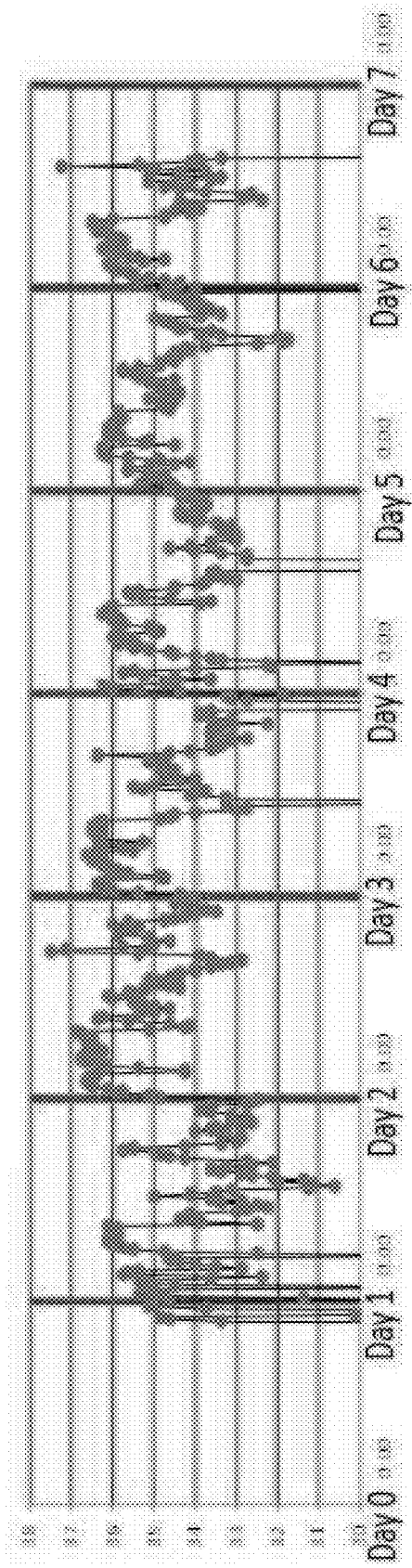
FIGS. 6A and 6B show the effects on diurnal rhythm in an individual that received intermittent administration of squalamine over the course of several months. The top panel (FIG. 6A) shows an I-button temperature recording, indicating that a normal diurnal rhythm was achieved after a few months, and the periodogram in the bottom panel (FIG. 6B) illustrates that the patient's peak appears normal.
Figure 6B:
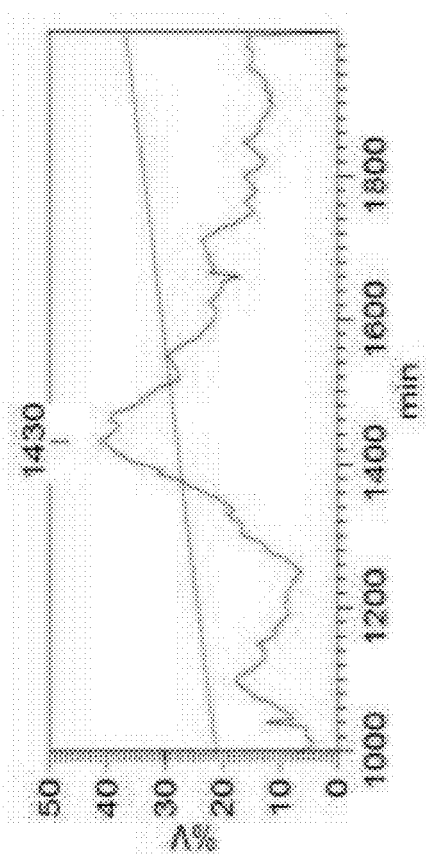

After intermittent treatment for several months, some diurnal rhythmicity was restored, best seen in the last three days of recording in FIG. 6A Similarly a "peak" was apparent at that time in the periodogram in FIG. 6B, which was very similar to what would be expected in a normal individual.

Figure 7:
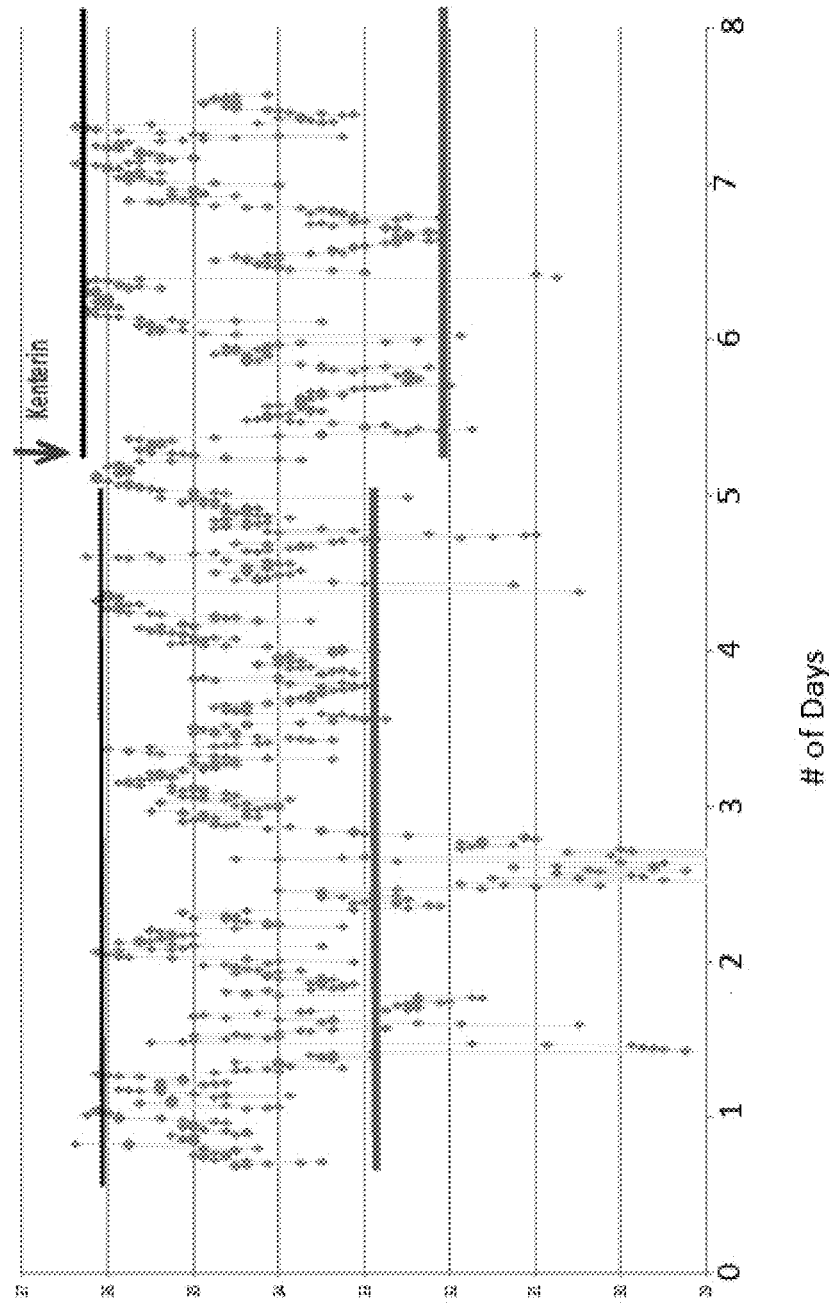
FIG. 7 shows an I-button recording from an individual that indicates that a normal diurnal rhythm can be restored almost immediately when a patient begins receiving an appropriate dose of squalamine.

The I-button recording in FIG. 7 shows that the diurnal rhythm was restored almost immediately after an appropriate dose of squalamine was administered.

Example 2

An 82 year old patient had a 20 year history of sleeping disorder and life-long constipation. The patient had very significant delay in sleep onset, fragmented sleep, thrashing of arms and legs (RBD) and daytime somnolence. On polysomnography, he had apneic spells up to 17 seconds in duration with an oxygen desaturation as low as 93%. The patient slept no more than 3-4 hours, awakened 3-4 times, and each awakening lasted 30-60 minutes. Medications included clonazepam and laxatives.

Clonazepam and laxatives were discontinued and he was started on 100 mg of squalamine every other day at bedtime. This regimen had no effect on his sleep or constipation. The squalamine dose was then increased to 150 mg daily at bedtime, without effect. He was then switched to 150 mg daily taken in the morning. At that dose, his bowels regularized almost immediately, his arms and legs stopped thrashing in the night, his total sleep time increased, he started falling asleep much sooner, and he spent more of the night asleep (sleep efficiency increased). The patient's sleep diary is shown in Table 4 below.

TABLE 4

| Day # | Time to bed/to sleep | Delay (min) | Fragments awake (min) | Wake up time/Alarm (A) | Total hrs sleep | SE (%) | Sleep age (yrs) | Leg thrashing | Notes |
|---|---|---|---|---|---|---|---|---|---|
| 1 | | – | – | | 5.5 | | | | |
| 2 | 12/— | – | – | 8.30 | 7.0 | | | | |
| 5 | 1.15/— | – | 105 | 9.45 | 6.45 | 79 | | | poor |

TABLE 4-continued

| Day # | Time to bed/to sleep | Delay (min) | Fragments awake (min) | Wake up time/Alarm (A) | Total hrs sleep | SE (%) | Sleep age (yrs) | Leg thrashing | Notes |
|---|---|---|---|---|---|---|---|---|---|
| 6 | 12/3 | 180 | – | 9.15 | 6.15 | 67 | | | |
| 7 | 11.45/— | – | – | | 5.30 | | | | |
| 9 | —/2 | – | – | 10.30 | 5.0 | | | + | |
| 12 | 12/1.45 | 105 | 45 | 10 | 7.30 | 75 | | | poor |
| 14 | 12/— | -- | – | | | 5.30 | | | |
| 15 | —/— | – | -- | | 5.30 | | | | |
| 19 | 11.15/— | – | – | | 5.30 | | | | |
| 20 | - | – | – | | 5.30 | | | | |
| 21 | - | | | 9.0 | 5.5 | | | | poor |
| 22 | 11/2 | 180 | | 11.0 | 9.0 | 75 | | + | – |
| 23 | 11/12.30 | 120 | 120 | 10 | 7.30 | | | | |
| 25 | —/12.30 | – | 90 | 7.30A | 5.30 | | | | poor |
| mean | | 146 | 90 | | 6.2 | 74 | 70-80 | | |
| 28 am dose | 11.45/11.45 | 0 | 20 | 7.45A | 7.75 | 96 | | – | BETTER |
| 29 | 11/12.30 | 90 | 20 | 8.30A | 7.75 | 81 | | | N |
| 30 | 1/4.30 | 210 | – | 9.30A | 5.0 | 59 | | + | N |
| 31 | 11.15/11/45 | 30 | 75 | 8A | 7 | 80 | | – | N |
| 32 | 12/12 | 0 | 5 | 7.45A | 7.75 | 99 | | – | N |
| 33 | —/12.15 | – | 5 | 7.20A | 7.25 | 99 | | | N |
| 34 | 12.15/2.45 | 165 | – | 7.45A | 5 | 65 | | | N |
| 35 | 1.15/1.45 | 30 | – | 10A | 8.25 | 94 | | – | N |
| 36 | ANASTASI | | | | | | | | N |
| 37 | | | | | 6.5 | | | | N |
| 38 | —/12.30 | 0 | 60 | 7.30A | 6.5 | 87 | | | N |
| 39 | | 120 | 0 | 7.30A | 5.0 | 71 | | | poor |
| 41 jet lag | 1.15/1.30 | 15 | 30 | 8.30 | 7.0 | 90 | | | N |
| 42 | 1/1.30 | 30 | 30 | 10 | 8.0 | 89 | | | N |
| 43 | 12/12.15 | 15 | 120 | 7.45A | 5.5 | 71 | | | N |
| 44 | 12/12.15 | 15 | 60 | 8.30 | 7.50 | 86 | | – | N |
| 45 | 12.30/12.30 | 0 | 60 | 8.30 | 7.50 | 88 | | | N |
| 46 flying | | | | | | | | | |
| 47 | 412.30 | – | 90 | 8.30 | 6.50 | 81 | | | N |
| 49 | —/1.30 | – | 60? | 9 | 6.50? | 87? | | | N |
| 50 | —/12 | – | 120 | 9 | 7.0 | 77 | | | N |
| 51 | —/11.45 | – | 90 | 8.30 | 7.0 | 85 | | | So so |
| 52 | 11.45/12 | 15 | 90 | 8.45 | 7.0 | 82 | | | N |
| 53 | —/1 | 150 | 0 | 8.0 | 4.50 | 64 | | | constip +/-N |
| 54 | | | | | 6.0 | | | | |
| 55 | | | | | 7.50 | | | | N |
| 56 | /11.45 | | 60 | 7.75 | 7.0 | 87 | | | N |
| 59 | /12 | | 90 | 7.0 | 5.50 | 78 | | | small |
| 60 | 12/12.15 | 15 | 60 | 8.50 | 7.25 | 87 | | | N |
| 67 | 1/1.15 | 15 | 45 | 9.50 | 7.50 | 90 | | | N |
| 69 | | | | | 5.50 | | | | none |
| 70 | 12.30 | 0 | 60 | 9.50 | 8.0 | 88 | | | N |
| 71 | 12.30 | 300 | – | 8.0 | 3.5 | 41 | | | N |
| 72 | 12.45 | | 60 | 9.45 | 8.0 | 89 | | | N |
| 73 | 2 | | 60 | 10.0 | 7.0 | 87 | | | N |
| 74 | 12.45 | | 90 | 8.45 | 6.5 | 81 | | | N |
| Korea | | | | | | | | | |
| 82 | 12.45 | 45 | | 9.30 | 8.0 | 91 | | | poor |
| 83 | 1 | | | 9.30 | 7.0 | | | | N |
| 92 | 1 | | 90 | 8.30 | 6.0 | | | | So so |
| 93 | 1.45 | | 60 | 9.30 | 6.75 | | | | N |
| 94 | 1 | | 60 | 8 | 6 | | | | N |
| 95 | 1 | | 60 | 8.45 | 6.75 | | | | So so |
| 96 | 12.15 | 0 | 0 | 9.30 | 8.0 | | | | none |
| 97 | 12.15 | | 45 | 7.15 | 6.5 | | | | N |
| 100 | 1.30 | | 45 | 9.45 | 7.5 | | | | N |
| 101 | 1.30 | | 60 | 10.30 | 8.0 | | | Still 150 mg In Greece | N |
| 104 | | | | | 5.5 | | | | So so |
| 105 | | | | | 6.0 | | | | So so |
| 106 | | | | | 6.5 | | | | none |
| 107 | | | | | 7.5 | | | | N |
| 111 | | | | | 5.5 | | | | none |
| 112 | | | | | 6.5 | | | | none |
| 113 | 12.15 | | | 9 | 8.0 | | | | N |
| 114 | 1.15 | | | 9.30 | 7.5 | | | 125 mg switch | So so |
| 115 | 1.30 | | | 8.30 | 6.5 | | | | So so |
| 116 | | | | | 8.0 | | | | N |

TABLE 4-continued

| Day # | Time to bed/to sleep | Delay (min) | Fragments awake (min) | Wake up time/Alarm (A) | Total hrs sleep | SE (%) | Sleep age (yrs) | Leg thrashing | Notes |
|---|---|---|---|---|---|---|---|---|---|
| 117 | 12.45 | 45 | | 9.30 | 8.0 | | | | So so |
| 118 | 12.30 | | 60 | 9.30 | 8.0 | | | | Very so so |
| 129 | Switched back up to 150 mg, BM normalized! | | | | | | | | N |
| 130 | | | | | | | | | N |
| 133 | | | | | | | | | N |
| Mean | | 60 | 56 | | 6.7 | 82 | 48 | | N |

The total data from Table 4 above is summarized in Table 5 below.

TABLE 5

| | Delay in falling asleep (min) | Fragments awake during night (min) | Total hrs of sleep (hrs)*** | Sleep efficiency (%) | Leg thrashing |
|---|---|---|---|---|---|
| Pre-treatment | 146 | 90 | 6.2 ± 0.8 | 74 | + |
| On treatment | 60 | 56 | 6 7 ± 1.0 | 82 | − |

The disappearance of leg and arm thrashing (RBD) occurred almost immediately once an appropriate squalamine dosing regimen was reached. Movements of arms and legs occurs because commands from the Suprachiasmatic nucleus in the hypothalamus do not reach the brain stem and muscles do not become atonic or "limp" during dreaming. The patient stopped thrashing on squalamine medication, which implies that the patient's Circadian rhythm was restored.

The patient's skin temperature was also monitored for fluctuations at the wrist using a temperature sensor (I-button) mounted on a wrist-band. Skin temperature at the wrist increases from about 30° C. during the day to 36° C. at night in normal individuals. This diurnal variation of skin temperature correlates well with sleep-wake cycles. When it reaches 34° C., subjects fall asleep; during the night, if it falls below 34° C., subjects awaken. During the day, skin temperature is below 30° C. and subjects remain awake.

Once the patient's Circadian rhythm was restored, the patient started sleeping better at night and stopped falling asleep during the day. An I-button was used to determine changes in skin temperature on different doses of medication, and the results are shown in FIG. 8 (recordings are shown for 100 mg, pm dosing; 150 mg, am dosing; 150 mg, pm dosing, 150 mg, pm dosing, and 150 mg, am dosing. At 100 mg at night, there was a significant delay in sleep onset (red dots) and this delay progressively diminished as the squalamine dose was increased. Total time asleep also increased progressively with increasing squalamine doses.

Figures 8A, 8B, 8C, 8D, 8E:
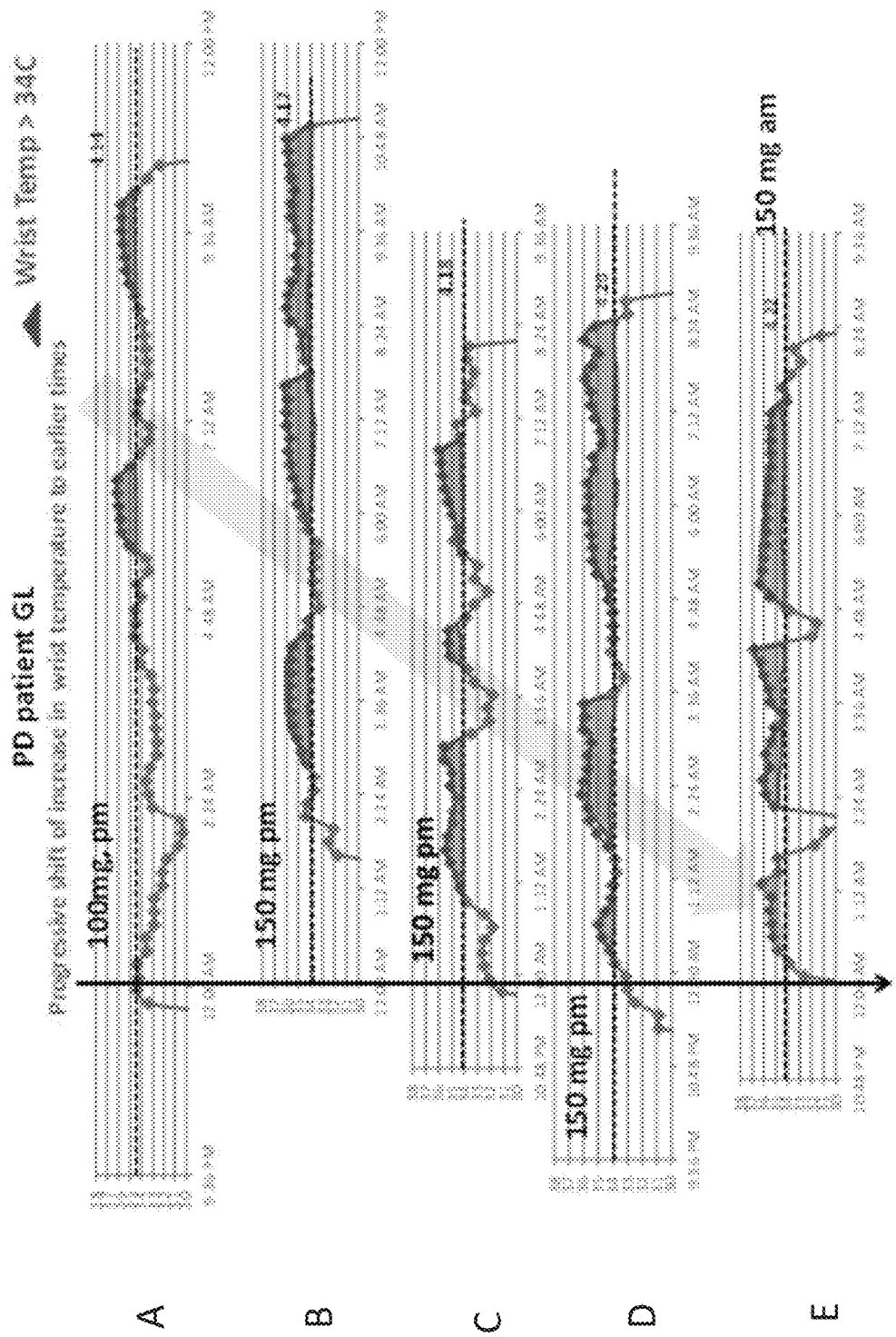
FIGS. 8A, B, C, D and E show I-button recordings tracking the wrist temperature of individuals with sleep disturbances receiving various doses of squalamine (100 mg, pm; 150 mg pm; 150 mg pm; 150 mg pm; 150 mg am) at different times during the day.

The recordings in FIG. 8 show that the patient still takes 2.5 hours to fall asleep at 100 mg given at night (FIG. 8A), and the patient obtained a total of 3 hours of sleep per night (shaded regions). At 150 mg, the delay in sleep onset was reduced (shifted to the left) to1.5 hours immediately (FIG. 8B), then 1 hour (FIG. 8C), and then 30 minutes (FIG. 8D), and the total hours of sleep increased to about 4-5 hours. Some degree of sleep fragmentation was still present, as can be seen on the bottom tracing where temperature falls below 34° C. twice during the night.

Figures 9A, 9B, 9C, 9D:
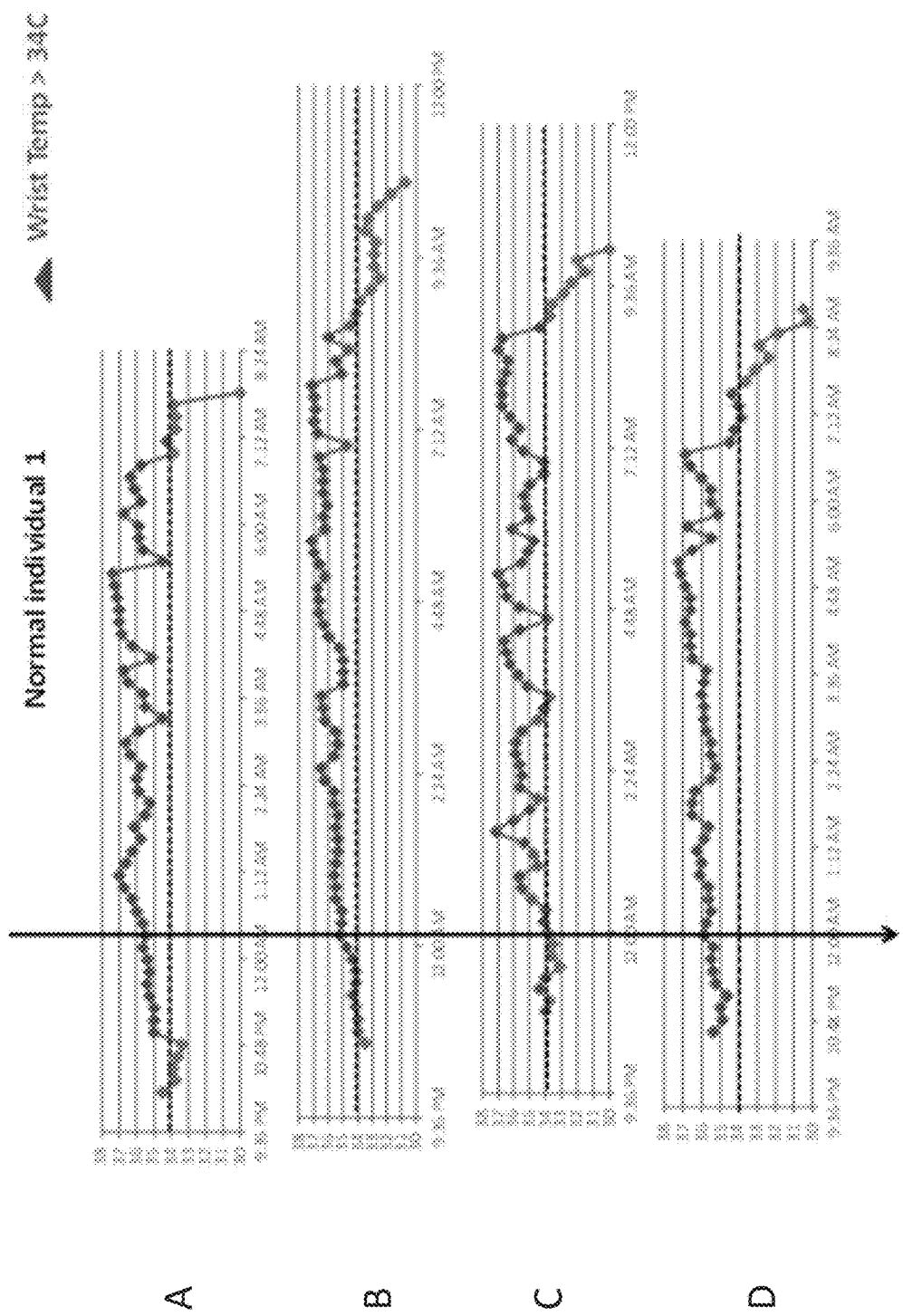
FIGS. 9A, B, C, and D show I-button recordings tracking the wrist temperature of a normal individual (#1).
Figures 10A, 10B, 10C, 10D:
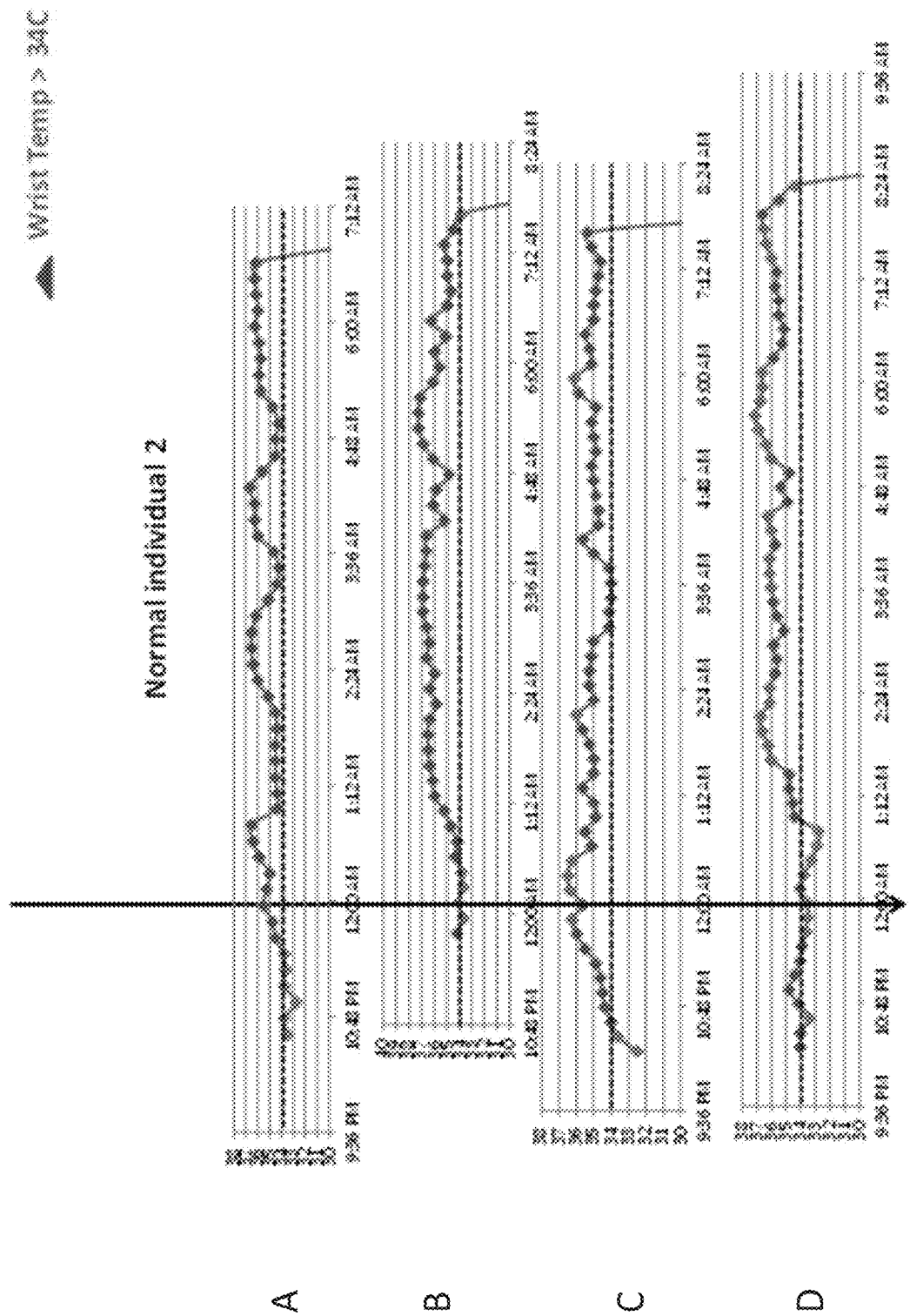
FIGS. 10A, B, C, and D show I-button recordings tracking the wrist temperature of a normal individual (#2). This is an example of a normal circadian rhythm as determined by measuring skin temperature. The tracing from a normal individual shows that skin temperature rises above 34° C. around 1 am and remains above that level continuously until 8.30 am.

In contrast, FIGS. 9 and 10 show recordings from normal individuals over four different days. FIGS. 9A-9D demonstrates that a person falling asleep around 11:00 PM sleeps continuously until 7:00 AM, or about 8 hours. The normal individual's skin temperature never falls below 34° C. FIG. 10 similarly shows a normal individual that falls asleep around 1:00 AM and sleeps continuously until 8:30 AM over 4 separate days (FIGS. 10A-10D). This individual's skin temperature also never falls below 34° C.

FIG. 11A shows the diurnal variation in skin temperature in a normal individual over a 2 week period. The periodogram shown in FIG. 11B shows a clear "peak" above the significance line; in other words, a clear cut diurnal rhythm is present.

FIG. 12 belongs to the patient, and was recorded several months into treatment. The diurnal rhythm has clearly been restored, and the tracing (FIG. 12A) is identical to that of the normal individual shown in FIG. 11A. The periodogram shown in FIG. 12B is also normal, with the single sharp peak of a diurnal rhythm above the significance line.

Example 3

Introduction

Squalamine has been administered orally to individuals with various medical conditions, including Parkinson's disease. A striking prokinetic effect on gastrointestinal (GI) motility as evidenced by relief of constipation, softening of stool consistency, and relief of GI pain and cramping (when present) has been observed in every treated individual. To better understand the mechanisms underlying the effect of squalamine a series of studies have been performed on both young and aged wild type mice and strains engineered as models of Parkinson's disease.

Results

Squalamine Normalizes Colonic Dysmotility Seen with Aging, Opiate Administration, and Parkinson's Disease Isolated colons were mounted in an apparatus that permits continuous perfusion through the lumen, and the monitoring of the velocity, frequency and pressure of migrating muscular contractions (MMCs). Similar to the experience in humans, aging in mice is associated with diminished colonic peristaltic activity. Introducing squalamine into the colonic lumen of the aged mouse leads to a dramatic stimulation of peristalsis restoring motility to that normally observed in a young animal.

Squalamine Overrides the Colonic Dysmotility Caused by an Opiate

In humans, opiates markedly diminish GI motility and suppress fluid secretion causing constipation. These pharmacological effects can be demonstrated by direct administration of loperamide to the colonic lumen. When loperamide is introduced into the lumen of a young mouse colonic peristalsis is inhibited. When squalamine is added in presence of continued loperamide perfusion, the dysmotility is overridden.

Squalamine Excites Enteric Neuronal Activity Directly

Intrinsic primary afferent neurons (IPANs) are believed to be normally stimulated indirectly, through release of neurotransmitters from the epithelium. Since squalamine can be readily transported across an intact intestinal epithelial layer, and can enter a neuron, altering the surface potential of its plasma membrane, an experiment was designed to determine whether the effects of squalamine on the IPAN required the presence of the luminal epithelium.

Figure 13A:
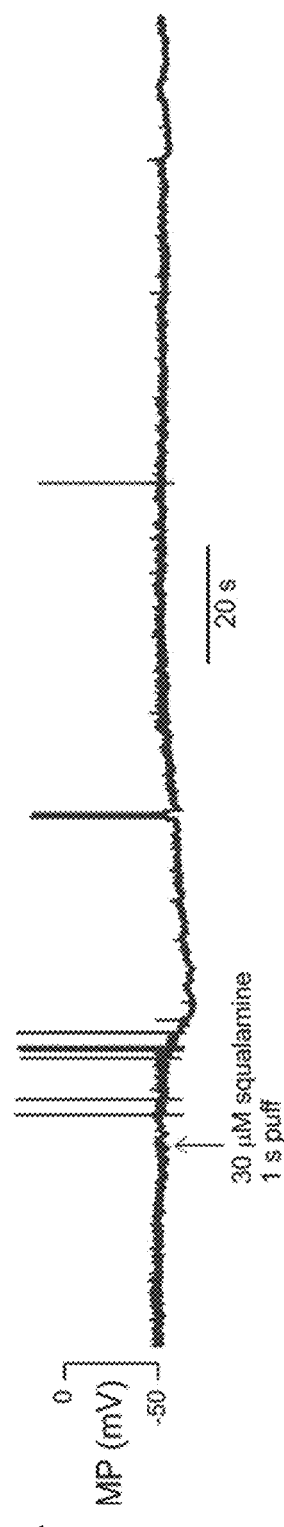
FIGS. 13A, B, and C show that intraluminal squalamine increases mesenteric nerve firing frequency.
Figure 13B:
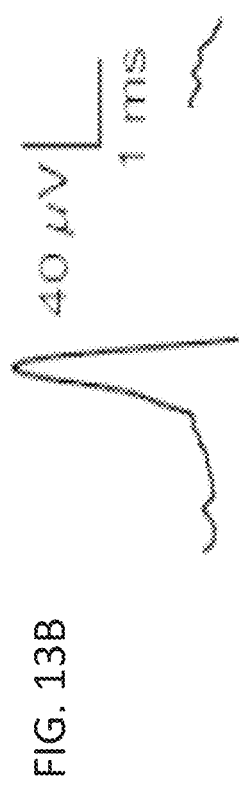
FIG. 13B shows a histogram of multiunit firing frequency averaged over 1 min bins. Squalamine was applied into the lumen by gravity feed 11 min after beginning the recording.

Jejunum was prepared as described in the previous experiment, except the luminal epithelium was manually stripped off the organ using forceps. Squalamine was applied directly onto the myenteric plexus from the luminal surface. Electrophysiological studies were repeated to monitor the activity of a single IPAN within the area of the release of compound. Within 5 seconds the IPAN began a series of spontaneous discharges (FIG. 13A). These data demonstrate that squalamine can stimulate enteric neurons directly. Squalamine appears to be capable of communicating directly with the ENS, in contrast to most substances that communicate with the ENS only indirectly, via their effects on the epithelium.

Squalamine Stimulates Afferent Vagal Signals

Figure 13C:
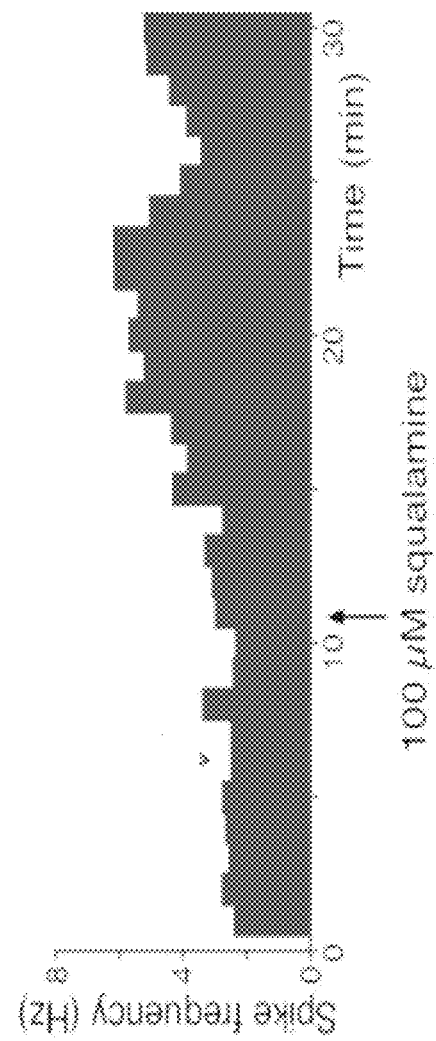
FIG. 13C shows the before and after data of spike frequencies averaged over 3 min for 5 separate experiments. The Control represents background discharge before applying squalamine, and the Peak gives the average firing frequency during a 3 min period at the peak of the response.

To determine whether the electrical activity stimulated by the luminal application of squalamine was principally contained within the ENS of the intestine, or whether it communicated information rostrally to the CNS, a further experiment was designed in which multiunit fiber firing rates were measured from a single jejunal branch of the vagus. Squalamine was introduced 11 minutes after recordings were begun. Vagal afferent firing frequency increased almost immediately thereafter to 3 fold the initial rate within a few minutes. The increased firing rate persisted for at least 20 minutes, as shown in FIG. 13C. These data demonstrate that squalamine stimulates neuronal electrical signaling that is directed to the brainstem and its massive rostral connections.

Squalamine Corrects Colonic Dysmotility in the Murine Model of Parkinson's

Parkinson's disease is associated with varying degrees of constipation, typically beginning decades before diagnosis, and all too often has a profound negative impact on quality of life. It is believed that the ENS in PD is damaged earlier but by the same processes that damage the neurons of the CNS. In our clinical experience oral administration to several individuals with advanced Parkinson's disease corrected long standing constipation within days of initiation of treatment. We explored whether the human experience could be reproduced in the mouse. In the experiments illustrated below studies of colonic motility were conducted using organs from WT (1 yr old FVB/NJ) or PD mice, in which the murine αSynuclein gene has been excised and replaced by several copies of the human αSynuclein gene driven by the normal murine promoter. As shown in FIG. 14A, peristaltic force generated by the peristaltic contractions in both WT and PD colons is similar in magnitude (black columns). Addition of Squalamine to the colon lumen increases the force of contractions in both strains of mice to about the same extent (grey columns).

The PD mouse exhibits a mild constipation phenotype relative to age matched WT individual, as shown in FIG. 14B. The isolated colon from the PD strain presents a more sluggish peristaltic wave than that from the WT animal (black columns). Addition of squalamine to the colonic lumen stimulates the speed of the colonic peristaltic wave from both WT and PD animals, normalizing the PD colon to that of the unstimulated WT mouse (grey columns). These data demonstrate that Squalamine applied locally to the colon can act on the myenteric plexus of both normal and PD animals and functionally restore peristalsis. αSynuclein, despite accumulating in the enteric nervous system of the PD mouse, does not overcome the stimulatory effect of Squalamine introduced into the colonic lumen.

Squalamine Excites Enteric Neuronal Activity

To determine the mechanism by which squalamine stimulated intestinal motility, electrophysiological studies were conducted on single neurons within the colon or jejunum of WT mice, using published methods. Intrinsic primary afferent neurons (IPAN) of the jejunum were patch clamped from the adventitial surface, while the lumen of the jejunum was perfused with either Krebs's buffer or buffer containing 30 µM squalamine. The IPANs are multipolar neurons that receive sensory information from the lumen and then communicate with other divisions within the ENS to influence peristalsis as well as direct information rostrally.

Figure 15:
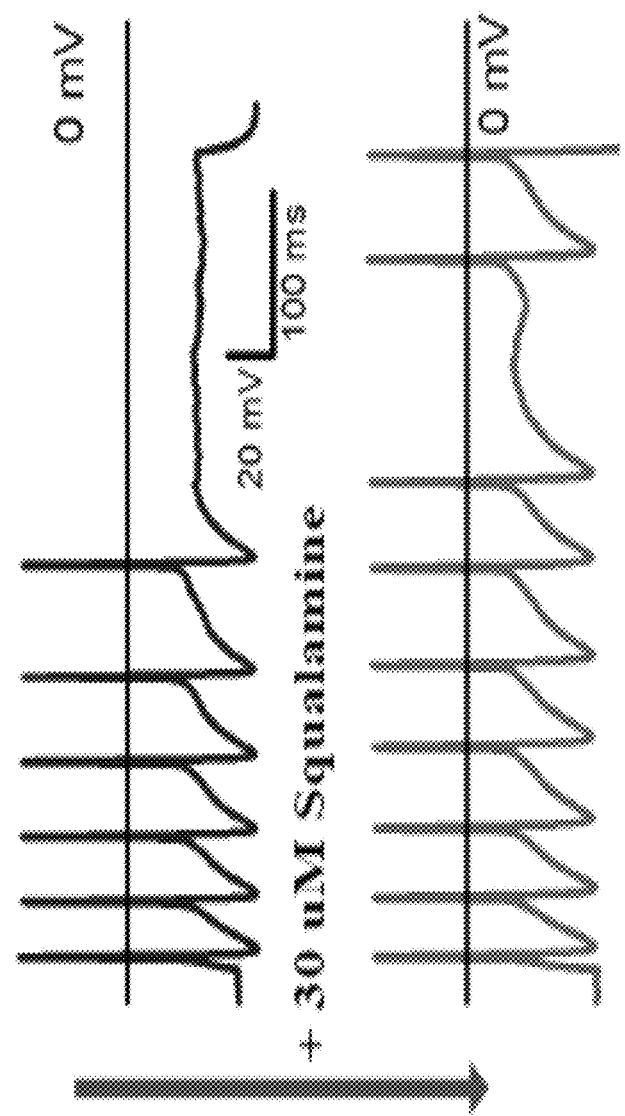
FIG. 15 shows a representative recording of Intrinsic primary afferent neuron (IPAN) member potential. Squalamine evoked bursts of action potential lasting for 10 to 30 min after application of a brief (20 ms) 50 µL puff of squalamine onto the epithelium.

In this experiment IPAN excitability was measured by stimulating the neuron with a single standard pulse, and counting the number of subsequent spontaneous discharges. Within several minutes of application of squalamine the excitability of the IPAN increases such that the number of discharges stimulated by a single electrical impulse increased from 5.5 to 8.8, as shown in FIG. 15, demonstrating that squalamine applied to the intact luminal epithelium can influence the electrical properties of deeply positioned IPANs.

Discussion

The studies described here, conducted in mice, demonstrated that squalamine can directly stimulate the intestinal IPAN, the primary sensory neuron of the intestine. This property, of direct stimulation of the main sensory neuron of the intestine could represent the defining pharmacological characteristic of squalamine. The IPAN is believed to be normally stimulated by endogenous substances released from the epithelium, such as the neurotransmitters released by the enteroendocrine cells. The receptors on the epithelium determine the substances within the lumen that will be recognized by the intestine, and in turn these epithelial cells release substances that stimulate the ENS. Squalamine has the capacity to speak directly with the ENS, and as a consequence could induce stimuli that are highly specific and quite unlike those normally induced by the enteroendocrine cells. Squalamine clearly increases the firing rate of afferent vagal fibers, which communicates information directly to the brain stem and hence to all rostral circuits connected to it. From preliminary analyses of these vagal signals it is believed that the squalamine induced vagal afferent signal has a unique pattern of frequency and amplitude that is reminiscent of a "message" or "code" that might communicate highly specific information rostrally from the ENS. The physiological significance of this generation of a squalamine induced vagal afferent signal is not as yet understood.

The mechanism by which squalamine excites the enteric neuron can be deduced from studies on neurons from the CNS. Application of squalamine directly onto a slice of mouse cortex leads to the neutralization of the negative surface potential of the cytoplasmic face of the plasma membranes of neurons in the treated field. Positively charged squalamine, upon entering a cell, is attracted to the anionic phospholipid head groups that are present on the membrane surface. In turn, squalamine displaces proteins that are bound to the membrane electrostatically, which includes transporters, channels, and proteins involved in actin dynamics. μ-opioid receptor pharmacology could be overridden within target neurons by intracellular changes caused by squalamine. Remarkably, the binding of squalamine to the neuronal membrane does not physically damage the membrane, as measured by its electrical properties. The molecule eventually is transported from the cell and presumably the prior cyto-architecture is restored.

Accordingly, it appears that the progressive loss of function of certain divisions of the human nervous system could be reversed by administration of squalamine.

For instance, αSynuclein accumulates within the ENS and then the brain stem of the individual with Parkinson's disease before it appears in the rest of the brain, and before the onset of the characteristic motor symptoms such as rigidity, akinesia and tremor. αSynuclein, via its positively charged N-terminus, binds electrostatically to the inner cytoplasmic face of the neuronal membrane. As its intracellular concentration increases, membrane bound αSynuclein tends to form neurotoxic aggregates. When Squalamine enters a neuron of the ENS, it displaces many proteins from the inner face of the plasma membrane, including αSynuclein. It is believed that by this mechanism, oral administration of Squalamine prevents the destructive accumulation of toxic αSynuclein aggregates within the ENS of the GI tract of the individual with PD. If the aggregates which form within the ENS, as has been suggested, migrate rostrally and cause neuronal damage to centers within the CNS, then inhibition of the formation of these aggregates within the ENS could have significant disease modifying benefits in PD. The dose of squalamine that restores normal GI motility in PD, in a sense, represents an indirect measure of the reduction in the negative surface potential of ENS neurons, and equates to the dose of compound required to inhibit αS ynuclein aggregation.

Example 4

This example describes an exemplary method of treating and/or preventing symptoms of Parkinson's disease (PD) in a clinical trial setting, including sleep-related symptoms and disorders.

Overview: The subjects of the trial all had PD and experienced constipation, which is a characteristic of PD. The primary objectives of the trial involving patients with PD and constipation were to evaluate the safety and pharmacokinetics of oral squalamine (ENT-01) and to identify the dose required to improve bowel function, which was used as a clinical endpoint.

Several non-constipation PD symptoms were also assessed as endpoints, including, for example, (1) sleep problems, including daytime sleepiness; (2) non-motor symptoms, such as (i) depression (including apathy, anxious mood, as well as depression), (ii) cognitive impairment (e.g., using trail making test and the UPDRS), (iii) hallucinations (e.g., using The University of Miami Parkinson's Disease Hallucinations Questionnaire (UM-PDHQ) and the UPDRS, (iv) dopamine dysregulation syndrome (UPDRS), (v) pain and other sensations, (vi) urinary problems, (vii) light headedness on standing, and (viii) fatigue (e.g., using Parkinson's Disease Fatigue Scale 9PFS-1t and the UPDRS); (3) motor aspects of experiences of daily living, such as (i) speech, (ii) saliva and drooling, (iii) chewing and swallowing, (iv) eating tasks, (v) dressing, (vi) hygiene, (vii) handwriting; (viii) doing hobbies and other activities, (ix) turning in bed, (x) tremor, (xi) getting out of bed, a car, or a deep chair, (xii) walking and balance, (xiii) freezing; (4) motor examination, such as (i) speech, (ii) facial expression, (iii) rigidity, (ix) finger tapping, (v) hand movements, (vi) pronation-supination movements of hands, (vii) toe tapping, (viii) leg agility, arising from chair, (ix) gait, (x) freezing of gait, (xi) postural stability, (xii) posture, (xiii) global spontaneity of movement (body bradykinesia), (xiv) postural tremor of the hands, (xv) kinetic tremor of the hands, (xvi) rest tremor amplitude, (xvii) constancy of rest tremor; (5) motor complications, such as (i) time spent with dyskinesias, (ii) functional impact of dyskinesias, (iii) time spent in the off state, (iv) functional impact of fluctuations, (v) complexity of motor fluctuations, and (vi) painful off-state dystonia.

Active Agent & Dosing: Squalamine (ENT-01; Enterin, Inc.) was formulated for oral administration in the trial. The active ion of ENT-01, squalamine, an aminosterol originally isolated from the dogfish shark, has been shown to reverse gastrointestinal dysmotility in several mouse models of PD. In addition, ENT-01 has been shown to inhibit the formation of aggregates of αS both in vitro, and in a *C. elegans* model of PD in vivo (Perni et al. 2017). In the *C. elegans* model, squalamine produced a complete reversal of muscle paralysis.

ENT-01 is the phosphate salt of squalamine. For this study it has been formulated as a small 25 mg coated tablet. Dosing ranged from 25 mg to 250 mg, with dosages greater than 25 mg requiring multiple pills (e.g., 50 mg=two 25 mg pills). Dosing instructions=take 60 mins before breakfast with 8 oz water. The dose was taken by each patient upon awakening on an empty stomach along with 8 oz. of water simultaneously to dopamine. The subject was not allowed to ingest any food for at least 60 minutes after study medication. The compound is highly charged and will adsorb to foodstuffs, so it was administered prior to feeding.

The phosphate salt of squalamine (ENT-01) is weakly soluble in water at neutral pH but readily dissolves at pH<3.5 (the pH of gastric fluid). Squalamine, as the highly water soluble dilactate salt has been extensively studied in over three Phase 1 and eight Phase 2 human clinical trials as an intravenous agent for the treatment of cancer and diabetic retinopathy. The compound is well tolerated in single and repeat intravenous administration, alone or in combination with other agents, to doses of at least 300 mg/m$^2$).

In the current clinical trial, squalamine (ENT-01) was administered orally to subjects with PD who have long standing constipation. Although this trial was the first in man oral dosing study of ENT-01, humans have long been exposed to low doses of squalamine (milligram to microgram) in the various commercial dogfish shark liver extracts available as nutraceuticals (e.g., Squalamax). In addition, following systemic administration squalamine is cleared by the liver and excreted as the intact molecule (in mice) into the duodenum through the biliary tract. Drug related GI toxicology has not been reported in published clinical trials involving systemic administration of squalamine.

Squalamine (ENT-01) has limited bioavailability in rats and dogs. Based on measurement of portal blood concentrations following oral dosing of radioactive ENT-01 to rat's absorption of ENT-01 from the intestine is low. As a consequence, the principal focus of safety is on local effects on the gastrointestinal tract. However, squalamine (ENT-01) appears to be well tolerated in both rats and dogs.

The starting dose in the Stage 1 segment of the trial was 25 mg (0.33 mg/kg for a 75 kg subject). The maximum single dose in Stage 1 was 200 mg (2.7 mg/kg for a 75 kg subject). The maximum dose evaluated in Stage 2 of the trial was 250 mg/day (3.3 mg/kg/day for a 75 kg subject), and the total daily dosing exposure lasted no longer than 25 days.

The daily dosing range in the clinical trial was from 25 mg (14.7 mg/m$^2$) to 250 mg (147 mg/m$^2$). Oral dosing of squalamine (ENT-01), because of its low oral bioavailability, is not anticipated to reach significant plasma concentrations in human subjects. In preclinical studies, squalamine (ENT-01) exhibited an oral bioavailability of about 0.1% in both rats and dogs. In Stage 1 of this phase 2 study, oral dosing up to 200 mg (114 mg/m$^2$) yielded an approximate oral bioavailability of about 0.1%, based on a comparison of a pharmacokinetic data of the oral dosing and the pharmacokinetic data measured during prior phase 1 studies of IV administration of squalamine.

Study Protocol: The multicenter Phase 2 trial was conducted in two Stages: a dose-escalation toxicity study in Stage 1 and a dose range-seeking and proof of efficacy study in Stage 2.

PD symptoms were assessed using a number of different tools:

(1) Numeric Rating Scales for Pain and Swelling (scale of 0-10, with 0=no pain and 10=worst pain ever experienced);

(2) Rome-IV Criteria for Constipation (7 criteria, with constipation diagnosis requiring two or more of the following: (i) straining during at least 25% of defecations, (ii) lumpy or hard stools in at least 25% of defecations, (iii) sensation of incomplete evacuation for at least 25% of defecations, (iv) sensation of anorectal obstruction/blockage for at least 25% of defecations; (v) manual maneuvers to facilitate at least 25% of defecations; (vi) fewer than 3 defecations per week; and (vii) loose stools are rarely present without the use of laxatives;

(3) Constipation—Ease of Evacuation Scale (from 1-7, with 7=incontinent, 4=normal, and 1=manual disimpaction);

(4) Bristol Stool Chart, which is a patient-friendly means of categorizing stool characteristics (assessment of stool consistency is a validated surrogate of intestinal motility) and Stool Diary;

(5) Sleep Diary (participants completed a sleep diary on a daily basis throughout the study. The diaries included time into bed and estimated time to sleep as well as wake time and duration during the night.);

(6) I-Button Temperature Assessment. The I-Button is a small, rugged self-sufficient system that measures temperature and records the results in a protected memory section. The Thermochron I-Button DS1921H (Maxim Integrated, Dallas, Tex.) was used for skin temperature measurement. I-Buttons were programmed to sample every 10 mins., and attached to a double-sided cotton sport wrist band using Velcro, with the sensor face of the I-Button placed over the inside of the wrist, on the radial artery of the dominant hand. Subjects removed and replaced the data logger when necessary (i.e., to have a bath or shower). The value of skin temperature assessment in sleep research is that the endogenous skin warming resulting from increased skin blood flow is functionally linked to sleep propensity. From the collected data, the mesor, amplitude, acrophase (time of peak temperature), Rayleight test (an index of interdaily stability), mean waveforms are calculated.);

(7) Non-motor Symptoms Questionnaire (NMSQ);

(8) Beck Depression Inventory (BDI-II);

(9) Unified Parkinson's Disease Rating Scale (UPDRS), which consists of 42 items in four subscales (Part I=Non-Motor Aspects of Experiences of Daily Living (nM-EDL) (1.1 cognitive impairment, 1.2 hallucinations and psychosis, 1.3 depressed mood, Part II=Motor Aspects of Experiences of Daily Living (M-EDL), Part III=Motor Examination, and Part IV=Motor Complications;

(10) Mini Mental State Examination (MMSE);

(11) Trail Making Test (TMT) Parts A and B;

(12) The University of Miami Parkinson's Disease Hallucinations Questionnaire (UM-PDHQ);

(13) Parkinson's Disease Fatigue Scale (PFS-16);

(14) Patient Assessment of Constipation Symptoms (PAC-SYM);

(15) Patient Assessment of Constipation Quality of Life (PAC-QOL);

(16) REM Sleep Behavior Disorder Screening Questionnaire; and

(17) Parkinson's Disease Sleep Scale.

Exploratory end-points, in addition to constipation, included for example, (i) depression assessed using the Beck Depression Inventory (BDI-II) (Steer et al. 2000) and Unified Parkinson's Disease Rating Scale (UPDRS); (ii) cognition assessed using the Mini Mental State Examination (MMSE) (Palsteia et al. 2018), Unified Parkinson's Disease Rating Scale (UPDRS), and Trail Making Test (TMT); (iii) sleep and REM-behavior disorder (RBD) using a daily sleep diary, I-Button Temperature Assessment, a REM sleep behavior disorder (RBD) questionnaire (RBDQ) (Stiasny-Kolster et al. 2007), and the UPDRS; (iv) hallucinations assessed using the PD hallucinations questionnaire (PDHQ) (Papapetropoulos et al. 2008), the UPDRS, and direct questioning; (v) fatigue using the Parkinson's Disease Fatigue Scale (PFS-16) and the UPDRS; (vi) motor functions using the UPDRS; and (vii) non-motor functions using the UPDRS.

Assessments were made at baseline and at the end of the fixed dose and washout periods. Circadian system status was evaluated by continuously monitoring wrist skin temperature (Thermochron iButton DS1921H; Maxim, Dallas) following published procedures (Sarabia et al. 2008).

Based on these data, it is believed that administration of squalamine (ENT-01), a compound that can displace αS from membranes in vitro, reduces the formation of neurotoxic αS aggregates in vivo, and stimulates gastrointestinal motility in patients with PD and constipation. The observation that the dose required to achieve a prokinetic response increases with constipation severity supports the hypothesis that the greater the burden of αS impeding neuronal function, the higher the dose of squalamine (ENT-01) required to restore normal bowel function.

Study Design: A multicenter Phase 2 trial was conducted in two Stages: a dose-escalation toxicity study in Stage 1 and a dose range-seeking and proof of efficacy study in Stage 2. The protocol was reviewed and approved by the institutional review board for each participating center and patients provided written informed consent.

Following successful screening, all subjects underwent a 14-day run-in period where the degree of constipation was assessed through a validated daily log (Zinsmeister et al. 2013) establishing baseline CSBMs/week. Subjects with an average of <3 CSBMs/week proceeded to dosing.

In Stage 1, ten (10) PD patients received a single escalating dose of squalamine (ENT-01) every 3-7 days beginning at 25 mg and continuing up to 200 mg or the limit of tolerability, followed by 2-weeks of wash-out. Duration of this part of the trial was 22-57 days. The 10 subjects in the sentinel group were assigned to Cohort 1 and participated in 8 single dosing periods. Tolerability limits included diarrhea or vomiting. A given dose was considered efficacious in stimulating bowel function (prokinetic) if the patient had a complete spontaneous bowel movement (CSBM) within 24 hours of dosing.

Each dose period was staggered, so that subjects 1-2 were administered a single dose of the drug at the lowest dose of 25 mg. Once 24 hours have elapsed, and provided there are no safety concerns, the patient was sent home and brought back on day 4-8 for the next dose. During the days the subjects are home, they completed the daily diaries and e-mailed them to the study coordinators. Subjects 3-10 were dosed after the first 2 subjects have been observed for 72 hours, i.e. on Day 4. Subjects 1-2 were also brought back on Day 4-8 and given a single dose of 50 mg. Once another 24 hours have elapsed and provided there are no safety concerns, the patients were all sent home and instructed to return on Day 7 for the next dosing level. This single dosing regimen was continued until each subject was given a single dose of 200 mg or has reached a dose limiting toxicity (DLT). DLT was the dose which induces repeated vomiting, diarrhea, abdominal pain or symptomatic postural hypotension within 24 hours of dosing.

In Stage 2, 34 patients were evaluated. First, 15 new PD patients were administered squalamine (ENT-01) daily, beginning at 75 mg, escalating every 3 days by 25 mg to a dose that had a clear prokinetic effect (CSBM within 24 hours of dosing on at least 2 of 3 days at a given dose), or the maximum dose of 175 mg or the tolerability limit. This dose was then maintained ("fixed dose") for an additional 3-5 days. After the "fixed dose", these patients were randomly assigned to either continued treatment at that dose or to a matching placebo, for an additional 4-6 days prior to a 2-week wash-out.

A second cohort of 19 patients received squalamine (ENT-01) escalating from 100 mg/day to a maximum of 250 mg/day without subsequent randomization to squalamine (ENT-01) or placebo. Criteria for dose selection and efficacy were identical to those used in the previous cohort.

Patient Population: Patients were between 18 and 86 years of age and diagnosed with PD by a clinician trained in movement disorders following the UK Parkinson's Disease Society Brain Bank criteria (Fahn et al. 1987). Patients were required to have a history of constipation as defined by <3 CSBMs/week and satisfy the Rome IV criteria for functional constipation (Mearin et al. 2016) at screening, which requires 2 or more of the following: Straining during at least 25% of defecations; lumpy or hard stools in at least 25% of defecations; sensation of incomplete evacuation in at least 25% of defecations; sensation of anorectal obstruction/blockage in at least 25% of defecations; and/or manual maneuvers to facilitate at least 25% of defecations.

Baseline characteristics of patients are shown in Table 6. Patients in Stage 2 had somewhat longer duration of Parkinson's disease and higher UPDRS scores than participants in Stage 1.

TABLE 6

Baseline Characteristics of Dosed Patients

| Characteristic | Stage 1** (n = 10) | Stage 2*** (n = 34) | Total (n = 44) |
|---|---|---|---|
| Sex-no. (%) | | | |
| Male | 5 (50) | 25 (73.5) | 30 (68.1) |
| Female | 5 (50) | 9 (26.5) | 14 (31.8) |
| White race-no. (%) | 8 (80) | 34 (100) | 42 (95.54) |

TABLE 6-continued

Baseline Characteristics of Dosed Patients

| Characteristic | Stage 1** (n = 10) | Stage 2*** (n = 34) | Total (n = 44) |
|---|---|---|---|
| Age-yr | | | |
| Mean | 65.0 | 74.5 | 72.5 |
| Range | 58-70.5 | 60.6-84.2 | 58-84.2 |
| Age at PD diagnosis-yr | | | |
| Mean | 61.1 | 67.7 | 66.2 |
| Range | 54.2-69 | 50.6-82.5 | 50.6-82.5 |
| Duration of PD-yr | | | |
| Mean | 4.2 | 6.8 | 6.2 |
| Range | 1-11 | 0.3-17.3 | 0.3-17.3 |
| Duration of constipation-yr | | | |
| Mean | 25.8 | 16.8 | 18.9 |
| Range | 1-65 | 0.5-66.0 | 0.5-66.0 |
| UPDRS score | | | |
| Mean | 53.4 | 63.2 | 61.3 |
| Range | 33-88 | 24-122 | 24.0-122.0 |
| Hoehn and Yahr-Stage | | | |
| Mean | 2.0 | 2.4 | 2.3 |
| Range | 2.0 | 1.0-5.0 | 1.0-5.0 |
| Constipation severity*— CSBM/wk-no. (%) | | | |
| 0-1 | 8 (80) | 14 (41.2) | 22 (50) |
| 1.1-2 | 2 (20) | 17 (50) | 19 (43.2) |
| 2.1-3 | 0 | 3 (8.8) | 3 (6.8) |

*At baseline. Baseline value is the average number of CSBMs per week calculated at the end of the 2-week run-in period.
**In Stage 1, 10 patients received single escalating doses every 3-7 days starting at 25 mg and escalating up to dose limiting toxicity (DLT) or 200 mg, whichever came first, followed by a 2-week wash-out period.
***In Stage 2, 15 patients received daily doses starting at 75 mg and escalating every 3 days up to prokinetic dose (dose producing CSBMs on at least 2 of 3 days) or 175 mg, whichever came first, followed by an additional 2-4 days at that dose ("fixed dose" period) and were then randomized to treatment at the "fixed-dose" or placebo for 4-6 days. Wash-out lasted 2 weeks. The remaining 19 patients were escalated from 100 mg to prokinetic dose or 250 mg, whichever came first, followed by an additional 2-4 days at that dose and then a 2-week wash-out period.

Figure 17:
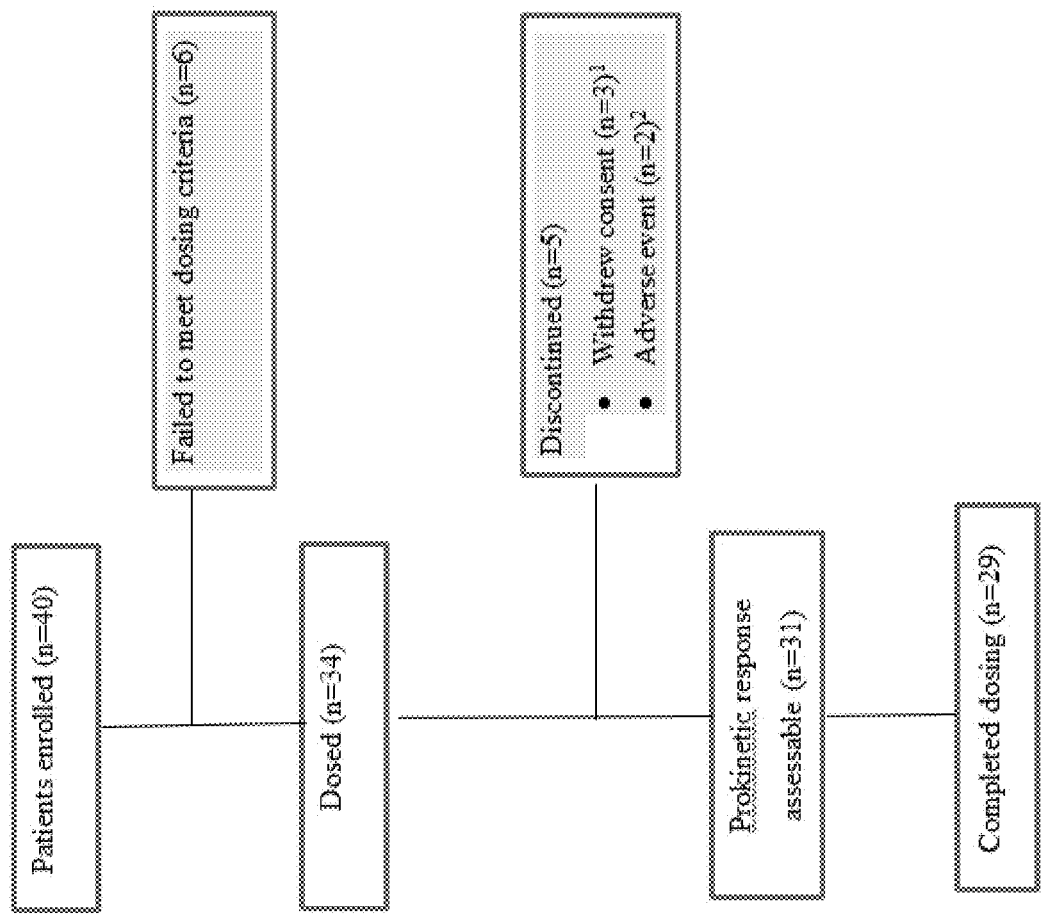
FIG. 17 is a schematic (flowchart) showing patient disposition in Stage 2. (1) Patients first enrolled (n=40); (2) 6 patients failed to meet dosing criteria and were excluded; (3) 34 patients were dosed; (4) 5 patients were discontinued; 3 patients withdrew consent (with 1 patient lost to follow up and 2 patients withdrew because of diarrhea); and 2 patients discontinued because of an adverse event (recurrent dizziness after medication); (5) 31 patients had an assessable prokinetic response; and (6) 29 patients completed dosing.
Figure 18:
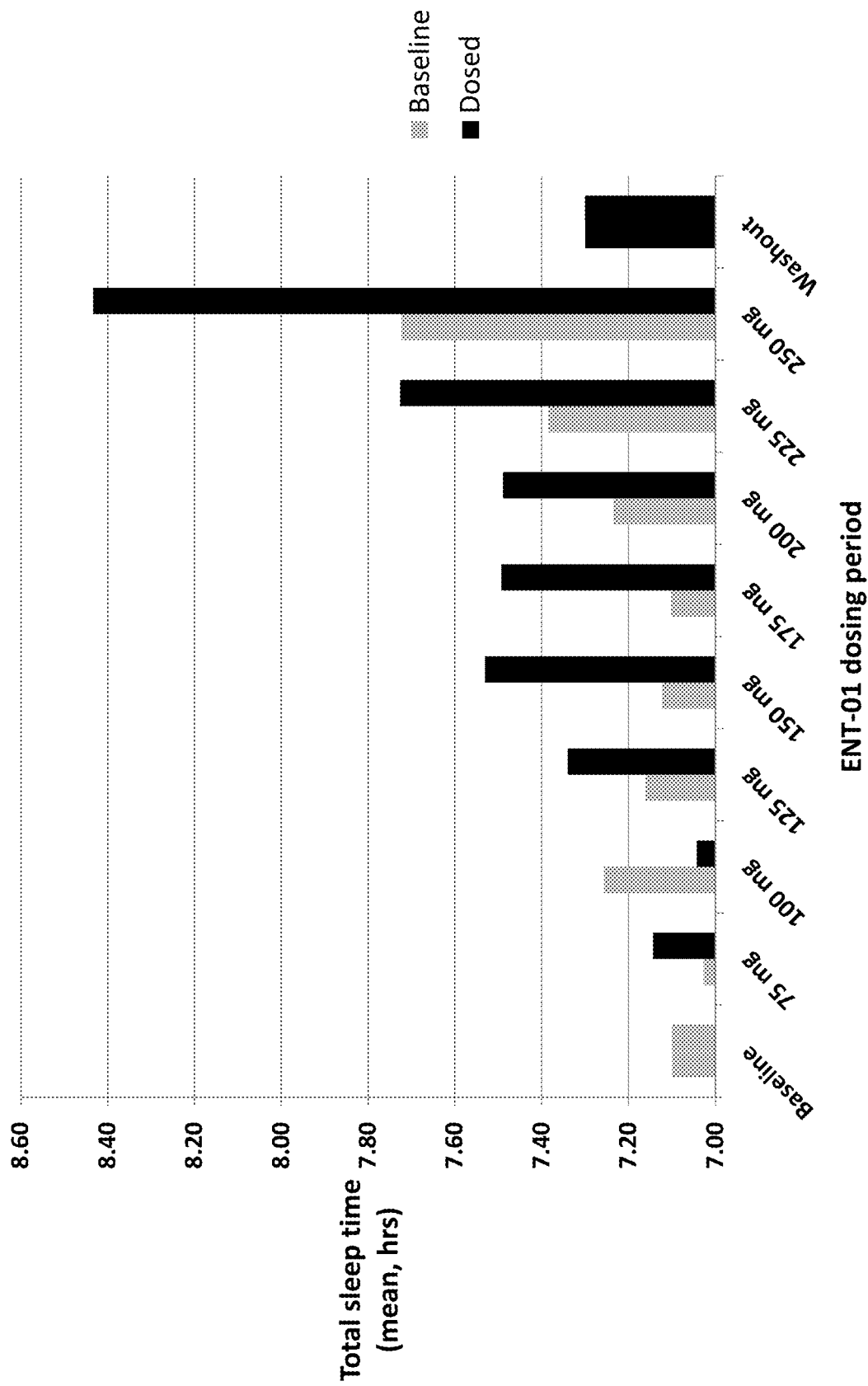
FIG. 18 is a chart of total sleep time in relation to squalamine dose. Total sleep time was obtained from the sleep diary by subtracting awake time during the night from total time spent in bed. Total sleep time per night was logged for each patient at baseline, each dosing period and at washout, and the means were determined. The light grey bar represents the baseline value for each cohort at a given dose level and the dark grey bar represents the value for the same cohort at the stated dose of squalamine (ENT-01; Kenterin™). The number of patients represented at each value are: Baseline, 33; 75 mg, 21; 100 mg, 28; 125 mg, 18; 150 mg, 15; 175 mg, 12; 200 mg, 7; 225 mg, 3; 250 mg, 2; washout, 33. P values were as follows: 75 mg, p=0.4; 100 mg, p=0.1; 125 mg, p=0.3; 150 mg, p=0.07; 175 mg, p=0.03; 200 mg, p=0.3; 225 mg, p=0.5; 250 mg, p=0.3; wash-out, p=0.04 (paired t test).

Safety and Adverse Event (AE) Profile: Fifty patients were enrolled and 44 were dosed. In Stage 1, 10 patients were dosed, 1 (10%) withdrew prior to completion and 9 (90%) completed dosing. In stage 2, 6 (15%) patients had ≥3 CSBM/week at the end of the run-in period and were excluded, 34 patients were dosed and bowel response was assessable in 31 (91%). Two patients (5.8%) were terminated prior to completion because of recurrent dizziness, and 3 others withdrew during dosing (8.8%): 2 because of diarrhea and 1 because of holiday. Fifteen patients were randomized. Study-drug assignments and patient disposition are shown in Table 7 and FIG. 17.

TABLE 7

Study drug assignments and adherence to treatment

| | Stage 1 | Stage 2 |
|---|---|---|
| Enrolled | 10 | 40 |
| Failed prior to dosing | 0 | 6 |
| Dosed | 10 | 34 |
| 25-200 mg | 10 | |
| 75-175 mg | | 19 |
| 100-250 mg | | 15 |
| Terminated (%) | 0 (0) | 2* (5.8) |
| Withdrew (%) | 1 (10) | 3 (8.8) |
| Completed dosing (%) | 9 (90) | 31** (91) |
| Randomized | | 15 |

TABLE 7-continued

Study drug assignments and adherence to treatment

|  | Stage 1 | Stage 2 |
|---|---|---|
| Treatment |  | 6 |
| Placebo |  | 9 |

The 2 patients who were terminated **29 patients completed dosing but an additional 2 who withdrew had an assessable prokinetic end-point.

Most AEs were confined to the GI tract (88% in Stage 1 and 63% in Stage 2). The most common AE was nausea which occurred in 4/10 (40%) patients in Stage 1 and in 18/34 (52.9%) in Stage 2 (Table 6). Diarrhea occurred in 4/10 (40%) patients in Stage 1 and 15/34 (44%) in Stage 2. One patient withdrew because of recurrent diarrhea. Other GI related AEs included abdominal pain 11/44 (32%), flatulence 3/44 (6.8%), vomiting 3/44 (6.8%), worsening of acid reflux 2/44 (4.5%), and worsening of hemorrhoids 1/44 (2.2%). One patient had a lower GI bleed (Serious adverse event, SAE) during the withdrawal period. This patient was receiving aspirin, naproxen and clopidogrel at the time of the bleed, and colonoscopy revealed large areas of diverticulosis and polyps. This SAE was considered unrelated to study medication. The only other noteworthy AE was dizziness 8/44 (18%). Dizziness was graded as moderate in one patient who was receiving an alpha-adrenergic blocking agent (Terazosin). This patient was withdrawn from the study and recovered spontaneously. All other AEs resolved spontaneously without discontinuation of squalamine (ENT-01). The relationship between dose and AEs is shown in Table 8.

TABLE 8

All adverse events (n, %)

| Enrolled | Stage 1 (n = 10) | Stage 2 (n = 40) |
|---|---|---|
| Dosed | 10 | 34 |
| GI: |  |  |
| Nausea |  |  |
| Mild | 4(40) | 18(52) |
| Moderate | 0 | 1(2.9) |
| Diarrhea |  |  |
| Mild | 1(10) | 12(35) |
| Moderate | 3(30) | 2(5.8) |
| Severe | 0 | 1(2.9) |
| Vomiting |  |  |
| Mild | 1(10) | 2(5.8) |
| Moderate | 0 | 0 |
| Abdominal pain |  |  |
| Mild | 2(20) | 4(11.7) |
| Moderate | 3(30) | 2(5.8) |
| Flatulence |  |  |
| Mild | 2(20) | 1(3) |
| Moderate | 0 | 0 |
| Loss of appetite* |  |  |
| Mild | 1(10) | 0 |
| Moderate | 0 | 0 |
| Worsening acid reflux |  |  |
| Mild | 0 | 4(11.7) |
| Moderate | 0 | 0 |
| Worsening hemorrhoid |  |  |
| Mild | 0 | 1(3) |
| Moderate | 0 | 0 |
| Lower GI bleed** |  |  |

TABLE 8-continued

All adverse events (n, %)

| Enrolled | Stage 1 (n = 10) | Stage 2 (n = 40) |
|---|---|---|
| Severe | 0 | 1(2.5) |
| Non-GI: |  |  |
| Dizziness |  |  |
| Mild | 0 | 7(20.5) |
| Moderate | 0 | 1(2.9) |
| Blood in urine* |  |  |
| Mild | 1(10) | 0 |
| Moderate | 0 | 0 |
| Headache |  |  |
| Mild | 1(10) | 3(8.8) |
| Moderate | 0 | 0 |
| Urinary retention |  |  |
| Mild | 0 | 1(3) |
| Moderate | 0 | 0 |
| Urinary tract infection |  |  |
| Mild | 0 | 1(3) |
| Moderate | 0 | 2(5.8) |
| Increased urinary frequency |  |  |
| Mild | 0 | 2(5.8) |
| Moderate | 0 | 0 |
| Skin lesions-rash |  |  |
| Mild | 0 | 3(8.8) |
| Moderate | 0 | 0 |
| Eye infection |  |  |
| Mild | 0 | 1(3) |
| Moderate | 0 | 0 |
| Difficulty falling asleep |  |  |
| Mild | 0 | 1(3) |
| Moderate | 0 | 0 |

*Unrelated to ENT-01
**colonic diverticulosis, polyp, patient on aspirin, Plavix and naproxen. Unrelated to ENT-01

TABLE 9

Common adverse events by dose

| Dose | Stage 1 | | | Stage 2 | | |
|---|---|---|---|---|---|---|
| (mg) | Diarrhea | Nausea | Vomiting | Diarrhea | Nausea | Dizziness* |
| 0 | 0 | 0 | 0 | 1 | 0 | 2 |
| 25 | 1 | 0 | 0 | — | — | — |
| 50 | 1 | 0 | 0 | — | — | — |
| 75 | 1 | 0 | 0 | 7 | 3 | 8 |
| 100 | 0 | 1 | 1 | 10 | 12 | 7 |
| 125 | 1 | 2 | 1 | 3 | 4 | 8 |
| 150 | 1 | 0 | 0 | 2 | 11 | 2 |
| 175 | 1 | 1 | 0 | 1 | 12 | 0 |
| 200 | 0 | 2 | 0 | 2 | 6 | — |
| 225 | — | — | — | 3 | 1 | — |
| 250 | — | — | — | 2 | — | — |

*lightheadedness included

TABLE 10

Dose limiting toxicity criteria

| Diarrhea | Increase 4-6 stools/day over baseline |
|---|---|
| Vomiting | 3-5 episodes in 24 hours |

TABLE 10-continued

Dose limiting toxicity criteria

| Abdominal pain | Moderate pain limiting daily activities |
| Postural hypotension | Moderately symptomatic and limiting daily activities or BP <80/40 |

No formal sample size calculation was performed for Stage 1. The number of subjects (n=10) was based on feasibility and was considered sufficient to meet the objectives of the study; which was to determine the tolerability of the treatment across the range of tested doses. For Stage 2, assuming the highest proportion of spontaneous resolution of constipation with no treatment to be 0.10, 34 evaluable subjects who have measurements at both baseline and at the end of the fixed dose period provided 80% power to detect the difference between 0.10 (proportion expected if patients are not treated) and a squalamine (ENT-01) treated proportion of 0.29.

No randomization was performed for Stage 1. During the randomization period of Stage 2, subjects were randomly allocated in equal proportion (1:1) to 1 of 2 double-blind treatment groups in a block size of 4: (1) squalamine (ENT-01) at the identified fixed dose level, or (2) placebo at the identified fixed dose level.

Adverse events were coded using the current version of MedDRA. Severity of AEs were assessed by investigators according to CTCAE (v4.03): Grade 1 is labeled as Mild, Grade 2 as Moderate, and Grade 3 and above as Severe. AEs that have a possible, probable or definite relationship to study drug were defined to be related to the study drug while others were defined as "not related". The number (percentage) of subjects who experienced an AE during escalation and fixed dosing periods were summarized by dose level and overall for each stage. The denominator for calculating the percentages were based on the number of subjects ever exposed to each dose and overall.

Figures 16A, 16B:
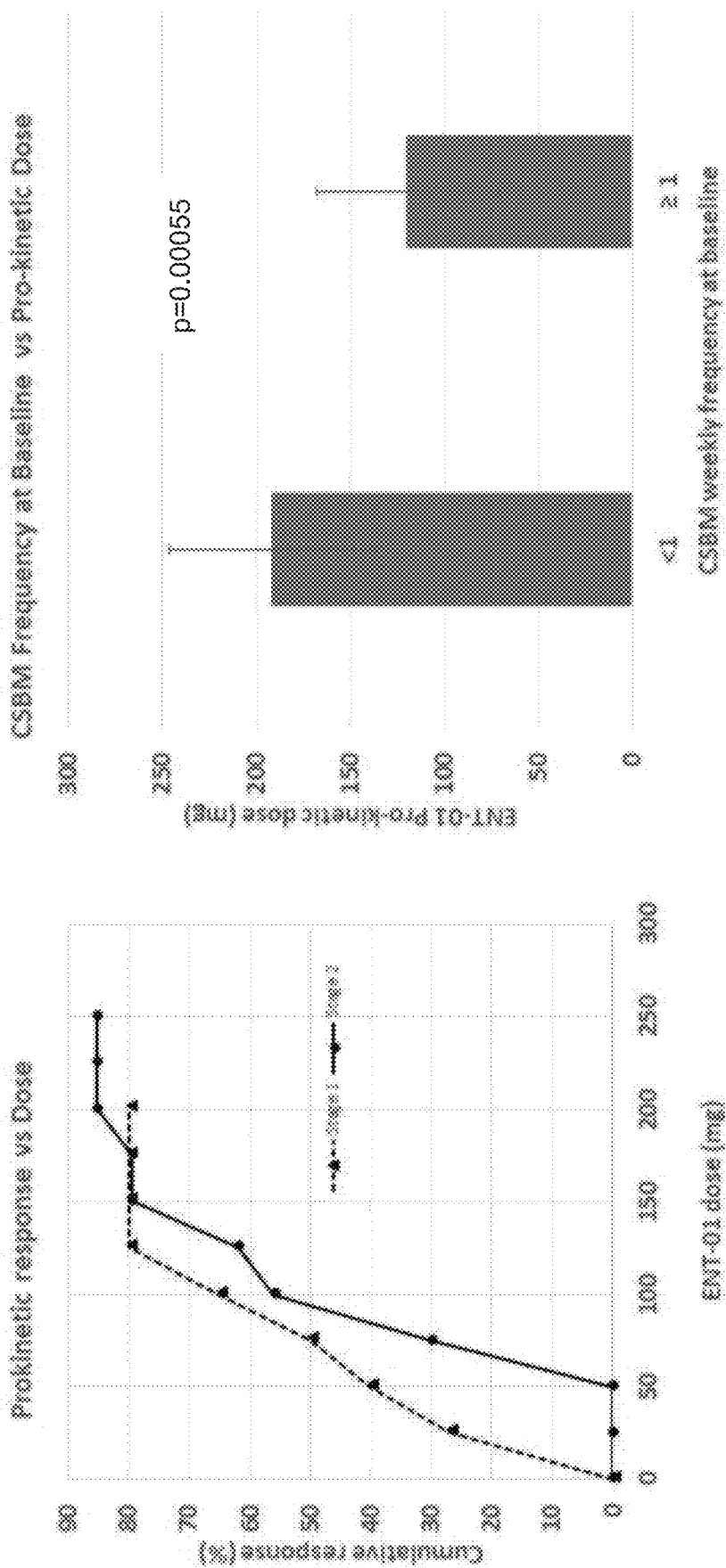
FIGS. 16A-16B show prokinetic activity of squalamine (ENT-01, a synthetic squalamine salt comprising squalamine as the active ion). As shown in panel A, in Stage 1 (single dose), cumulative prokinetic response rate was defined as the proportion of patients who had a complete spontaneous bowel movements (CSBM) within 24 hours of dosing. In Stage 2 (daily dosing), a prokinetic response was defined as the fraction of patients who had a CSBM within 24 hours of dosing on at least 2 out of 3 days at any given dose. As shown in panel B, the prokinetic dose of squalamine was significantly related to baseline constipation severity (p=0.00055). Patients with baseline CSBM<1 required a higher dose (mean, 192 mg) of squalamine than patients with CSBM≥1 (mean, 120 mg).

Effect on Bowel Function: Cumulative responder rates of bowel function are shown in FIG. 16A. In Stage 1 (single dose), cumulative response rate increased in a dose-dependent fashion from 25% at 25 mg to a maximum of 80% at 200 mg.

In Stage 2 (daily dosing), the response rate increased in a dose-dependent fashion from 26% at 75 mg to 85.3% at 250 mg. The dose required for a bowel response was patient-specific and varied from 75 mg to 250 mg. Median efficacious dose was 100 mg. Average CSBM/week increased from 1.2 at baseline to 3.8 at fixed dose ($p=2.3\times10^{-8}$) and SBM increased from 2.6 at baseline to 4.5 at fixed dose ($p=6.4\times10^{-6}$) (Table 11). Use of rescue medication decreased from 1.8/week at baseline to 0.3 at fixed dose ($p=1.33\times10^{-5}$). Consistency based on the Bristol stool scale also improved, increasing from mean 2.7 to 4.1 (p=0.0001) and ease of passage increased from 3.2 to 3.7 (p=0.03). Subjective indices of wellbeing (PAC-QOL) and constipation symptoms (PAC-SYM) also improved during treatment (p=0.009 and p=0.03 respectively).

TABLE 11

Stool related indices Stage 2 (Dosed patients, n = 34)

| | Baseline (mean, SD) | Fixed dose (mean, SD) | P-value |
|---|---|---|---|
| CSBM* | 1.2 (0.90) | 3.8 (2.40) | $2.3 \times 10^{-8}$ |
| SBM* | 2.6 (1.45) | 4.5 (2.21) | $6.4 \times 10^{-6}$ |
| Suppository use* | 1.8 (1.92) | 0.3 (0.67) | $1.33 \times 10^{-5}$ |
| Consistency*** | 2.7 (1.20) | 4.1 (2.13) | 0.0001 |
| Ease of passage** | 3.2 (0.73) | 3.7 (1.19) | 0.03 |
| PAC-QOL total | 1.4 (0.49) | 1.2 (0.59) | 0.009 |
| PAC-SYM | 1.3 (0.45) | 1.1 (0.49) | 0.03 |

*weekly average;
**Ease of evacuation scale, where 1-manual disimpaction and 7 = incontinent;
***Bristol stool scale 1-7, where 1 = separate hard lumps and 7 = liquid consistency The dose that proved efficacious in inducing a bowel response was strongly related to constipation severity at baseline (p=0.00055) (FIG. 16B); patients with baseline constipation of <1 CSBM/week required higher doses for a response (mean 192 mg) than patients with ≥1 CSBM/week (mean 120 mg).

While the improvement in most stool-related indices did not persist beyond the treatment period, CSBM frequency remained significantly above baseline value (Table 12).

TABLE 12

Reversal of stool indices to baseline during the wash-out period (Stage 2)

| | Baseline (Mean, SD) | Fixed dose (Mean, SD) | Wash-out (Mean, SD) | P-value (wash-out vs. baseline) |
|---|---|---|---|---|
| CSBM | 1.2 (0.90) | 3.8 (2.4) | 1.8 (1.19) | 0.01 |
| SBM | 2.6 (1.45) | 4.5 (2.21) | 3.2 (1.80) | 0.16 |
| Ease | 3.2 (0.73) | 3.7 (1.19) | 3.3 (0.81) | 0.78 |
| Consistency | 2.7 (1.20) | 4.1 (2.13) | 2.8 (1.39) | 0.85 |
| Rescue meds | 1.8 (1.92) | 0.3 (0.67) | 1.0 (1.40) | 0.13 |
| PAQ-QOL | 1.4 (0.49) | 1.2 (0.59 | 1.2 (0.63) | 0.04 |
| PAQ-SYM | 1.3 (0.45) | 1.1 (0.49) | 1.1 (0.60) | 0.11 |

The primary efficacy outcome variable was whether or not a subject was a "success" or "failure". This is an endpoint based on subject diary entries for the "fixed dose" period prior to the endpoint assessment defined as average complete stool frequency increase by 1 or more over baseline, or 3 or more complete spontaneous stools/week. The subject was deemed a "success" if s/he met one or more of the criteria listed above, otherwise the subject was deemed a "failure". The primary analysis was based on all subjects with a baseline assessment and an assessment at the end of the "fixed-dose" period and was a comparison of the proportion of successes with 0.10 (the null hypothesis corresponding to no treatment effect).

The proportion of subjects for whom the drug was a success was estimated with a binomial point estimate and corresponding 95% confidence interval. A secondary analysis compared the proportions of subjects who are deemed a success at the end of the randomized fixed-dose period between those randomized to the squalamine (ENT-01) arm and those randomized to the placebo arm. A Fisher's exact test was used to compare the proportions of subjects who were deemed a success at the end of randomization period between the two randomized arms.

Subgroup Analysis: Fifteen patients were randomized to treatment (n=6) or placebo (n=9) after the fixed dose period. During the 4-6 days of randomized treatment, the mean CSBM frequency in the treatment group remained higher than baseline as compared to those receiving placebo who returned to their baseline values (Table 13).

TABLE 13

CSBM frequency in the randomized cohort

| CSBM/week | Baseline | Fixed dose | Randomized | Washout |
|---|---|---|---|---|
| Treatment (n = 6) | 0.8 | 3.2 | 2.4 | 0.9 |
| Placebo (n = 9) | 1.6 | 3.3 | 1.4 | 1.6 |

CSBM increased in both groups during the treatment period and remained high in the treatment group during the randomized period but fell to baseline values in the placebo group.

Pharmakokinetics: PK data were collected on the 10 patients enrolled in Stage 1 and 10 patients enrolled in Stage 2 to determine the extent of systemic absorption. In Stage 1, PK data were obtained at each visit, pre-medication, at 1, 2, 4, 8 and 24 hours (Table 14). In Stage 2, PK was measured on days 1 and 6 of the randomization period pre-medication, at 1, 2, 4 and 8 hours (Table 15). Based on the pharmacokinetic behavior of intravenously administered squalamine determined in prior clinical studies it is estimated that squalamine (ENT-01) exhibited oral bio-availability of less than 0.3% (Bhargava et al. 2001; Hao et al. 2003).

TABLE 14

Pharmacokinetics of orally administered squalamine (ENT-01) in Stage 1.
Stage 1

| Dose (mg) | # of patients | $C_{max}$ (ng/ml) | $T_{max}$ (hour) (Median Value) | $T_{1/2}$ (hours) (n) | $AUC_{0-8\ hr}$ (ng*hour/ml) | $AUC_{0-16\ hr}$ (ng*hour/ml) |
|---|---|---|---|---|---|---|
| 25 | 9 | 2.84 | 1.0 | 2.6 (3) | 10.8 | 19.6 |
| 50 | 10 | 3.73 | 2.0 | 3.4 (3) | 18.5 | 33.1 |
| 75 | 9 | 4.33 | 2.0 | 2.8 (2) | 18.4 | 29.8 |
| 100 | 9 | 6.18 | 2.0 | 3.9 (5) | 29.6 | 51.5 |
| 125 | 9 | 9.63 | 2.0 | 3.9 (4) | 43.1 | 77.7 |
| 150 | 7 | 6.27 | 2.0 | 5.6 (4) | 31.5 | 64.0 |
| 175 | 7 | 10.3 | 2.0 | 9.1 (6) | 49.7 | 91.2 |
| 200 | 6 | 15.1 | 2.0 | 9.0 (5) | 78.3 | 157 |

TABLE 15

Pharmacokinetics of orally administered squalamine (ENT-01) in Stage 2.
Stage 2

| Dose (mg) | # of patients (2 visits each) | $C_{max}$ (ng/ml) | $T_{max}$ (hour) (Median Value) | $T_{1/2}$ (hours) (n) | $AUC_{0-8\ hr}$ (ng*hour/ml) |
|---|---|---|---|---|---|
| 75 | 1 | 10.0 | 3.0 | 5.5 (1) | 59.0 |
| 100 | 4 | 17.7 | 1.0 | 4.8 (5) | 70.3 |
| 125 | | | | | |
| 150 | | | | | |
| 175 | 5 | 11.8 | 2.0 | 10 (6) | 66.8 |

The mean $C_{max}$, $T_{max}$ and $T_{1/2}$ and AUC of the squalamine ion following squalamine (ENT-01) oral dosing for Stage 1 patients. The PK analyses are only approximate, as the lower limit of the validated concentration range was 10 ng/ml; most of the measured concentrations fell below that value. The mean $C_{max}$, $T_{max}$ and $T_{1/2}$ and AUC of the squalamine ion following squalamine (ENT-01) oral dosing for Stage 2 patients. The PK analyses are only approximate, as the lower limit of the validated concentration range was 0.5 ng/ml.

CNS Symptoms in Stage 2: An exploratory analysis was done with respect to the sleep data, the body temperature data, mood, fatigue, hallucinations, cognition and other motor and non-motor symptoms of PD. Continuous measurements within a subject were compared with a paired t-test and continuous measurements between subject groups were compared with a two-group t-test. Categorical data were compared with a chi-squared test or a Fisher's exact test if the expected cell counts are too small for a chi-squared test.

CNS symptoms: CNS symptoms were evaluated at baseline and at the end of the fixed dose period and the wash-out period (Table 16). Total UPDRS score was 64.4 at baseline, 60.6 at the end of the fixed dose period and 55.7 at the end of the wash-out period (p=0.002); similarly, the motor component of the UPDRS improved from 35.3 at baseline to 33.3 at the end of fixed dose to 30.2 at the end of wash-out (p=0.006). MMSE improved from 28.4 at baseline to 28.7 during treatment and to 29.3 during wash-out (p=0.0006). BDI-II decreased from 10.9 at baseline to 9.9 during treatment and 8.7 at wash-out (p=0.10). PDHQ improved from 1.3 at baseline to 1.8 during treatment and 0.9 during wash-out (p=0.03). Hallucinations were reported by 5 patients at baseline and delusions in 1 patient. Both hallucinations and delusions improved or disappeared in 5 of 6 patients during treatment and did not return for 4 weeks following discontinuation of squalamine (ENT-01) in 1 patient and 2 weeks in another. The frequency of arm or leg thrashing reported in the sleep diary diminished progressively from 2.2 episodes/week at baseline to 0 at maximal dose. Total sleep time increased progressively from 7.1 hours at baseline to 8.4 hours at 250 mg and was consistently higher than baseline beyond 125 mg (FIG. 19). FIG. 21 shows REM-behavior disorder in relation to squalamine (ENT-01) dose, with arm and leg thrashing episodes (mean values) calculated using sleep diaries. The frequency of arm or leg thrashing reported in the sleep diary diminished progressively from 2.2 episodes/week at baseline to 0 at maximal dose. Unlike stool-related indices, the improvement in many CNS symptoms persisted during wash-out.

TABLE 16

| UPDRS | Baseline (Mean, SD) | Fixed dose (Mean, SD) | P-value | Wash-out (Mean, SD) | P-value |
|---|---|---|---|---|---|
| Part 1 (NMS) | 11.6 (6.51) | 10.6 (6.18)) | 0.28 | 9.5 (5.27) | 0.06 |
| Part 2 (Daily living) | 14.9 (8.11) | 14.7 (9.02) | 0.77 | 14.1 (8.21) | 0.40 |
| Part 3 (Motor) | 35.3 (14.35) | 33.3 (15.20) | 0.13 | 30.2 (13.23) | 0.005 |
| Total | 64.4 (23.72) | 60.6 (25.60) | 0.09 | 55.7 (23.69) | 0.002 |
| MMSE | 28.4 (1.75) | 28.7 (1.9) | 0.21 | 29.3 (1.06) | 0.0006 |
| PDHQ | 1.3 (2.99) | 1.8 (3.34) | 0.45 | 0.9 (2.33) | 0.03 |
| BDI-II | 10.9 (7.12) | 9.9 (6.45) | 0.14 | 8.7 (5.19) | 0.10 |

UPDRS: Unified Parkinson's Disease Severity Score;
NMS: Non-motor symptoms;
BDI: Beck Depression Index-II;
MMSE: Mini-mental State exam.
PDHQ: Parkinson's Disease Hallucination Questionnaire Circadian rhythm of skin temperature was evaluable in 12 patients (i.e., those who had recordings that extended from baseline through washout). Circadian system functionality was evaluated by continuously monitoring wrist skin temperature using a temperature sensor (Thermochron iButton DS1921H; Maxim, Dallas, Tex.) (Sarabia et al. 2008). A nonparametric analysis was performed for each participant to characterize DST as previously described (Sarabia et al. 2008; Ortiz-Tudela et al. 2010).

Briefly, this analysis includes the following parameters: (i) the inter-daily stability (the constancy of 24-hour rhythmic pattern over days, IS); (ii) intra-daily variability (rhythm fragmentation, IV); (iii) average of 10-minute intervals for the 10 hours with the minimum temperature (L10); (iv) average of 10-minute intervals for the 5 hours with the maximum temperature (M5) and the relative amplitude (RA), which was determined by the difference between M5 and L10, divided by the sum of both. Finally, the Circadian Function Index (CFI) was calculated by integrating IS, IV, and RA. Consequently, CFI is a global measure that oscillates between 0 for the absence of circadian rhythmicity and 1 for a robust circadian rhythm (Ortiz-Tudela et al. 2010).

A comparison was performed of circadian rhythm parameters during the baseline, fixed dose and washout periods. ENT-01 administration improved all markers of healthy circadian function, increasing rhythm stability (IS, p=0.026), relative amplitude (RA, p=0.001) and circadian function index (CFI, p=0.016), while reducing rhythm fragmentation (IV, p=0.031). The improvement persisted for several of these circadian parameters during wash-out period (IS, p=0.008 and CFI, p=0.004). (FIG. 20).

In particular, the following parameters were measured: Inter-daily variability (FIG. 20A), inter-daily stability (IS) (FIG. 20B), relative amplitude (RA) (FIG. 20C), circadian function index (FIG. 20D), M5V (FIG. 20E), which refers to the five consecutive hours with the highest temperature or high somnolence, and L10V (FIG. 20F), which indicates the mean of the ten consecutive hours with lowest temperature or high activation. The circadian function index (CFI) is an integrated score that ranges from 0 (absence of circadian rhythm) to 1 (robust circadian rhythm).

FIGS. 20A-F show the effect of squalamine (ENT-01) on circadian rhythm. The figures depict the results of circadian non-parametric analysis of wrist skin temperature rhythm throughout each condition (baseline, treatment with highest dose of squalamine (ENT-01) and washout).

Conclusions: This Phase 2 trial involving 50 patients with PD assessed the safety of orally administered ENT-01, and the effect on bowel function and neurologic symptoms of PD. In addition, the study aimed to identify a dose of ENT-01 that normalizes bowel function in each patient. The study achieved the objectives of identifying safety and pharmacodynamic responses of ENT-01 in PD. In addition, the study is the first proof of concept demonstration that directly targeting αS pharmacologically can achieve beneficial GI, autonomic and CNS responses.

The effective dose ranged between 75 mg and 250 mg, with 85% of patients responding within this range. This dose correlated positively with constipation severity at baseline consistent with the hypothesis that gastrointestinal dysmotility in PD results from the progressive accumulation of αS in the ENS, and that squalamine (ENT-01) can restore neuronal function by displacing αS and stimulating enteric neurons. These results demonstrate that the ENS in PD is not irreversibly damaged and can be restored to normal function.

Several exploratory endpoints were incorporated into the trial to evaluate the impact of ENT-01 on neurologic symptoms associated with PD. The UPDRS score, a global assessment of motor and non-motor symptoms, showed significant improvement. Improvement was also seen in the motor component. The improvement in the motor component is unlikely to be due to improved gastric motility and increased absorption of dopaminergic medications, since improvement persisted during the 2-week wash-out period, i.e., in the absence of study drug (Table 16).

Improvements were also seen in cognitive function (MMSE scores), hallucinations, REM-behavior disorder (RBD) and sleep. Six of the patients enrolled had daily hallucinations or delusions and these improved or disappeared during treatment in five. In one patient the hallucinations disappeared at 100 mg, despite not having reached the colonic prokinetic dose at 175 mg. The patient remained free of hallucinations for 1 month following cessation of dosing. RBD and total sleep time also improved progressively in a dose-dependent manner.

Since squalamine (ENT-01) has limited bioavailability the most reasonable mechanism for improvement in these symptoms would require communication between the GI tract and the CNS, either via a humoral mediator or more likely, via a direct a neural pathway connecting the ENS to the brain-stem and hypothalamus.

The prokinetic effect of the aminosterol squalamine appears to occur through local action of the compound on the ENS, since squalamine, the active zwitterion, is not significantly absorbed into the systemic circulation.

It will be apparent to those skilled in the art that various modifications and variations can be made in the methods and compositions of the present invention without departing from the spirit or scope of the invention. Thus, it is intended that the present invention cover the modifications and variations of this invention, provided they come within the scope of the appended claims and their equivalents.

REFERENCES

Ahima et al., "Appetite suppression and weight reduction by a centrally active aminosterol." *Diabetes,* 51(7): 2099-104 (2002).

Akhter et al., "Squalamine, a novel cationic steroid, specifically inhibits the brush-border Na+/H+ exchanger isoform NHE3." *Am. J. Physiol.,* 276(1 Pt 1): C136-44 (1999).

Alexander et al., "Membrane surface charge dictates the structure and function of the epithelial na+/h+ exchanger. EMBO J., 30:679-691 (2011).

Bhargava et al., "A phase I and pharmacokinetic study of squalamine, a novel antiangiogenic agent, in patients with advanced cancers," *Clin. Cancer Res.,* 7(12): 3912-9 (2001).

Connolly et al., "Squalamine lactate for exudative age-related macular degeneration," *Ophthalmol. Clin. North Am.,* 19:381-91 (2006).

Delgado et al., "Neuroprotective effect of vasoactive intestinal peptide (VIP) in a mouse model of Parkinson's disease by blocking microglial activation." *Faseb. J.,* 17(8): 944-6 (2003).

Genaidy et al., "Effect of squalamine on iris neovascularization in monkeys." *Retina,* 22(6): 772-8 (2002).

Genesis, A., "Squalamine trial for the treatment of fibrodysplasia ossificans progressiva initiated," *Angiogenesis Weekly,* 8:45 (2002).

Gonzalez-Rey et al., "Therapeutic effect of vasoactive intestinal peptide on experimental autoimmune encephalomyelitis: down-regulation of inflammatory and autoimmune responses," *Am. J. Pathol.,* 168(4): 1179-88 (2006).

Gressens et al., "Vasoactive intestinal peptide prevents excitotoxic cell death in the murine developing brain," *J. Clin. Invest.,* 100(2): 390-7 (1997).

Hao et al., "A Phase I and pharmacokinetic study of squalamine, an aminosterol angiogenesis inhibitor," *Clin. Cancer Res.,* 9(7): 2465-71 (2003).

Herbst et al., "A phase I/IIA trial of continuous five-day infusion of squalamine lactate (MSI-1256F) plus carboplatin and paclitaxel in patients with advanced non-small cell lung cancer," *Clin. Cancer Res.*, 9(11): 4108-15 (2003).

Higgins et al., "Squalamine improves retinal neovascularization," *Invest. Ophthalmol. Vis. Sci.*, 41(6): 1507-12 (2000).

Higgins et al., "Regression of retinopathy by squalamine in a mouse model," *Pediatr. Res.*, 56(1): 144-9 (2004).

Li et al., "Squalamine and cisplatin block angiogenesis and growth of human ovarian cancer cells with or without HER-2 gene overexpression," *Oncogene*, 21(18): 2805-14 (2002).

Li et al., "GLP-1 receptor stimulation preserves primary cortical and dopaminergic neurons in cellular and rodent models of stroke and Parkinsonism," *Proc. Natl. Acad. Sci. USA*, 106(4): 1285-90 (2009).

MacDonald, D. (1995). "Squalamine for STDs." Abstract no F7 35th ICAAC conference.

Moore et al., "Squalamine: an aminosterol antibiotic from the shark," *Proc. Natl. Acad. Sci. USA*, 90(4): 1354-8 (1993).

Rao et al., "Aminosterols from the dogfish shark *Squalus acanthias*," *J. Nat. Prod.*, 63(5): 631-5 (2000).

Salmi et al., "New stereoselective titanium reductive amination synthesis of 3-amino and polyaminosterol derivatives possessing antimicrobial activities," *Eur. J. Med. Chem.*, 43(3): 540-7 (2008).

Salmi et al., "Squalamine: an appropriate strategy against the emergence of multidrug resistant gram-negative bacteria?" *PLoS ONE*, 3(7): e2765 (2008).

Sarabia et al., "Circadian rhythm of wrist temperature in normal-living subjects A candidate of new index of the circadian system," *Physiol. Behav.*, 95:570-80 (2008).

Schiller, J. H. and G. Bittner, "Potentiation of platinum antitumor effects in human lung tumor xenografts by the angiogenesis inhibitor squalamine: effects on tumor neovascularization," *Clin. Cancer Res.*, 5(12): 4287-94 (1999).

Selinsky et al., "Squalamine is not a proton ionophore," *Biochim. Biophys. Acta.*, 1464(1): 135-41 (2000).

Selinsky et al., "The aminosterol antibiotic squalamine permeabilizes large unilamellar phospholipid vesicles," *Biochim. Biophys. Acta.*, 1370(2): 218-34 (1998).

Sills et al., "Squalamine inhibits angiogenesis and solid tumor growth in vivo and perturbs embryonic vasculature," *Cancer Res.*, 58(13): 2784-92 (1998).

Sokoloff et al., "Adjunctive therapy for men with high risk localized and locally advanced prostate cancer: targeting disseminated tumor cells," *J. Urol.*, 172(6 Pt 2): 2539-44 (2004).

Steinberg, B. E. and S. Grinstein, "Pathogen destruction versus intracellular survival: the role of lipids as phagosomal fate determinants," *J. Clin. Invest.*, 118(6): 2002-11 (2008).

Sumioka et al., "TARP phosphorylation regulates synaptic AMPA receptors through lipid bilayers," *Neuron*, 66(5): 755-67 (2009).

Tirassa et al., "CCK-8 prevents the development of kindling and regulates the GABA and NPY expression in the hippocampus of pentylenetetrazole (PTZ)-treated adult rats," *Neuropharmacology*, 48(5): 732-42 (2005).

US2005/0261508A1 for "Aminosterol Compounds useful as inhibitors of the sodium/proton exchanger (NHE), pharmaceutical methods, and compositions employing such inhibitors, and processes for evaluating the NHE-inhibtory efficacy of compounds," Zasloff et al., Published Nov. 24, 2005.

US2006/0166950A1 for "Treatment of neovascularization disorders with squalamine," Zasloff et al., Published Jun. 27, 2006.

US2006/0183928A1 for "Aminosterol Compounds useful as inhibitors of the sodium/proton exchanger (NHE), pharmaceutical methods, and compositions employing such inhibitors, and processes for evaluating the NHE-inhibtory efficacy of compounds", Published Aug. 17, 2006.

US2007/10504A1 for "Polymorphic and Amorphous salt forms of squalamine dilactate" Chellquist, Doubleday, Gilbert, Zhang, McLane, Armbruster, Levitt, Published Jan. 11, 2007.

US2011/0097303 for "Methods and Compositions for Treating and Preventing Viral Infections," published Apr. 28, 2011, Zasloff); U.S. (2011) Ser. No. 12/913,648.

U.S. Pat. No. 5,192,756 for "Aminosterol antibiotic," Zasloff, Moore, Wehrli, Issued Mar. 9, 1993.

U.S. Pat. No. 5,637,691 (1993) for "Steroid derivatives, pharmaceutical compositions containing them, and their use as antibiotics and disinfectants", Frye, Zasloff, Kinney, Moriarty.

U.S. Pat. No. 5,721,226 (1998) for "Methods for treating angiogenesis using squalamine and squalamine steroid derivatives," Frye, Zasloff, Kinney, Moriarty, Collins.

U.S. Pat. No. 5,733,899 (1998) for "Methods for treating infections using steroid based pharmaceutical compositions," Frye, Zasloff, Kinney, Moriarty, Collins.

U.S. Pat. No. 5,763,430 (1998) for "Method of treating a viral infection by administering a steroid compound," Zasloff.

U.S. Pat. No. 5,792,635 (1998) for "Method of inhibiting the sodium-proton exchanger NHE3 and method of inhibiting growth by administering squalamine," Zasloff.

U.S. Pat. No. 5,795,885 (1998) for "Method of Inhibiting proliferation of cells by administering an aminosterol compound," Zasloff, Shinnar, Kinney, Anderson, Williams, McLane.

U.S. Pat. No. 5,834,453 (1998) for "Methods for the manufacture and use of antimicrobial sterol conjugates," Regen (Leheigh Univ).

U.S. Pat. No. 5,840,740 (1998) for "Aminosterol compounds and a method of treating infection using the aminosterol compounds," Zasloff, Shinnar, Kinney, Rao.

U.S. Pat. No. 5,840,936 (1998) for "Aminosterol compounds useful as inhibitors of the sodium/proton exchanger (NHE)," Zasloff, Shinnar, Rao, Kinney.

U.S. Pat. No. 5,847,172 (1998) for "Certain Aminosterol compounds and Pharmaceutical compositions including these compounds," Zasloff, Shinnar, Kinney, Jones.

U.S. Pat. No. 5,856,535 (1999) for "Aminosterol ester compounds," Zasloff, Kinney, Jones.

U.S. Pat. No. 5,874,597 (1999) for "Certain Aminosterol compounds and pharmaceutical compositions including these compounds," Jones, Issued Feb. 23, 1999.

U.S. Pat. No. 5,994,336 (1999) for "Method of inhibiting proliferation of cells by administering an aminosterol compound," Zasloff, Shinnar, Kinney, Rao, Issued Nov. 30, 1999.

U.S. Pat. No. 6,017,906 (2000) for "Polyamine conjugates for treatment of infection," Mintz, C S et al Intercardia, Inc., Issued Jan. 25, 2000.

U.S. Pat. No. 6,143,738 (2000) for "Therapeutic uses for an aminosterol compound," Zasloff, Issued Nov. 7, 2000.

U.S. Pat. No. 6,147,060 (2000) for "Treatment of carcinomas using squalamine in combination with other anti-cancer agents," Zasloff, Williams, Issued Nov. 14, 2000.

U.S. Pat. No. 6,388,108 (2002) for "Aminosterol compounds and uses thereof," Rao, Feibush, Kinney, Zasloff, Noecker, Issued May 14, 2002.

U.S. Pat. No. 6,596,712 (2003) for "Treatment of carcinomas using squalamine in combination with other anticancer agents or modalities," Zasloff, Williams, Sokoloff, Issued Jul. 22, 2003.

U.S. Pat. No. 6,962,909 (2005) for "Treatment of neovascularization disorders with squalamine," Zasloff, Shinnar, Kinney, Jones, Issued Nov. 8, 2005.

U.S. Pat. No. 8,729,058 for "Methods And Compositions For Treating And Preventing Viral Infections," Zasloff et al., issued May 20, 2014.

Verdin et al., "Characterization of a common high-affinity receptor for reovirus serotypes 1 and 3 on endothelial cells," *J. Virol.*, 63(3): 1318-25 (1989).

White et al., "Therapeutic potential of vasoactive intestinal peptide and its receptors in neurological disorders," *CNS Neurol. Disord. Drug Targets,* 9(5): 661-6 (2010).

Williams et al., "Squalamine treatment of human tumors in nu/nu mice enhances platinum-based chemotherapies," *Clin. Cancer Res.,* 7(3): 724-33 (2001).

WO 96/08270 (1996) for "Method for inhibiting sexually transmitted diseases using Magainin antimicrobials or Squalamine Compounds," Jacob, Zasloff, Williams, Bedi.

Yeung et al., "Membrane phosphatidylserine regulates surface charge and protein localization," *Science,* 319 (5860): 210-3 (2008).

Yin et al., "Antiangiogenic treatment delays chondrocyte maturation and bone formation during limb skeletogenesis," *J. Bone Miner. Res.,* 17(1): 56-65 (2002).

Yun et al., "Identification of Squalamine in the Plasma Membrane of White Blood Cells in the Sea Lamprey," *Petromyzon marinus,"* *J. Lipid Res.,* 48(12): 2579-2586 (2007).

Zasloff, M., "Antimicrobial peptides of multicellular organisms," *Nature,* 415(6870): 389-95 (2002).

Zasloff et al., "A spermine-coupled cholesterol metabolite from the shark with potent appetite suppressant and antidiabetic properties," *Int. J. Obes. Relat. Metab. Disord.,* 25(5): 689-97 (2001).

Zasloff et al., "Squalamine as a broad-spectrum systemic antiviral agent with therapeutic potential," *Proc. Natl. Acad. Sci. USA,* 108(38): 15978-83 (2011).

What is claimed:

1. A method of treating a sleep disorder in a subject comprising administering to a subject in need thereof, a composition comprising a pharmaceutically acceptable grade of at least one aminosterol, or a pharmaceutically acceptable salt or derivative thereof, in an amount sufficient to produce a beneficial effect, wherein the composition does not comprise another active agent in addition to the at least one aminosterol, or a pharmaceutically acceptable salt or derivative thereof, wherein:
   (a) administration of the composition decreases the occurrence of at least one symptom of the sleep disorder;
   (b) progression or onset of the sleep disorder is slowed, halted, or reversed over a defined time period following administration of the composition, as measured by a medically-recognized technique, tool or scale; and/or
   (c) the sleep disorder is positively impacted by administration of the composition, as measured by a clinically-recognized technique, tool or scale, and wherein the sleep disorder is associated with a neurodegenerative disorder or disease.

2. The method of claim 1, wherein:
   (a) treating the sleep disorder prevents or delays the onset or progression of the neurodegenerative disorder; and/or
   (b) the neurodegenerative disorder is selected from the group consisting of Parkinson's disease, Alzheimer's disease, Huntington's chorea and/or Disease, schizophrenia, multiple sclerosis, dementia, degenerative processes associated with aging, dementia of aging, multi-system atrophy (MSA), fronto-temporal dementia, autism, progressive nuclear palsy, Guadeloupian Parkinsonism, spinocerebellar ataxia, Amyotorphic Lateral Sclerosis (ALS), Friedreich's ataxia, vascular dementia, Lewy Body dementia or disease, spinal muscular atrophy, supranuclear palsy, fronto temperal dementia, neuropathy of diabetes, peripheral sensory, neuropathy, cerebral palsy, epilepsy, diabetic neuropathy, and depression.

3. The method of claim 1, further comprising:
   (a) determining an effective dose of an aminosterol or a pharmaceutically acceptable salt or derivative thereof for the subject, wherein the effective dose is determined based on the effectiveness of the aminosterol dose in improving or resolving the sleep disorder,
   (b) followed by administering the effective dose to the subject for a period of time, wherein the method comprises:
      (i) identifying a sleep disorder or related symptom to be evaluated, wherein the related symptom is used as a marker to determine the effective dose resulting in substantial improvement or resolution of the sleep disorder;
      (ii) identifying a starting aminosterol dose for the subject; and
      (iii) administering an escalating dose of the aminosterol to the subject over a period of time until an effective dose for the sleep disorder or related symptom being evaluated is identified, wherein the effective dose is the aminosterol dose where improvement or resolution of the sleep disorder or related symptom is observed, and fixing the aminosterol dose at that level for that particular sleep disorder or related symptom in that particular subject,
   wherein the effective dose results in substantial improvement or resolution of the sleep disorder.

4. The method of claim 3, wherein the composition is administered orally, intranasally, or a combination thereof.

5. The method of claim 4, wherein the composition is administered orally and:
   (a) the starting aminosterol dose ranges from about 1 mg up to about 175 mg/day;
   (b) the dose of the aminosterol or a pharmaceutically acceptable salt or derivative thereof for the subject following escalation is fixed at a range of from about 1 mg up to about 500 mg/day; and/or
   (c) the dose of the aminosterol or a pharmaceutically acceptable salt or derivative thereof is escalated in about 25 mg increments.

6. The method of claim 4, wherein the composition is administered intranasally and:
   (a) the starting dose of the aminosterol or a pharmaceutically acceptable salt or derivative thereof ranges from about 0.001 mg to about 3 mg/day;
   (b) the dose of the aminosterol or a pharmaceutically acceptable salt or derivative thereof for the subject following escalation is fixed at a range of from about 0.001 mg up to about 6 mg/day;
   (c) the dose of the aminosterol or a pharmaceutically acceptable salt or derivative thereof for the subject following escalation is a dose which is subtherapeutic when given orally or by injection; and/or (d) the dose of the aminosterol or a pharmaceutically acceptable salt or derivative thereof is escalated in increments of about 0.1, about 0.2, about 0.25, about 0.3, about 0.35, about 0.4, about 0.45, about 0.5, about 0.55, about 0.6, about 0.65, about 0.7, about 0.75, about 0.8, about 0.85, about 0.9, about 0.95, about 1, about 1.1, about 1.2, about 1.3, about 1.4, about 1.5, about 1.6, about 1.7, about 1.8, about 1.9, or about 2 mg.

7. The method of claim 3, wherein:
(a) the dose of the aminosterol or a pharmaceutically acceptable salt or derivative thereof is escalated every about 3 to about 5 days;
(b) the dose of the aminosterol or a pharmaceutically acceptable salt or derivative thereof is escalated every about 1, about 2, about 3, about 4, about 5, about 6, about 7, about 8, about 9, about 10, about 11, about 12, about 13, or about 14 days;
(c) the dose of the aminosterol or a pharmaceutically acceptable salt or derivative thereof is escalated about 1×/week, about 2×/week, about every other week, or about 1×/month;
(d) the dose of the aminosterol or a pharmaceutically acceptable salt or derivative thereof is given once per day, every other day, once per week, twice per week, three times per week, four times per week, five times per week, six times per week, every other week, or every few days;
(e) the dose of the aminosterol or a pharmaceutically acceptable salt or derivative thereof is given for a few weeks, followed by skipping a few weeks, followed by restarting aminosterol treatment;
(f) the dose of the aminosterol or a pharmaceutically acceptable salt or derivative thereof is incrementally reduced after the fixed dose of aminosterol or a pharmaceutically acceptable salt or derivative thereof has been administered to the subject for a period of time;
(g) the dose of the aminosterol or a pharmaceutically acceptable salt or derivative thereof is varied plus or minus a defined amount to enable a modest reduction or increase in the fixed dose;
(h) the dose of the aminosterol or a pharmaceutically acceptable salt or derivative thereof is varied plus or minus a defined amount to enable a modest reduction or increase in the fixed dose, and the fixed aminosterol dose is increased or decreased by about 1%, about 2%, about 3%, about 4%, about 5%, about 6%, about 7%, about 8%, about 9%, about 10%, about 11%, about 12%, about 13%, about 14%, about 15%, about 16%, about 17%, about 18%, about 19%, or about 20%; and/or
(i) the starting dose of the aminosterol or a pharmaceutically acceptable salt or derivative thereof is higher if the symptom being evaluated is severe.

8. The method of claim 3, wherein the sleep disorder or related symptom to be evaluated is selected from the group consisting of:
(1) total sleep time;
(2) total number of hours of uninterrupted sleep, per day;
(3) sleep efficiency;
(4) presence or frequency of a change in sleeping patterns;
(5) presence or frequency of a change in Circadian rhythm;
(6) developing a normal Circadian (i.e., diurnal) rhythm;
(7) presence of a sleep-wake cycle that is not 24 hours;
(8) sleeping at night rather than during the day, when night would is the preferred sleeping period;
(9) presence and/or frequency of awakenings during sleep period;
(10) presence and/or frequency of nonrestorative sleep;
(11) presence and/or frequency of a difficulty maintaining sleep;
(12) presence and/or frequency of sleep fragmentation;
(13) presence and/or frequency of hallucinations during sleep period;
(14) presence and/or frequency of thrashing or limb movement during sleep period;
(15) presence and/or frequency of nightmares and/or vivid dreams;
(16) presence and/or frequency of delayed sleep onset;
(17) presence and/or frequency of day time sleepiness;
(18) presence and/or frequency of clinical or sub-clinical "sleep attacks";
(19) cognitive impairment and/or improvement in memory as a result of better memory consolidation during sleep;
(20) presence and/or frequency of disturbances in sleep architecture;
(21) time of awakening following sleep period, with a later time correlated with improved sleep;
(22) presence and/or frequency of sleep problems;
(23) presence and/or frequency of sleep disturbances and/or sleep disruption;
(24) REM disturbed sleep;
(25) presence and/or frequency of apnea;
(26) presence and/or frequency of narcolepsy;
(27) poor psychomotor coordination;
(28) presence and/or frequency of headaches;
(29) presence and/or frequency of gastrointestinal distress;
(30) presence and/or frequency of insomnia;
(31) presence and/or frequency of parasomnias;
(32) diurnal skin temperature oscillations;
(33) a symptom from the Horne-Östberg Morningness-Eveningness Questionnaire (MEQ) selected from the group consisting of difficulty waking up in the morning, difficulty falling asleep at night, falling asleep earlier than normal at night, dependence on alarm to wake in morning, lack of alertness in morning, appetite upon waking in morning, feeling tired after waking in the morning, going to bed later than normal when subject has no commitments the following day, inability to fall back to sleep upon waking in the morning, lack of willingness to engage in physical activity in the morning, and lack of willingness to engage in cognitively challenging tasks in the morning;
(34) a symptom from the Epworth Sleepiness Scale (ESS) selected from the group consisting of dozing or sleeping when sitting and reading, dozing or sleeping when watching television (TV), dozing or sleeping when sitting while inactive in public, dozing or sleeping when riding as a passenger in a car for greater than 1 hour, dozing or sleeping when lying down in the afternoon, dozing or sleeping when talking to another person, dozing or sleeping when sitting quietly after lunch, and dozing or sleeping when driving and stopped in traffic;
(35) REM behavior disorder (RBD);
(36) circadian rhythm dysfunction;
(37) Restless leg syndrome;
(38) jet lag;
(39) hypersomnia; and/or
(40) personal judgement of restful sleep.

9. The method of claim 1, wherein:
(a) the progression or onset of the sleep disorder is slowed, halted, or reversed by about 5%, about 10%, about 15%, about 20%, about 25%, about 30%, about 35%, about 40%, about 45%, about 50%, about 55%, about 60%, about 65%, about 70%, about 75%, about 80%, about 85%, about 90%, about 95%, or about 100%, as measured by a medically-recognized technique, tool or scale; and/or
(b) the positive impact on the sleep disorder is at least about 10%, at least about 15%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 95%, or at least about 100%, as measured using a clinically recognized scale, tool, or technique.

10. The method of claim 1, wherein:
(a) the method results in a positive change in the sleeping pattern of the subject;
(b) the method results in a positive change in the sleeping pattern of the subject, wherein the positive change is defined as an increase in the total amount of sleep obtained of about 5%, about 10%, about 15%, about 20%, about 25%, about 30%, about 35%, about 40%, about 45%, about 50%, about 55%, about 60%, about 65%, about 70%, about 75%, about 80%, about 85%, about 90%, about 95%, or about 100%;
(c) the method results in a positive change in the sleeping pattern of the subject, and the positive change is defined as a percent decrease in the number of awakenings during the night selected from the group consisting of about 5%, about 10%, about 15%, about 20%, about 25%, about 30%, about 35%, about 40%, about 45%, about 50%, about 55%, about 60%, about 65%, about 70%, about 75%, about 80%, about 85%, about 90%, about 95%, or about 100%; and/or
(d) as a result of the method the subject obtains the total number of hours of sleep recommended by a medical authority for the age group of the subject.

11. The method of claim 1, wherein the aminosterol:
(a) is isolated from the liver of *Squalus acanthias;*
(b) is squalamine or a pharmaceutically acceptable salt thereof;
(c) is a squalamine isomer or derivative;
(d) is aminosterol 1436 or a pharmaceutically acceptable salt thereof;
(e) is an aminosterol 1436 isomer or derivative;
(f) has a sterol nucleus and a polyamine attached at any position on the sterol, such that, the molecule exhibits a net charge of at least +1;
(g) has a bile acid nucleus and a polyamine, attached at any position on the bile acid, such that the molecule exhibits a net charge of at least +1;
(h) is a derivative of squalamine or aminosterol 1436 modified through medical chemistry to improve bio-distribution, ease of administration, metabolic stability, or any combination thereof;
(i) is a derivative of a natural aminosterol modified through medical chemistry to improve bio-distribution, ease of administration, metabolic stability, or any combination thereof;
(j) is a synthetic aminosterol; or
(k) is a derivative modified to include one or more of the following:
(i) substitutions of the sulfate by a sulfonate, phosphate, carboxylate, or other anionic moiety chosen to circumvent metabolic removal of the sulfate moiety and oxidation of the cholesterol side chain;
(ii) replacement of a hydroxyl group by a non-metabolizable polar substituent to prevent its metabolic oxidation or conjugation; and/or
(iii) substitution of one or more ring hydrogen atoms to prevent oxidative or reductive metabolism of the steroid ring system.

12. The method of claim 11, wherein the aminosterol is squalamine or a pharmaceutically acceptable salt thereof or aminosterol 1436 or a pharmaceutically acceptable salt thereof.

13. The method of claim 1, wherein the aminosterol is a phosphate salt.

14. The method of claim 1, wherein the composition further comprises one or more of the following: (a) an aqueous carrier; (b) a buffer; (c) a sugar; and/or (d) a polyol compound.

15. The method of claim 1, wherein:
(a) each aminosterol dose is taken on an empty stomach, optionally within two hours of the subject waking; and/or
(b) no food is taken after about 60 to about 90 minutes of taking the aminosterol dose.

16. The method of claim 1, wherein the subject is a human.

17. The method of claim 1, wherein the aminosterol is administered orally.

18. The method of claim 1, wherein the aminosterol is administered non-orally.

19. The method of claim 12, wherein the aminosterol is squalamine or a pharmaceutically acceptable salt thereof.

20. The method of claim 1, wherein the composition is administered orally, intranasally, or a combination thereof.

* * * * *